United States Patent
Bernstein et al.

(10) Patent No.: US 11,911,083 B2
(45) Date of Patent: Feb. 27, 2024

(54) BONE FIXATION SYSTEM WITH OPPOSED MOUNTING PORTIONS

(71) Applicant: Acumed LLC, Hillsboro, OR (US)

(72) Inventors: Oren S. Bernstein, Portland, OR (US); Joel Gillard, Portland, OR (US); Eric Thorsell, Portland, OR (US); Sara Russi, Portland, OR (US); Kyle A. Loucks, Ridgefield, WA (US); Andrew W. Seykora, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 28 days.

(21) Appl. No.: 17/396,135

(22) Filed: Aug. 6, 2021

(65) Prior Publication Data

US 2021/0361329 A1 Nov. 25, 2021

Related U.S. Application Data

(63) Continuation of application No. 15/804,638, filed on Nov. 6, 2017, now Pat. No. 11,083,504, which is a
(Continued)

(51) Int. Cl.
*A61B 17/17* (2006.01)
*A61B 17/88* (2006.01)
(Continued)

(52) U.S. Cl.
CPC .......... *A61B 17/80* (2013.01); *A61B 17/1728* (2013.01); *A61B 17/808* (2013.01);
(Continued)

(58) Field of Classification Search
CPC ... A61B 17/282; A61B 17/158; A61B 17/808; A61B 17/1728; A61B 17/8057;
(Continued)

(56) References Cited

U.S. PATENT DOCUMENTS

| 20,503 A | 6/1858 | Morse |
|---|---|---|
| 820,503 A | 5/1906 | Krengel et al. |

(Continued)

FOREIGN PATENT DOCUMENTS

| AU | 8975091 A | 2/1992 |
|---|---|---|
| CA | 2452127 A1 | 12/1993 |

(Continued)

OTHER PUBLICATIONS

Synthes, Titanium Distal Radius Instrument and Implant Set standard contents description pages, Mar. 1997.
(Continued)

*Primary Examiner* — Marcela I. Shirsat
(74) *Attorney, Agent, or Firm* — K&L Gates LLP

(57) ABSTRACT

System, including methods, apparatus, and kits, for bone fixation using a fixation device including a mounting portion and a fastener that attaches to the mounting portion. In some embodiments, the fixation device may include first and second mounting portions configured to be disposed across a bone from each other and secured with a fastener that extends from one of the mounting portions, through the bone, and to the other mounting portion. The system also may include a tool to facilitate installation of the fixation device.

20 Claims, 15 Drawing Sheets

Related U.S. Application Data continuation of application No. 14/207,058, filed on Mar. 12, 2014, now Pat. No. 9,808,297, which is a continuation-in-part of application No. 12/903,024, filed on Oct. 12, 2010, now Pat. No. 8,679,122, and a continuation-in-part of application No. 13/287,955, filed on Nov. 2, 2011, now abandoned, and a continuation-in-part of application No. 13/633,024, filed on Oct. 1, 2012, now Pat. No. 9,775,657, and a continuation-in-part of application No. 13/752,188, filed on Jan. 28, 2013, now Pat. No. 9,237,910, and a continuation-in-part of application No. 13/874,171, filed on Apr. 30, 2013, now Pat. No. 9,241,748, which is a continuation-in-part of application No. 13/942,459, filed on Jul. 15, 2013, now Pat. No. 9,237,913, said application No. 13/942,459 is a continuation of application No. 12/249,252, filed on Oct. 10, 2008, now Pat. No. 8,486,114.

(60) Provisional application No. 61/250,389, filed on Oct. 9, 2009, provisional application No. 61/409,415, filed on Nov. 2, 2010, provisional application No. 61/542,046, filed on Sep. 30, 2011, provisional application No. 61/590,955, filed on Jan. 26, 2012, provisional application No. 61/640,486, filed on Apr. 30, 2012, provisional application No. 61/641,703, filed on May 2, 2012.

(51) Int. Cl.
| | |
|---|---|
| *A61B 90/00* | (2016.01) |
| *A61B 17/80* | (2006.01) |
| *A61B 17/86* | (2006.01) |
| *A61B 90/92* | (2016.01) |
| *A61B 17/064* | (2006.01) |
| *A61B 17/82* | (2006.01) |

(52) U.S. Cl.
CPC ...... *A61B 17/8057* (2013.01); *A61B 17/8076* (2013.01); *A61B 17/863* (2013.01); *A61B 17/8863* (2013.01); *A61B 90/92* (2016.02); *A61B 17/064* (2013.01); *A61B 17/0643* (2013.01); *A61B 17/1792* (2016.11); *A61B 17/8085* (2013.01); *A61B 17/82* (2013.01); *A61B 17/8869* (2013.01); *A61B 2017/0645* (2013.01); *A61B 2090/034* (2016.02); *A61B 2090/061* (2016.02)

(58) Field of Classification Search
CPC ............ A61B 17/8061; A61B 17/8076; A61B 17/1792; A61B 17/8085
USPC ......... 606/75, 53, 283, 284, 285, 87, 96, 99, 606/101, 86 B
See application file for complete search history.

(56) References Cited

U.S. PATENT DOCUMENTS

| | | |
|---|---|---|
| 869,697 A | 10/1907 | Eilhauer et al. |
| 1,105,105 A | 7/1914 | Sherman |
| 1,156,440 A | 10/1915 | Smith |
| 1,345,425 A | 7/1920 | Wells |
| 1,789,060 A | 1/1931 | Weisenbach |
| 1,889,239 A | 11/1932 | Crowley |
| 1,950,799 A | 3/1934 | Jones |
| 2,181,746 A * | 11/1939 | Siebrandt ............ A61B 17/282 7/125 |
| 2,406,832 A | 9/1946 | Hardinge |
| 2,443,363 A | 6/1948 | Townsend et al. |
| 2,489,870 A | 11/1949 | Dzus |
| 2,494,229 A | 1/1950 | Collison |
| 2,496,126 A | 1/1950 | Haboush |
| 2,500,370 A | 3/1950 | McKibbin |
| 2,500,993 A | 3/1950 | Mason |
| 2,526,959 A | 10/1950 | Lorenzo |
| 2,579,968 A | 12/1951 | Rush |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,346,894 A | 10/1967 | Lemelson |
| 3,357,432 A | 12/1967 | Sparks |
| 3,386,437 A | 6/1968 | Treace |
| 3,422,170 A | 1/1969 | Brooks et al. |
| 3,477,429 A | 11/1969 | Sampson |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,716,050 A | 2/1973 | Johnston |
| 3,726,279 A | 4/1973 | Barefoot et al. |
| 3,741,205 A | 6/1973 | Markolf et al. |
| 3,759,257 A | 9/1973 | Fischer et al. |
| 3,774,244 A | 11/1973 | Walker |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,960,147 A | 6/1976 | Murray |
| 3,965,720 A | 6/1976 | Goodwin et al. |
| 4,000,525 A | 1/1977 | Klawitter et al. |
| 4,011,863 A | 3/1977 | Zickel |
| 4,055,172 A | 10/1977 | Ender et al. |
| 4,091,806 A | 5/1978 | Aginsky |
| 4,119,092 A | 10/1978 | Gil |
| 4,135,507 A | 1/1979 | Harris |
| 4,169,470 A | 10/1979 | Ender et al. |
| 4,187,840 A | 2/1980 | Watanabe |
| 4,187,841 A | 2/1980 | Knutson |
| 4,201,215 A | 5/1980 | Crossett et al. |
| 4,263,904 A | 4/1981 | Judet |
| 4,327,715 A | 5/1982 | Corvisier |
| 4,364,382 A | 12/1982 | Mennen |
| 4,378,607 A | 4/1983 | Wadsworth |
| 4,388,921 A | 6/1983 | Sutter et al. |
| 4,408,601 A | 10/1983 | Wenk |
| 4,444,181 A | 4/1984 | Wevers et al. |
| RE31,628 E | 7/1984 | Allgower et al. |
| 4,457,307 A | 7/1984 | Stillwell |
| 4,473,069 A | 9/1984 | Kolmert |
| 4,483,335 A | 11/1984 | Tornier |
| 4,484,570 A | 11/1984 | Sutter et al. |
| 4,493,317 A | 1/1985 | Klaue |
| 4,503,847 A | 3/1985 | Mouradian |
| 4,506,662 A | 3/1985 | Anapliotis |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,630,601 A | 12/1986 | Harder et al. |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,733,654 A | 3/1988 | Marino |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |

(56) References Cited

U.S. PATENT DOCUMENTS

| | | |
|---|---|---|
| 4,828,492 A | 5/1989 | Agnone |
| 4,867,144 A | 9/1989 | Karas et al. |
| 4,892,093 A | 1/1990 | Zarnowski et al. |
| 4,893,619 A | 1/1990 | Dale et al. |
| 4,896,661 A | 1/1990 | Bogert et al. |
| 4,903,691 A | 2/1990 | Heinl |
| 4,905,679 A | 3/1990 | Morgan |
| 4,915,092 A | 4/1990 | Firica et al. |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karás et al. |
| 4,966,599 A | 10/1990 | Pollock |
| 4,973,332 A | 11/1990 | Kummer |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,013,314 A | 5/1991 | Firica et al. |
| 5,013,315 A | 5/1991 | Barrows |
| 5,015,248 A | 5/1991 | Burstein et al. |
| 5,021,056 A | 6/1991 | Hofmann et al. |
| 5,035,697 A | 7/1991 | Frigg |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,116,335 A | 5/1992 | Hannon et al. |
| 5,129,899 A | 7/1992 | Small et al. |
| 5,133,718 A | 7/1992 | Mao |
| 5,135,527 A | 8/1992 | Ender |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,736 A | 4/1993 | Strauss |
| 5,201,737 A | 4/1993 | Leibinger et al. |
| 5,234,431 A | 8/1993 | Keller |
| 5,246,443 A | 9/1993 | Mai |
| 5,254,119 A | 10/1993 | Schreiber |
| 5,261,908 A | 11/1993 | Campbell, Jr. |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,356,410 A | 10/1994 | Pennig |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Tom Du Toit |
| 5,423,826 A | 6/1995 | Coates et al. |
| 5,437,677 A * | 8/1995 | Shearer .............. A61B 17/1778 606/86 R |
| 5,443,483 A | 8/1995 | Kirsch |
| 5,443,516 A | 8/1995 | Albrektsson et al. |
| 5,449,359 A | 9/1995 | Groiso |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Procter et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,571,103 A | 11/1996 | Bailey |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,603,715 A | 2/1997 | Kessler |
| 5,607,426 A | 3/1997 | Ralph et al. |
| 5,643,261 A | 7/1997 | Schäfer et al. |
| 5,643,265 A | 7/1997 | Errico et al. |
| 5,645,599 A | 7/1997 | Samani |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,665 A | 10/1997 | Bryan |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,814,047 A | 9/1998 | Emilio et al. |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,888,247 A | 3/1999 | Benetti |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo et al. |
| 5,968,046 A | 10/1999 | Castleman |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,004,353 A | 12/1999 | Masini |
| 6,007,535 A | 12/1999 | Rayhack et al. |
| 6,007,538 A | 12/1999 | Levin |
| 6,022,350 A | 2/2000 | Ganem |
| 6,027,504 A | 2/2000 | McGuire |
| 6,053,915 A | 4/2000 | Bruchmann |
| 6,077,266 A | 6/2000 | Medoff |
| 6,077,271 A | 6/2000 | Huebner et al. |
| 6,093,188 A | 7/2000 | Murray |
| 6,096,040 A | 8/2000 | Esser |
| 6,113,603 A | 9/2000 | Medoff |
| 6,117,139 A | 9/2000 | Shino |
| 6,117,160 A | 9/2000 | Bonutti |
| 6,123,709 A | 9/2000 | Jones |

(56) References Cited

U.S. PATENT DOCUMENTS

| | | |
|---|---|---|
| 6,129,728 A | 10/2000 | Schumacher et al. |
| 6,129,730 A | 10/2000 | Bono et al. |
| 6,139,548 A | 10/2000 | Errico |
| 6,152,927 A | 11/2000 | Farris et al. |
| 6,159,213 A | 12/2000 | Rogozinski |
| 6,179,839 B1 | 1/2001 | Weiss et al. |
| 6,183,475 B1 | 2/2001 | Lester et al. |
| 6,193,721 B1 | 2/2001 | Michelson |
| 6,197,028 B1 | 3/2001 | Ray et al. |
| 6,197,037 B1 | 3/2001 | Hair |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dall |
| 6,261,291 B1 | 7/2001 | Talaber et al. |
| 6,273,889 B1 | 8/2001 | Richelsoph |
| 6,280,446 B1 | 8/2001 | Blackmore |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |
| 6,315,779 B1 | 11/2001 | Morrison et al. |
| 6,322,562 B1 | 11/2001 | Wolter |
| 6,325,803 B1 | 12/2001 | Schumacher et al. |
| 6,331,179 B1 | 12/2001 | Freid et al. |
| 6,336,927 B2 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,041 B1 | 3/2002 | Martin |
| 6,355,042 B2 | 3/2002 | Winquist et al. |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,359 B1 | 4/2002 | Dahners |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B2 | 8/2002 | Orbay et al. |
| 6,440,169 B1 | 8/2002 | Elberg et al. |
| 6,454,769 B2 | 9/2002 | Wagner et al. |
| 6,454,770 B1 | 9/2002 | Klaue |
| 6,458,133 B1 | 10/2002 | Lin |
| 6,503,250 B2 | 1/2003 | Paul |
| 6,508,819 B1 | 1/2003 | Orbay |
| 6,514,274 B1 | 2/2003 | Boucher et al. |
| 6,520,965 B2 | 2/2003 | Chervitz et al. |
| 6,527,775 B1 | 3/2003 | Warburton |
| 6,533,789 B1 | 3/2003 | Hall, IV et al. |
| 6,547,790 B2 | 4/2003 | Harkey, III et al. |
| 6,565,570 B2 | 5/2003 | Sterett et al. |
| 6,572,620 B1 | 6/2003 | Schon et al. |
| 6,592,578 B2 | 7/2003 | Henniges et al. |
| 6,595,993 B2 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,682,531 B2 | 1/2004 | Winquist et al. |
| 6,682,533 B1 | 1/2004 | Dinsdale et al. |
| 6,689,139 B2 | 2/2004 | Horn |
| 6,695,846 B2 | 2/2004 | Richelsoph et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |
| 6,863,694 B1 | 3/2005 | Boyce et al. |
| 6,866,665 B2 | 3/2005 | Orbay |
| 6,893,444 B2 | 5/2005 | Orbay |
| 6,955,677 B2 | 10/2005 | Dahners |
| 6,969,391 B1 | 11/2005 | Gazzani |
| 6,974,461 B1 | 12/2005 | Wolter |
| 7,011,659 B2 | 3/2006 | Lewis et al. |
| 7,070,600 B2 | 7/2006 | Silverman |
| 7,077,844 B2 | 7/2006 | Michelson |
| 7,153,309 B2 | 12/2006 | Huebner et al. |
| 7,635,365 B2 | 12/2009 | Ellis et al. |
| 7,695,501 B2 | 4/2010 | Ellis et al. |
| 7,695,502 B2 | 4/2010 | Orbay et al. |
| 7,727,264 B2 | 6/2010 | Orbay et al. |
| 7,731,718 B2 | 6/2010 | Schwammberger et al. |
| 8,632,573 B2 | 1/2014 | Ellis et al. |
| 9,808,297 B2 | 11/2017 | Bernstein et al. |
| 2001/0011172 A1 | 8/2001 | Orbay et al. |
| 2002/0004660 A1 | 1/2002 | Henniges et al. |
| 2002/0032446 A1 | 3/2002 | Orbay |
| 2002/0055741 A1 | 5/2002 | Schlapfer et al. |
| 2002/0128654 A1 | 9/2002 | Steger et al. |
| 2002/0143336 A1 | 10/2002 | Hearn |
| 2002/0143337 A1 | 10/2002 | Orbay et al. |
| 2002/0143338 A1 | 10/2002 | Orbay et al. |
| 2002/0147453 A1 | 10/2002 | Gambale |
| 2002/0151899 A1 | 10/2002 | Bailey et al. |
| 2002/0156474 A1 | 10/2002 | Wack et al. |
| 2002/0177852 A1 | 11/2002 | Chervitz et al. |
| 2002/0183752 A1 | 12/2002 | Steiner et al. |
| 2003/0040748 A1 | 2/2003 | Aikins et al. |
| 2003/0055429 A1 | 3/2003 | Ip et al. |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0127904 A1 | 7/2004 | Konieczynski et al. |
| 2004/0153073 A1 | 8/2004 | Orbay |
| 2004/0186472 A1 | 9/2004 | Lewis et al. |
| 2004/0193164 A1 | 9/2004 | Orbay |
| 2004/0193165 A1 | 9/2004 | Orbay |
| 2004/0220566 A1 | 11/2004 | Bray |
| 2004/0260291 A1 | 12/2004 | Jensen |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0015089 A1 | 1/2005 | Young et al. |
| 2005/0015090 A1 | 1/2005 | Silverman |
| 2005/0049593 A1 | 3/2005 | Duong et al. |
| 2005/0065520 A1 | 3/2005 | Orbay |
| 2005/0065522 A1 | 3/2005 | Orbay |
| 2005/0065523 A1 | 3/2005 | Orbay |
| 2005/0065524 A1 | 3/2005 | Orbay |
| 2005/0065528 A1 | 3/2005 | Orbay |
| 2005/0070902 A1 | 3/2005 | Medoff |
| 2005/0085818 A1 | 4/2005 | Huebner |
| 2005/0085819 A1* | 4/2005 | Ellis ............... A61B 17/8076 606/71 |
| 2005/0131413 A1 | 6/2005 | O'Driscoll et al. |
| 2005/0159747 A1 | 7/2005 | Orbay |
| 2005/0165395 A1 | 7/2005 | Orbay et al. |
| 2005/0165400 A1 | 7/2005 | Fernandez |
| 2005/0171544 A1 | 8/2005 | Falkner, Jr. |
| 2005/0182405 A1 | 8/2005 | Orbay et al. |

(56) References Cited

U.S. PATENT DOCUMENTS

| | | |
|---|---|---|
| 2005/0182406 A1 | 8/2005 | Orbay et al. |
| 2005/0187551 A1 | 8/2005 | Orbay et al. |
| 2005/0192578 A1 | 9/2005 | Horst |
| 2005/0234458 A1 | 10/2005 | Huebner |
| 2006/0058796 A1 | 3/2006 | Hartdegen et al. |
| 2006/0085000 A1 | 4/2006 | Mohr et al. |
| 2006/0100623 A1 | 5/2006 | Pennig |
| 2006/0150986 A1* | 7/2006 | Roue ............... A61F 2/04 128/848 |
| 2007/0043367 A1 | 2/2007 | Lawrie |
| 2007/0043368 A1 | 2/2007 | Lawrie et al. |
| 2007/0083202 A1 | 4/2007 | Eli Running et al. |
| 2007/0123883 A1 | 5/2007 | Ellis et al. |
| 2007/0185493 A1 | 8/2007 | Feibel et al. |
| 2007/0213727 A1 | 9/2007 | Bottlang et al. |
| 2008/0178712 A1 | 7/2008 | Brown |
| 2008/0319443 A1 | 12/2008 | Focht et al. |
| 2009/0036930 A1 | 2/2009 | Allison |
| 2009/0069812 A1 | 3/2009 | Gillard et al. |
| 2009/0118768 A1 | 5/2009 | Sixto, Jr. et al. |
| 2009/0177240 A1 | 7/2009 | Perez |
| 2009/0259107 A1 | 10/2009 | Crenshaw et al. |
| 2010/0087822 A1 | 4/2010 | Groiso |
| 2010/0133316 A1 | 6/2010 | Lizee et al. |
| 2010/0234896 A1 | 9/2010 | Lorenz et al. |
| 2010/0274245 A1 | 10/2010 | Gonzalez-Hernandez |
| 2010/0331844 A1 | 12/2010 | Ellis et al. |
| 2011/0022090 A1 | 1/2011 | Gordon et al. |
| 2011/0160730 A1 | 6/2011 | Schonhardt et al. |
| 2011/0218636 A1 | 9/2011 | Smith et al. |
| 2012/0016418 A1 | 1/2012 | Chin et al. |
| 2012/0209278 A1* | 8/2012 | Ries ............... A61B 17/158 606/96 |
| 2013/0090695 A1 | 4/2013 | Bernstein et al. |
| 2013/0197521 A1 | 8/2013 | Seykora et al. |
| 2014/0128923 A1 | 5/2014 | Ellis et al. |

FOREIGN PATENT DOCUMENTS

| | | |
|---|---|---|
| CH | 576249 A5 | 6/1976 |
| CH | 611147 A5 | 5/1979 |
| CN | 201755247 U | 3/2011 |
| DE | 251430 A1 | 11/1975 |
| DE | 3808937 A1 | 10/1989 |
| DE | 9115341 A1 | 2/1992 |
| DE | 4201531 A1 | 7/1993 |
| DE | 4343117 A1 | 6/1995 |
| EP | 0029752 B1 | 4/1983 |
| EP | 0094039 A1 | 11/1983 |
| EP | 0179695 A1 | 4/1986 |
| EP | 0053999 B1 | 3/1987 |
| EP | 0410309 A1 | 1/1991 |
| EP | 0415837 A2 | 3/1991 |
| EP | 0362049 B1 | 5/1992 |
| EP | 0561295 A1 | 9/1993 |
| EP | 0471418 B1 | 6/1995 |
| EP | 0852128 A1 | 7/1998 |
| EP | 0955011 A1 | 10/1999 |
| EP | 0955011 A1 | 11/1999 |
| EP | 1250892 A2 | 10/2002 |
| EP | 1667590 B1 | 11/2012 |
| EP | 2760354 | 8/2014 |
| FR | 742618 A | 3/1933 |
| FR | 2211851 A5 | 7/1974 |
| FR | 2254298 A1 | 8/1975 |
| FR | 2367479 A1 | 5/1978 |
| FR | 2405705 A1 | 5/1979 |
| FR | 2405706 A1 | 5/1979 |
| FR | 2406429 A1 | 5/1979 |
| FR | 2416683 A1 | 9/1979 |
| FR | 2472373 A1 | 7/1981 |
| FR | 2674118 A1 | 9/1992 |
| GB | 2245498 A | 1/1992 |
| GB | 2331244 A | 5/1999 |
| GB | 2435429 A | 8/2007 |
| GB | 2423935 B | 10/2007 |
| GB | 2450247 B | 1/2010 |
| GB | 2509668 A | 7/2014 |
| JP | S64-032855 A | 2/1989 |
| JP | 2211141 A | 8/1990 |
| JP | 312145 A | 1/1991 |
| JP | H05-146502 A | 6/1993 |
| JP | H063551 Y2 | 2/1994 |
| JP | 2002542875 A | 12/2002 |
| JP | 2007503885 A | 3/2007 |
| JP | 4808621 B2 | 8/2011 |
| JP | 5314074 B2 | 7/2013 |
| SU | 610518 A1 | 6/1978 |
| SU | 718097 A1 | 2/1980 |
| SU | 862937 A1 | 9/1981 |
| SU | 874044 A1 | 10/1981 |
| SU | 897233 A1 | 1/1982 |
| SU | 921553 A1 | 4/1982 |
| SU | 1049054 A | 10/1983 |
| SU | 1130332 A | 12/1984 |
| SU | 1192806 A | 11/1985 |
| SU | 1223901 A1 | 4/1986 |
| SU | 1225556 A | 4/1986 |
| SU | 1544406 A1 | 2/1990 |
| SU | 1630804 A1 | 2/1991 |
| SU | 1644932 A1 | 4/1991 |
| SU | 1683724 A1 | 10/1991 |
| SU | 1711859 A1 | 2/1992 |
| SU | 1734715 A1 | 5/1992 |
| WO | 8201645 A1 | 5/1982 |
| WO | 8702572 A1 | 5/1987 |
| WO | 8803781 A1 | 6/1988 |
| WO | 9505782 A1 | 3/1995 |
| WO | 9629948 A1 | 10/1996 |
| WO | 9747251 A1 | 12/1997 |
| WO | 9922089 A1 | 5/1999 |
| WO | 0062693 A1 | 10/2000 |
| WO | 0121083 A1 | 3/2001 |
| WO | 0162136 A2 | 8/2001 |
| WO | 0203882 A2 | 1/2002 |
| WO | 03105712 A2 | 12/2003 |
| WO | 2005020800 A2 | 3/2005 |
| WO | WO2007092813 A2 | 8/2007 |
| WO | 2007109436 A2 | 9/2007 |
| WO | 2009086402 A1 | 7/2009 |
| WO | 2013049849 A2 | 4/2013 |
| WO | 2013113015 A1 | 8/2013 |

OTHER PUBLICATIONS

Ring et al., "Prospective Multicenter Trial of a Plate for Dorsal Fixation of Distal Radius Fractures", The Journal of Hand Surgery, vol. 22A, No. 5, pp. 777-784, Sep. 1997.

Avanta Orthopaedics, SCS/V Distal Radius Plate Volar brochure, 1998.

Oyarzun et al., "Use of 3.5mm Acetabular Reconstruction Plates for Internal Fixation of Flail Chest Injuries", Section of Cardiothoracic Surgery, pp. 1471-1474, 1998.

Voggenreiter et al., "Operative Chest Wall Stabilization in Flail Chest—Outcomes of Patients With or Without Pulmonary Contusion", American College of Surgeons, pp. 130-138, 1998.

Kolodziej et al., "Biomechanical Evaluation of the Schuhli Nut", Clinical Orthopaedics and Related Research, vol. 347, pp. 79-85, Feb. 1998.

Acumed Inc., Congruent Distal Radius Plate System description, Mar. 4, 1998.

Trumble et al., "Intra-Articular Fractures of the Distal Aspect of the Radius", Journal of Bone and Joint Surgery, vol. 80A, No. 4, pp. 582-600, Apr. 1998.

Kambouroglou etal., "Complications of the AO/ASIF Titanium Distal Radius Plate System (Π Plate) in Internal Fixation of the Distal Radius: A Brief Report", Journal of Hand Surgery, vol. 23A, No. 4, pp. 737-741, Jul. 1998.

DePuy Ace, TiMAX Pe.R.I. Small Fragment Upper Extremity description pages, 1999.

(56) References Cited

OTHER PUBLICATIONS

Palmer etal., "The Use of Interlocked 'Customised' Blade Plates in the Treatment of Metaphyseal Fractures in Patients with Poor Bone Stock", Injury, Int. J. Care Injured, vol. 31, pp. 187-191, 1999.
Synthes (USA), The Distal Radius Plate Instrument and Implant Set technique guide, 1999.
Tatsumi et al., "Bioabsorable Poly-L-Lactide Costal Coaptation Pins and Their Clinical Application in Thoroacotomy", Original Articles: General Thoracic. pp. 765-768, 1999.
Morgan et al., "Salvage of Tibial Pilon Fractures Using Fusion of the Ankle with a 90° Cannulated Blade Plate: A Preliminary Report", Foot & Ankle International, vol. 20, No. 6, pp. 375-378, Jun. 1999.
Nunley et al., "Delayed Rupture of the Flexor Pollicis Longus Tendon After Inappropriate Placement of the Π Plate on the Volar Surface of the Distal Radius", Journal of Hand Surgery, vol. 24, No. 6, pp. 1279-1280, Nov. 1999.
Toby, Scaphoid Protocols Using the Acutrak® Bone Screw System brochure, published by Acumed, Inc., Dec. 7, 1999.
Biomet Orthopedics, Inc., Supracondylar Cable Plate brochure, 2000.
U.K. Intellectual Property Office, "Search and Examination Report Under Sections 17 and 18(3)" in connection with related U.K. Application No. GB1407548.5, dated Nov. 3, 2017, 5 pgs.
U.K. Intellectual Property Office, "Combined Search and Examination Report Under Sections 17 and 18(3)" in connection with related U.K. Application No. GB1802881.1, dated May 2, 2018, 7 pgs.
European Patent Office, "Communication Pursuant to Rule 164(1) EPC" in connection with related European Patent App. No. 12836708. 3, dated Jul. 22, 2015, 7 pgs.
Esser, Proximal Humerus Fractures operative technique, undated.
Kinetics Medical Incorporated, Spider™ and Mini-Spider™ Limited Wrist Fusion System brochure, undated.
Kinetics Medical Incorporated, Spider™ Limited Wrist Fusion System brochure, undated.
US Implants, Val Plate description page, undated.
Zimmer, Inc., ECT Internal Fracture Fixation brochure, undated.
Zimmer, Inc., ECT Internal Fracture Fixation System order information brochure, undated.
Zimmer, Inc., NexGen Osteotomy System (OS) surgical technique brochure, undated.
U.S. Receiving Office of WIPO, International Search Report and Written Opinion of the International Searching Authority regarding PCT Patent Application No. PCT/US2012/058360, dated Feb. 26, 2013, 26 pages.
Engel et al., Operative Chest Wall Fixation with Osteosynthesis Plates, The Journal of Trauma, Injury, Infection and Critical Care, vol. 58, No. 1, pp. 181-186, 2005.
United States Patent and Trademark Office, Office Action for U.S. Appl. No. 13/633,024, dated Sep. 18, 2014, 13 pages.
European Patent Office, "Extended European Search Report" in connection with related European Patent Application No. 12836708. 3, dated Nov. 10, 2015, 14 pages.
Japanese Patent Office, "Notice of Reasons for Rejection" in connection with related Japanese Patent Application No. 2014-533484, dated Aug. 29, 2016, 4 pages.
Japanese Patent Office, "Notice of Reasons for Rejection" in connection with related Japanese Patent Application No. 2014-533484, dated May 8, 2017, 6 pages.
European Patent Office, "Communication Pursuant to Article 94(3)EPC," in connection with related European Patent Application No. 12836708.3, dated Mar. 2, 2018, 4 pages.
Cacchione et al., "Painful Nonunion of Multiple Rib Fractures Managed by Operative Stabilization", The Journal of Trauma, Injury, Infection and Critical Care, vol. 48, No. 2, pp. 319-321, 2000.
Peine et al., "Comparison of Three Different Plating Techniques for the Dorsum of the Distal Radius: A Biomechanical Study", Journal of Hand Surgery, vol. 25A, No. 1, pp. 29-33, Jan. 2000.

Young, "Outcome Following Nonoperative Treatment of Displaced Distal Radius Fractures in Low-Demand Patients Older Than 60 Years", Journal of Hand Surgery, vol. 25A, No. 1, pp. 19-28, Jan. 2000.
Putnam et al., "Distal Radial Metaphyseal Forces in an Extrinsic Grip Model: Implications for Postfracture Rehabilitation", Journal of Hand Surgery, vol. 25A, No. 3, pp. 469-475, May 2000.
Surfix Technologies, Single Units Osteosynthesis brochure, Sep. 2000.
Lardinois et al., "Pulmonary Function Testing After Operative Stabilisation of the Chest Wall for Flail Chest", European Journal of Cardio-thoracic Surgery (2001) 20:496-501.
Ng et al., "Operative Stabilisation of Painful Non-united Multiple Rib Fractures", Injury (2001) 32:637-639.
Synthes (USA), Titanium Distal Radius Plates description page, 2001.
Wright Medical Technology, Inc., Locon-T Distal Radius Plating System case study and surgical method, 2001.
Trimed Inc., TriMed Wrist Fixation System internet description pages, 2001.
Slater et al., "Operative Stabilization of Flail Chest Six Years After Injury", Annals of Thoracic Surgery Aug. 2001: 600-601.
Sanchez-Sotelo et al., "Principle-Based Internal Fixation of Distal Humerus Fractures, Techniques in Hand & Upper Extremity Surgery", vol. 5, No. 4, pp. 179-187, Dec. 2001.
Abel et al., "An Axially Mobile Plate for Fracture Fixation", Internal Fixation in Osteoporotic Bone, pp. 279-283, 2002.
An, Y.H., Internal Fixation in Osteoporotic Bone, pp. 82-83, 2002.
Konrath et al., "Open Reduction and Internal Fixation of Unstable Distal Radius Fractures: Results Using the Trimed Fixation System", Journal of Orthopaedic Trauma, vol. 16, No. 8, pp. 578-585, 2002.
Mizuho Co., Ltd., Jplate Diaphysis Plates for Japanese brochure, 2002.
Synthes (USA), 3.5 mm LCP™ Proximal Humerus Plate technique guide, 2002.
Tanaka et al., "Surgical Stabilization or Internal Pneumatic Stabilization? A Prospective Randomized Study of Management of Severe Flail Chest Patients", Journal of Trauma (2002) 52:727-732.
Sing et al., "Thoracoscopic Resection of Painful Multiple Rib Fractures: Case Report" The Journal of Trauma, vol. 52, No. 2, pp. 391-392, 2002.
Tornetta, Distal Radius Fracture, Journal of Orthopaedic Trauma, vol. 16, No. 8, pp. 608-611, 2002.
Wright Medical Technology, Inc., Locon-T Distal Radius Plating System brochure, 2002.
Zimmer, Inc., Periarticular Plating System brochure, 2002.
Acumed Inc., Congruent Plate System—The Mayo Clinic Congruent Elbow Plates brochure, May 7, 2002.
Acumed Inc., Modular Hand System brochure, Aug. 2002.
Acumed Inc., Modular Hand System brochure, Sep. 2002.
Harvey et al., "The Use of a Locking Custom Contoured Blade Plate for Peri-Nonunions", Injury, Int. J. Care Injured, vol. 34, pp. 111-116, 2003.
Chin et al., "Salvage of Distal Tibia Metaphyseal Nonunions With the 90° Cannulated Blade Plate", Clinical Orthopaedics and Related Research, No. 409, pp. 241-249, 2003.
Hooker et al., Fixation of Unstable Fractures of the Volar Rim of the Distal Radius with a Volar Buttress Pin®, 2003.
Rozental et al., Functional Outcome and Complications Following Two Types of Dorsal Plating for Unstable Fractures of the Distal Part of the Radius, Journal of Bone and Joing Surgery, vol. 85, No. 10, pp. 1956-1960, 2003 (abstract only).
Osada et al.., "Comparison of Different Distal Radius Dorsal and Volar Fracture Fixation Plates: A Biomechanical Study", Journal of Hand Surgery, vol. 28A, No. 1, pp. 94-104, Jan. 2003.
Turner et al., Tendon Function and Morphology Related to Material and Design of Plates For Distal Radius Fracture Fixation: Canine Forelimb Model, Orthopaedic Research Society, Feb. 2003.
Erothitan Titanimplantate AG, Titanium Wire Plate Osteosynthesis System According to Dr. Gahr internet printout, print date Feb. 6, 2003.

(56) References Cited

OTHER PUBLICATIONS

Simic, "Fractures of the Distal Aspect of the Radius: Changes in Treatment Over the Past Two Decades", Journal of Bone and Joint Surgery, vol. 85-A, No. 3, pp. 552-564, Mar. 2003.
Leung et al., "Palmar Plate Fixation of AO Type C2 Fracture of Distal Radius Using a Locking Compression Plate—A Biomechanical Study in a Cadaveric Model", Journal of Hand Surgery, vol. 28B, No. 3, pp. 263-266, Jun. 2003.
Martin GmbH & Co. KG, Bilder internet printout, print date Sep. 5, 2003.
Mayberry, "Absorbable Plates for Rib Fracture Repair: Preliminary Experience", Journal of Trauma Injury, Infection and Critical Care. vol. 55, No. 5, pp. 835-839, Nov. 2003.
Moore et al., Clinically Oriented Anatomy, Fourth Edition, pp. 70-71, 2004.
Orthocopia, LLC, Synthes Volar Distal Radius Locking Plate internet description page, 2004.
Ruch et al., "Results of Palmar Plating of the Lunate Facet Combined with External Fixation for the Treatment of High-Energy Compression Fractures of the Distal Radius", J. Orthop. Trauma, Vo. 18, No. 1, pp. 28-33, Jan. 2004.
Sanatmetal, Rib Securing Clamped Plate, internet printout, Sep. 2004 <http://www.sanatmetal.hu/catalog/pict/1_5_89a_1.jpg>.
Zespol Bone Plates, in Mikromed—Catalogue 2004 (Nov. 2004), original website <http://www.mikromed.pl/katalog/Main/main_eng.htm> and < http://www.mikromed.pl/katalog/zespol_eng/plytki.htm >, viewable via the Internet Archive Wayback Machine < http://replay.waybackmachine.org/ 20070830023439/http://www.mikromed.pl/katalog/zespol_eng/plytki.htm >.
Zespol Bone Screws, in Mikromed—Catalogue 2004 (Nov. 2004), original website <http://www.mikromed.pl/katalog/Main/main_eng.htm> and < http://www.mikromed.pl/katalog/zespol_eng/wkrety.htm >, viewable via the Internet Archive Wayback Machine < http://replay.waybackmachine.org/ 20050226124226/http://www.mikromed.pl/katalog/zespol_eng/wkrety.htm >.
DVO Extremity Solutions, MIfx Dorsal IM Plate, brochure, Sep. 2005.
Stryker SmartLock Locking Screw Technology, advertisement, The Journal of Hand Surgery, vol. 30A, No. 1, Jan. 2005.
Legacy Biomechanics Laboratory, Applied Research, Jan. 2006, original website <http://www.biomechresearch.org/sling.html>, viewable via the Internet Archive Wayback Machine <http://replay.waybackmachine.org/ 20060320091922/http://www.biomechresearch.org/sling.html>.
Osteomed, images of Resorable Plates, Feb. 2006 <http://www.osteomedcorp.com/images/library/resorbfixation.gif>.
AO Foundation, TK System: Innovations, Dec. 2011.
Acromio-Clavicular Plates description page, author and date unknown.
Codman & Shurtleff, Inc., Zuelzer Hook Plates description page, p. 808, undated.
Esser Complete Distal Radius Plate System, undated.
Depuy, Inc., McBride S.M.O. Stainless Steel Bone Plates brochure, 1943.
Vitallium, Bone Plates brochure, Mar. 1948.
Moore et al., "Operative stabilization of nonpenetrating chest injuries", The Journal of Thoracic and Cardiovascular Surgery, vol. 70, No. 4, pp. 619-630, 1975.
Tarazona et al., "Surgical stabilization of traumatic flail chest", pp. 521-527, 1975.
Thomas et al., "Operative stabilization for flail chest after blunt trauma", The Journal of Thoracic and Cardiovascular Surgery, vol. 75, No. 6, pp. 793-801, 1978.
Trunkey, "Chest Wall Injuries", Cerviothoracic Trauma, vol. 3. pp. 129-149, 1986.
Klein et al., "Rib Fracture Healing after Osteosynthesis with Wire Mesh Titanium and Screws: A Histological Study in Sheep", Eur Surg Res, vol. 21 pp. 347-354, 1989.
Techmedica, Inc., The Arnett-TMP* Titanium Miniplating System brochure, 1989.
Haasler, "Open Fixation of Flail Chest After Blunt Trauma", The Society of Thoracic Surgeons, pp. 993-995, 1990.
Howmedica Inc., Dupont Distal Humeral Plates brochure, 1990.
Landreneau et al., "Strut Fixation of an Extensive Flail Chest", The Society of Thoracic Surgeons, pp. 473-475, 1991.
Synthes (USA), Biological Plating: A New Concept to Foster Bone Healing, 1991.
Synthes, CMR Matrix: MatrixRIB. Stable fixation of normal and asteoporotic ribs. Techinque Guide, 1991.
Techmedica, Inc., Techmedica Bioengineers Keep Tabs on Your Needs brochure, 1991.
Ace Medical Company, Ace 4.5/5.0 mm Titanium Cannulated Screw and Reconstruction Plate System simplified fracture fixation brochure, 1992.
Ace Medical Company, Ace 4.5/5.0 mm Titanium Cannulated Screw and Reconstruction Plate System surgical technique brochure, 1992.
Beaupre et al., "A Comparison of Unicortical and Bicortical End Screw Attachment of Fracture Fixation Plates", Journal of Orthopaedic Trauma, vol. 6, No. 3, pp. 294-300, 1992.
Ace Medical Company, Ace Titanium 3.5/4.0 mm Screw and Plate System with the Ace 3.5 mm Universal Ribbon CT/MRI compatible fixation brochure, 1994.
Esser, "Treatment of Three- and Four-Part Fractures of the Proximal Humerus with a Modified Cloverleaf Plate", Journal of Orthopaedic Trauma, vol. 8, No. 1, pp. 15-22, 1994.
Amadio, "Open Reduction of Intra-Articular Fractures of the Distal Radius", Fractures of the Distal Radius, pp. 193-202, 1995.
Ducloyer, "Treatment by Plates of Anteriorly Displaced Distal Radial Fractures", Fractures of the Distal Radius, pp. 148-152, 1995.
Gesensway et al., "Design and Biomechanics of a Plate for the Distal Radius", Journal of Hand Surgery, vol. 20, No. 6, pp. 1021-1027, 1995 (abstract only provided).
Jupiter et al., "Management of Comminuted Distal Radial Fractures", Fractures of the Distal Radius, pp. 167-183, 1995.
Waldemar Link GmbH & Co., May Anatomical Bone Plates: Plates, Bone Screws and Instruments brochure, pp. 3-4 and 10-15, 1995.
Zimmer, Inc., Forte Distal Radial Plate System brochure, 1995.
Ace Medical Company, The Ace Symmetry Titanium Upper Extremity Plates new product release brochure, 1996.
Ace Medical Company, Ace Symmetry Titanium Upper Extremity Plates surgical technique brochure, 1996.
Fernandez et al., Fractures of the Distal Radius: A Practical Approach to Management, pp. 103-188, 1996.
Avanta Orthopaedics, SCS/D Distal Radius Plate System brochure, 1997.
Fitoussi et al., "Treatment of Displaced Intra-Articular Fractures of the Distal End of the Radius With Plates", The Journal of Bone and Joint Surgery, vol. 79, No. 9, pp. 1303-1312, 1997 (abstract only provided).
Synthes (USA), The Titanium Distal Radius Plate, technique guide, 1997.
Trimed Inc., TriMed Wrist Fixation System brochure, 1997.
Synthes, Small Titanium Plates overview page, p. 2a-33, Mar. 1997.

\* cited by examiner

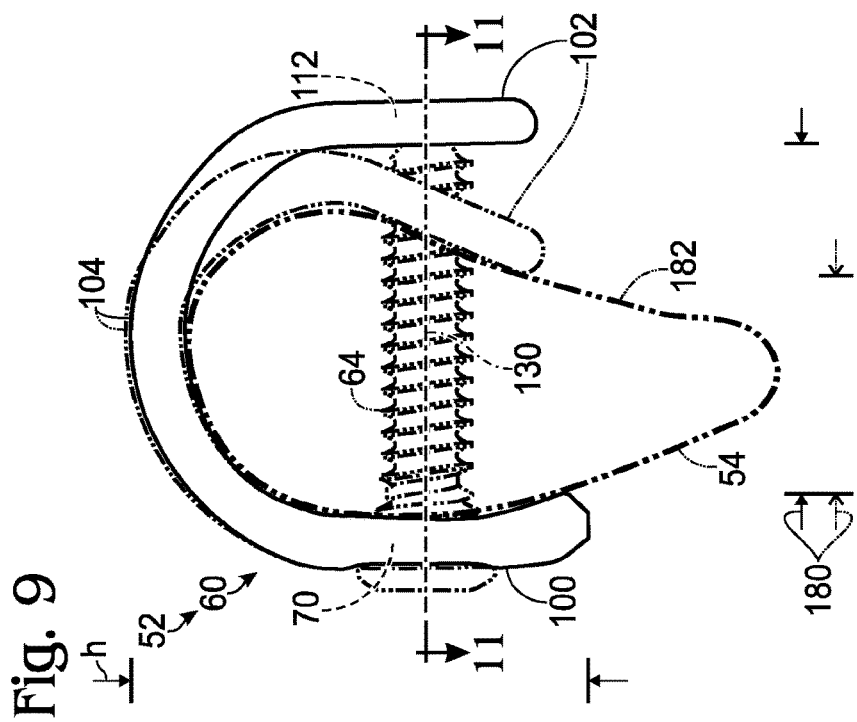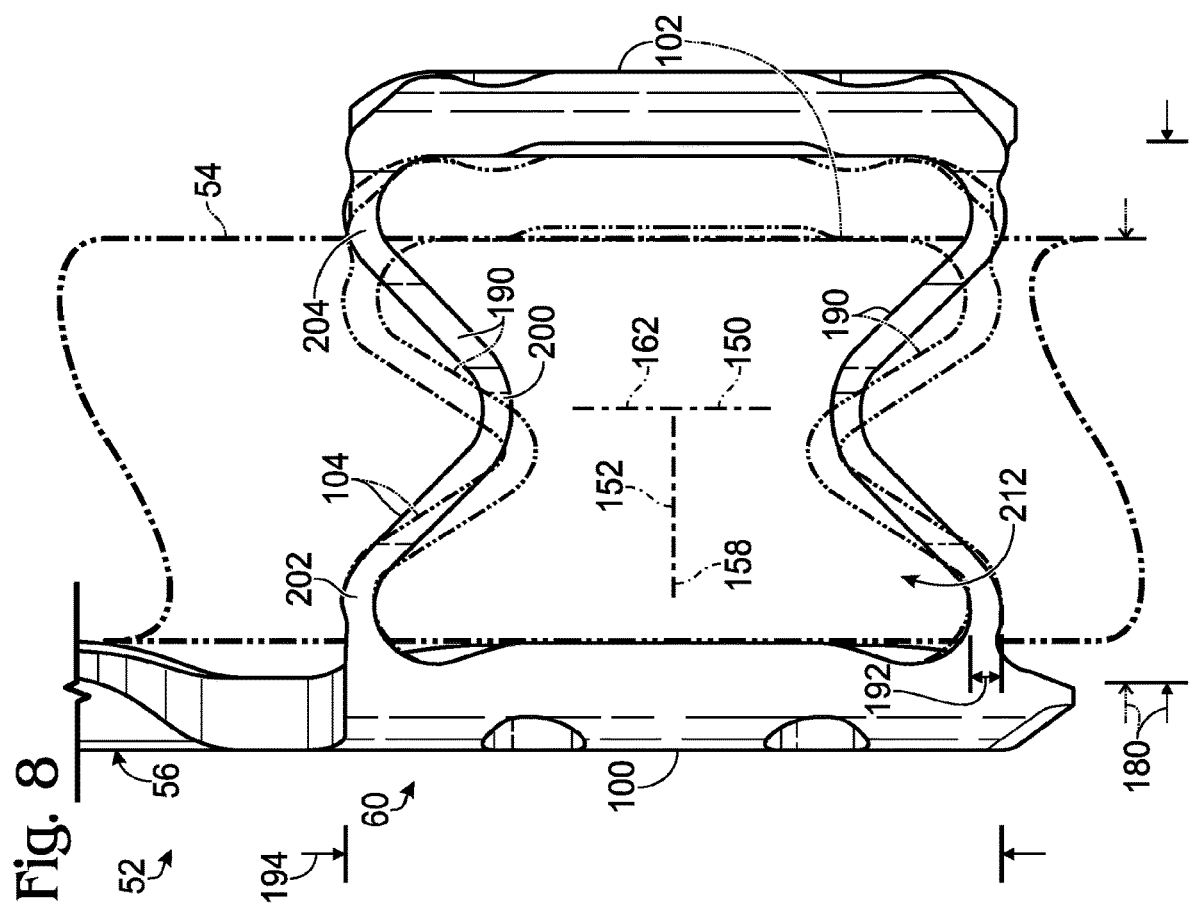

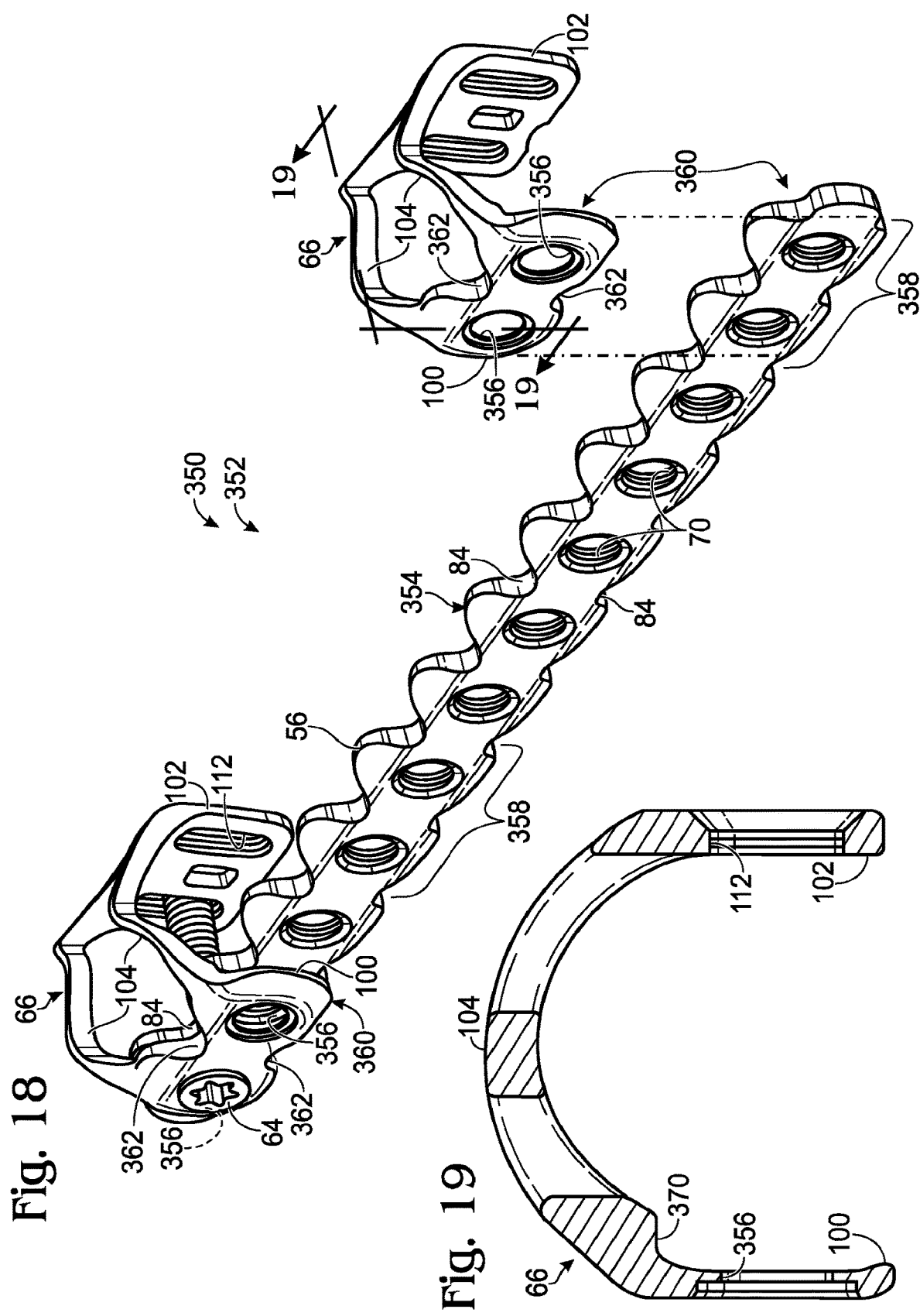

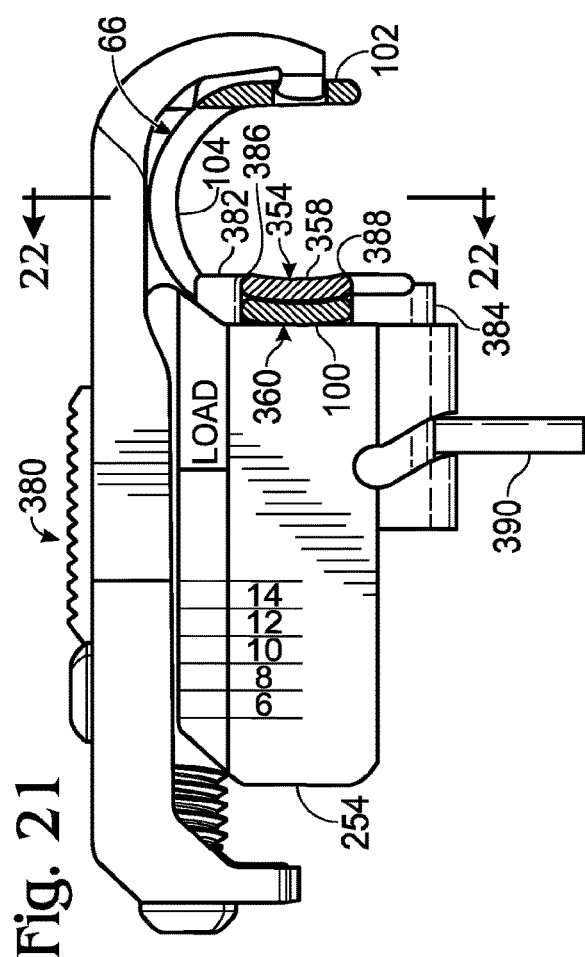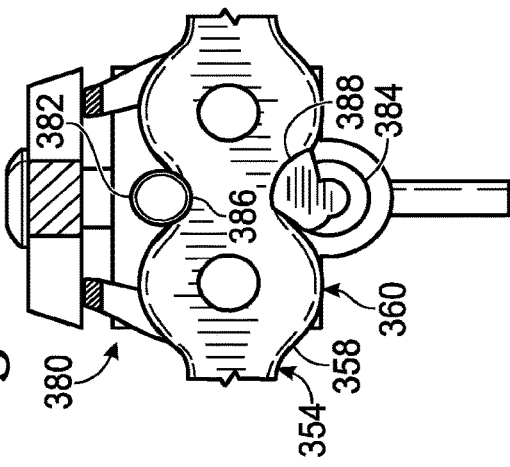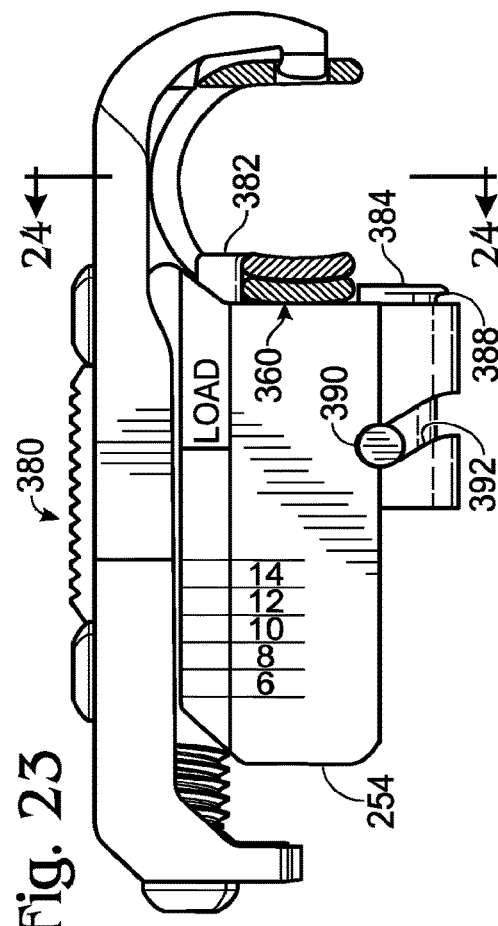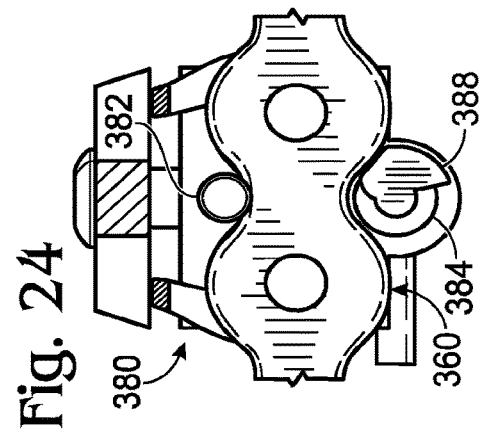

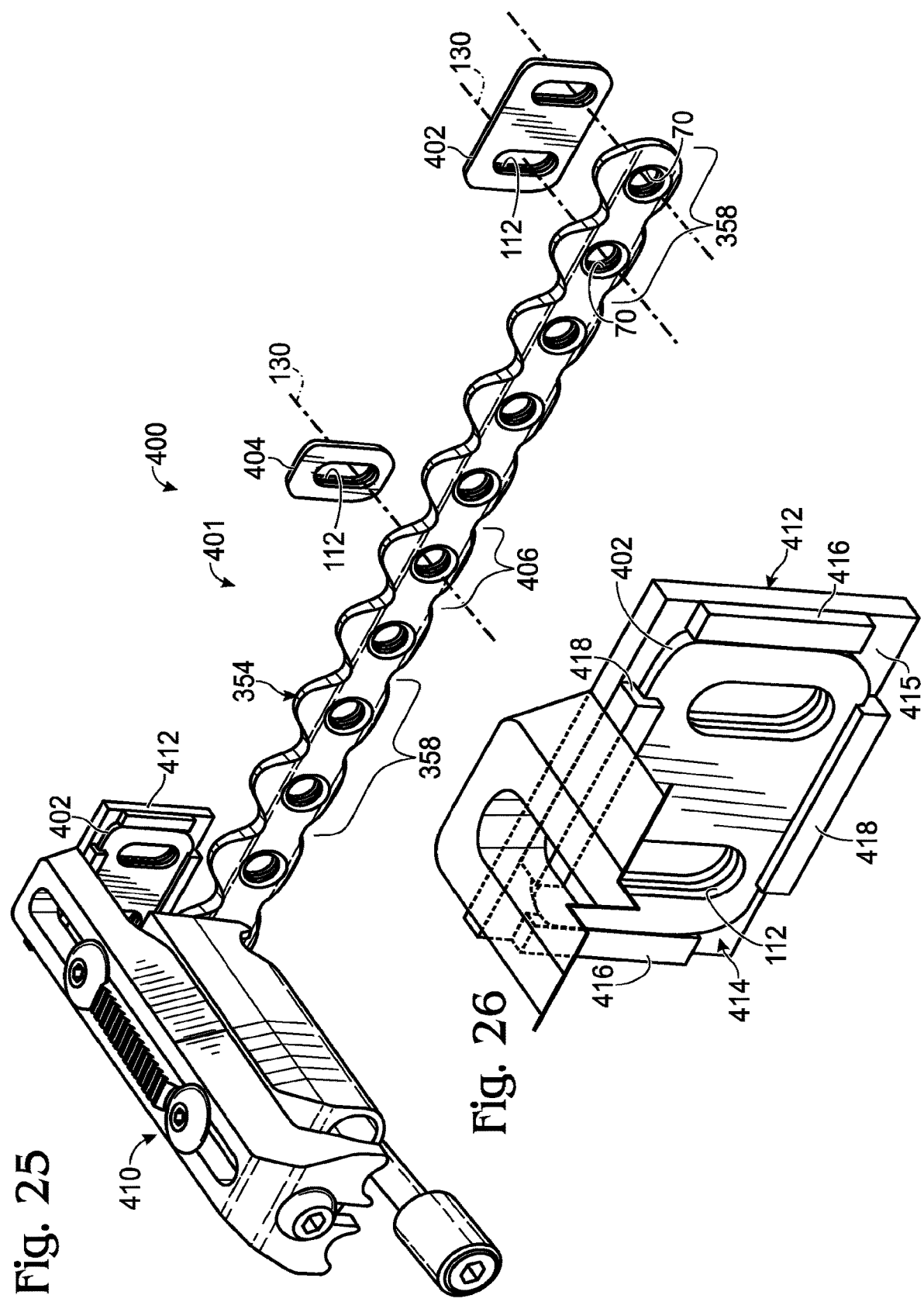

BONE FIXATION SYSTEM WITH OPPOSED MOUNTING PORTIONS

CROSS-REFERENCES TO PRIORITY APPLICATIONS

This application is a continuation of U.S. application Ser. No. 15/804,638, filed Nov. 6, 2017, which is a continuation of U.S. patent application Ser. No. 14/207,058, filed Mar. 12, 2014, now U.S. Pat. No. 9,808,297.

U.S. patent application Ser. No. 14/207,058 is a continuation-in-part of the following U.S. patent applications: Ser. No. 12/903,024, filed Oct. 12, 2010, now U.S. Pat. No. 8,679,122; Ser. No. 13/287,955, filed Nov. 2, 2011, now abandoned; Ser. No. 13/633,024, filed Oct. 1, 2012, now U.S. Pat. No. 9,775,657; Ser. No. 13/752,188, filed Jan. 28, 2013, now U.S. Pat. No. 9,237,910; Ser. No. 13/874,171, filed Apr. 30, 2013, now U.S. Pat. No. 9,241,748; and Ser. No. 13/942,459, filed Jul. 15, 2013, now U.S. Pat. No. 9,237,913.

U.S. patent application Ser. No. 12/903,024, in turn, is based upon and claims the benefit under 35 U.S.C. § 119(e) of U.S. Provisional Patent Application Ser. No. 61/250,389, filed Oct. 9, 2009.

U.S. patent application Ser. No. 13/287,955, in turn, is based upon and claims the benefit under 35 U.S.C. § 119(e) of U.S. Provisional Patent Application Ser. No. 61/409,415, filed Nov. 2, 2010.

U.S. patent application Ser. No. 13/633,024, in turn, is based upon and claims the benefit under 35 U.S.C. § 119(e) of U.S. Provisional Patent Application Ser. No. 61/542,046, filed Sep. 30, 2011.

U.S. patent application Ser. No. 13/752,188, in turn, is based upon and claims the benefit under 35 U.S.C. § 119(e) of U.S. Provisional Patent Application Ser. No. 61/590,955, filed Jan. 26, 2012.

U.S. patent application Ser. No. 13/874,171, in turn, is based upon and claims the benefit under 35 U.S.C. § 119(e) of U.S. Provisional Patent Application Ser. No. 61/640,486, filed Apr. 30, 2012; and U.S. Provisional Patent Application Ser. No. 61/641,703, filed May 2, 2012.

U.S. patent application Ser. No. 13/942,459, in turn, is a continuation of U.S. patent application Ser. No. 12/249,252, filed Oct. 10, 2008, now U.S. Pat. No. 8,486,114.

Each of these priority applications is incorporated herein by reference in its entirety for all purposes.

INTRODUCTION

The rib cage, or thoracic cage, is composed of bone and cartilage that surround the chest cavity and organs therein, such as the heart and the lungs. In humans, the rib cage typically consists of 24 ribs, twelve thoracic vertebrae, the sternum (or breastbone), and the costal cartilages. The ribs articulate with the thoracic vertebrae posteriorly and, with the exception of the bottom two pairs of ribs (the floating ribs), are connected to the sternum anteriorly using the costal cartilages.

Trauma to the torso can result in fracture of one or more ribs. Frequently, a simple rib fracture is nondisplaced, so that reduction and/or internal fixation of the fracture may not be required. However, in cases of more severe trauma to the chest, a single rib may be fractured more severely and/or multiple rib fractures may occur. With multiple rib fractures, a section of the thoracic wall may become detached from the rest of the chest wall, a condition known to medical practitioners as "flail chest." Flail chest often results in paradoxical motion of the injured area, in which the freely floating thoracic section is drawn in during inspiration, and pushed out during expiration. This condition may result in severe respiratory distress, possibly requiring the patient to be sedated and/or intubated during early stages of healing. Fixing single or multiple rib fractures internally may alleviate paradoxical motion, reduce pain, and/or help to prevent secondary injuries.

Internal fixation of a rib fracture may be accomplished using a bone plate to span the fracture. A bone plate suitable for treating fractured ribs may be custom-contoured (i.e., bent) by a surgeon to conform to a region of a rib spanning a fracture, and then fastened to the rib on both sides of the fracture. The plate thus fixes the rib to permit healing. The plate may be fastened to the fractured rib using fasteners, such as bone screws or wires, among others. Although bone screws can be used to secure bone plates to bone, rib bones have a thin cortex and are filled with spongy cancellous bone, neither of which can hold bone screws effectively, so the bone screws tend to pull out.

U.S. Pat. Nos. 7,635,365 and 7,695,501, both to Ellis et al., disclose a rib plating system that uses a U-shaped clip to prevent bone screws from backing out of the rib. The Ellis clip provides a revolutionary advancement in rib fixation. However, the system still could be improved, such as to make clip installation easier and more customizable, to provide a better fit of the clips on bones of different size and shape, to make fastener installation easier and/or more reliable, or the like.

Fitting the clips of Ellis closely onto a rib can be a challenge. Ribs have different sizes and shapes among patients and within the same patient. Even along the same rib, a clip sized to fit at one position of the rib may be too small or oversized at other positions.

The Ellis clips generally require a surgeon to have a set of clips of different size available at the start of a rib fixation surgery. The surgeon carefully measures the thickness of a rib at each position where a clip will be installed, and then chooses a suitable clip from the set that is closest in size for that rib position. This approach has a number of disadvantages: measuring the rib for each clip can be time-consuming and may be prone to errors; a relatively large set of clips, and especially bone plates with a pair of integral clips, may be necessary to accommodate all rib sizes accurately; and ribs vary in cross-sectional shape, which can make the fit imperfect even with the most careful measurement.

Therefore, an improved rib fixation system is needed.

SUMMARY

The present disclosure provides a system, including methods, apparatus, and kits, for bone fixation using a fixation device including a mounting portion and a fastener that attaches to the mounting portion. In some embodiments, the fixation device may include first and second mounting portions configured to be disposed across a bone from each other and secured with a fastener that extends from one of the mounting portions, through the bone, and to the other mounting portion. The system also may include a tool to facilitate installation of the fixation device.

BRIEF DESCRIPTION OF THE DRAWINGS

FIG. 3 is a cross-sectional view of a spanning portion of the fixation device of FIG. 1, taken generally along line 3-3 of FIG. 1.

FIG. 4 is a fragmentary front view of the fixation device of FIG. 2 taken generally along line 4-4 of FIG. 2 toward one of the clips, with only a front half of the clip shown.

FIG. 8 is a top view a clip of the fixation device of FIG. 2, with the clip received on a rib bone (in phantom) and illustrating the clip deformed from an initial configuration to a collapsed configuration (in phantom).

FIG. 9 is an end view of the clip and rib bone of FIG. 8 and illustrating the clip being deformed from the initial configuration to the collapsed configuration (in phantom) and secured to the rib bone in the collapsed configuration with an exemplary fastener (in phantom).

FIG. 18 is an isometric view of selected aspects of another exemplary bone fixation system with collapsible clips, particularly showing a fixation device having discrete clips and a plate member, with one clip attached to the plate member with a fastener and another clip exploded from the plate member, in accordance with aspects of the present disclosure.

FIG. 19 is a sectional view of one of the clips of FIG. 18, taken generally along line 19-19 of FIG. 18.

FIG. 21 is a side view of the tool of FIG. 20, with the tool attached to the clip and plate member, which are shown in a cross-sectional view taken orthogonal to the long axis of the plate member through aligned indentations of the clip and plate member.

FIG. 22 is a fragmentary, sectional view of the tool, clip, and plate member of FIG. 20, taken generally along line 22-22 of FIG. 21.

FIG. 23 is another view of the tool, clip, and plate member of FIG. 20, taken as in FIG. 21 but with the tool in a released configuration that permits removal of the clip and plate member from the jaws of the tool.

FIG. 24 is a fragmentary, sectional view of the tool, clip, and plate member of FIG. 20, taken as in FIG. 22 but with the tool in the released configuration.

FIG. 25 is an isometric view of selected aspects of another exemplary bone fixation system having mounting portions that opposingly engage bone, particularly showing a fixation device having a plate member and a plurality of discrete distal mounting portions, with the plate member and one of the distal mounting portions attached to an installation tool and with other distal mounting portions spaced from the plate member and aligned with selected apertures of the plate member, in accordance with aspects of the present disclosure.

FIG. 26 is a fragmentary view of the fixation system of FIG. 25, particularly showing a distal end region of the tool of FIG. 25 and the distal mounting portion that is attached to the tool.

DETAILED DESCRIPTION

Figure 1:
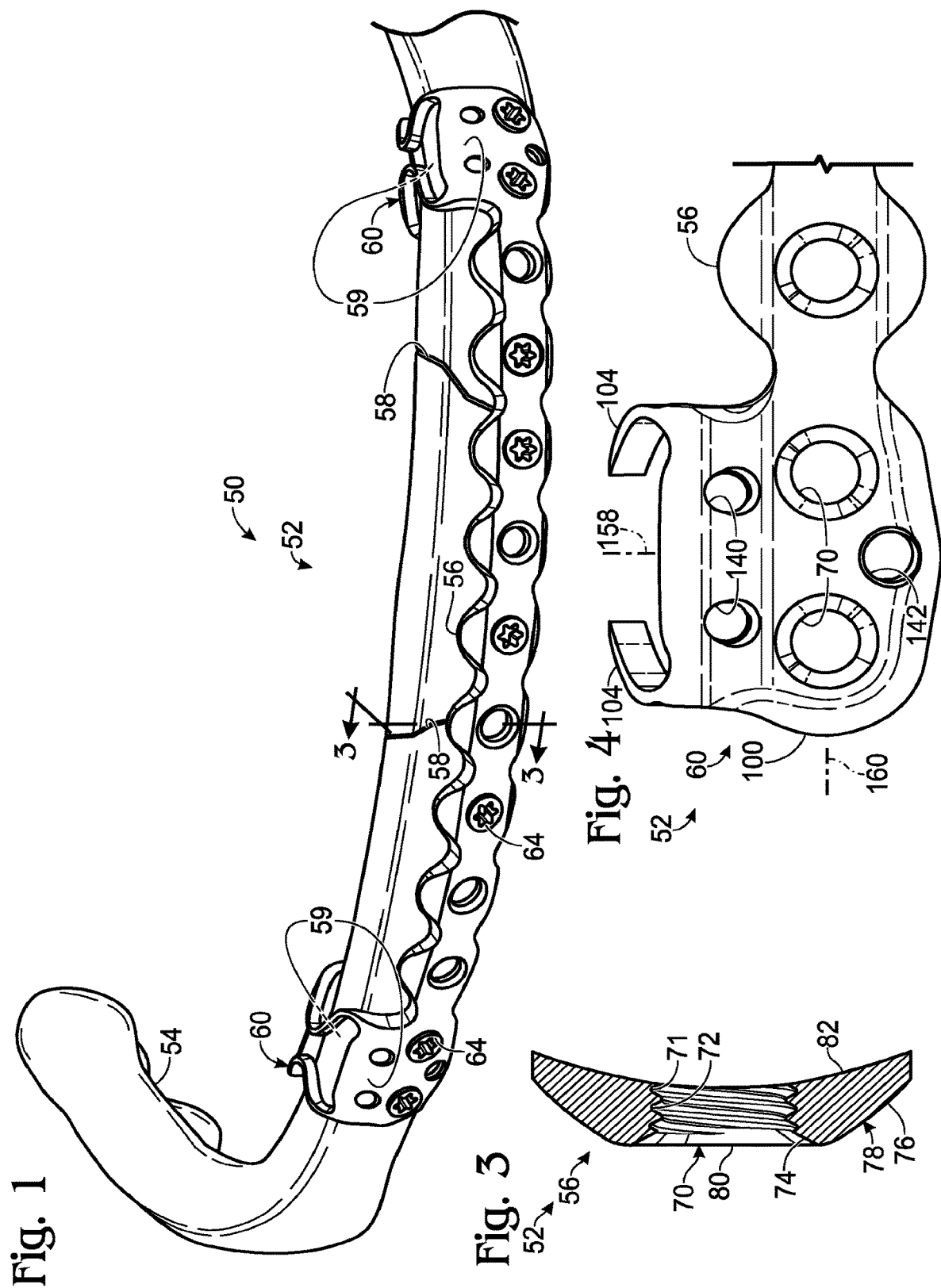
FIG. 1 is a front view of selected aspects of an exemplary bone fixation system including a fixation device having mounting portions provided by collapsible clips, with each clip collapsed on a fractured rib bone and secured to the rib bone with fasteners, in accordance with aspects of the present disclosure.

The present disclosure provides a system, including methods, apparatus, and kits, for bone fixation using a fixation device including a mounting portion and a fastener that attaches to the mounting portion. In some embodiments, the fixation device may include first and second mounting portions configured to be disposed across a bone from each other and secured with a fastener that extends from one of the mounting portions, through the bone, and to the other mounting portion. The system also may include a tool to facilitate installation of the fixation device.

An exemplary method of fixing bone is provided. In the method, a first mounting portion and a second mounting portion of a fixation device may be connected to an installation tool. The first mounting portion and the second mounting portion may be disposed across a bone from each other. The first and second mounting portions may be urged toward each other with jaws of the tool such that the tool is clamped to the bone. The first and second mounting portions may be secured to the bone with a fastener extending from a first aperture defined by the first mounting portion, through the bone, and into a second aperture defined by the second mounting portion.

An exemplary system for bone fixation is provided. The system may comprise a fixation device including a first mounting portion and a second mounting portion configured to be arranged across a bone from each other and respectively defining a first aperture and a second aperture. The system also may comprise an installation tool having jaws and being connectable to the first and second mounting portions such that the tool is operable to urge the first and second mounting portions toward each other with the jaws, to clamp the tool to the bone with the first aperture and the second aperture aligned with each other on a fastener-receiving axis.

Another exemplary bone fixation system is provided. The system may comprise a mounting portion configured to be disposed on bone and including a slot defining a long axis and having a first side wall region and a second side wall region disposed across the long axis from each other. The first side wall region may define a pair of ridges extending along the slot, with each ridge having a crest. A groove may be defined by the first side wall region between the crests. The system also may comprise a fastener having a thread and being advanceable into the slot to interchangeably attach the fastener to the slot in a first configuration having the thread disposed in the groove and in a second configuration having the thread opposingly flanking the pair of ridges and not disposed in the groove.

An exemplary device for bone fixation is provided. The device may comprise a clip member (interchangeably termed a clip) configured to be placed on bone and including a first mounting portion and a second mounting portion facing each other and respectively defining a first aperture and a second aperture aligned with each other on a same fastener-receiving axis. The mounting portions may be interconnected by one or more elongate web members forming a collapsible portion of the clip member that folds at one or more predefined sites along each web member as the mounting portions are urged closer to each other.

Yet another exemplary system is provided. The system may comprise a fixation device including at least one or two or more collapsible clip members. The fixation device may include a spanning portion, such as a plate member, configured to extend along a bone, such as a rib bone, to span at least one discontinuity thereof. Each clip member may be connected integrally to (e.g., may be continuous with) the spanning portion, such that the spanning portion and clip member are each integral to a same piece of the fixation device, or the clip member and the spanning portion may be provided by discrete components. In some embodiments, the spanning portion may be a discrete base plate configured to extend along a bone and including no clip member (or including one or more integral clip members), and one or more discrete clip members may be received on the bone over the base plate.

Each clip member may include a pair of mounting portions configured to opposingly flank a bone and a collapsible portion connecting the mounting portions to each other. Each mounting portion may define one or more apertures configured to receive a fastener, and the mounting portions collectively may define one or more pairs of apertures, with the apertures of each pair aligned with each other on the same fastener-receiving axis. The collapsible portion may be deformable to decrease the spacing of the mounting portions from each other, optionally without substantially increasing the height or profile of the clip member. The collapsible portion may include one or more web members that each extend from one mounting portion to the other mounting portion. Each web member may follow a serpentine path when projected orthogonally onto a horizontal plane and an arched or arcuate path when projected orthogonally onto a vertical plane oriented perpendicular to a through-axis of the clip member. The web member may be configured to fold at one or more predefined sites as the mounting portions are urged toward each other. Folding that occurs at the one or more predefined sites may be about one or more axes that are transverse to a through-axis of the clip.

The system may include an installation tool for use with a pair of mounting portions and/or a collapsible clip. The tool may include any suitable combination of a mounting portion/clip holder, a clamping or compression device, a measuring device (a gauge), and a guide device (a guide). The tool may be configured to be connected to a pair of mounting portions and/or a collapsible clip, optionally with one or both of the mounting portions and/or the clip attached fixedly to the tool. The tool may be operated to urge the mounting portions toward each other, such as by applying compression to the mounting portions and/or clip, to controllably collapse the clip and conform the clip to a bone. The tool also may include a measuring device that measures a linear dimension between jaws of the tool, to permit selection of a fastener with an appropriate length for placement through bone and into an aperture of each mounting portion. The tool further may provide a guide for hole-forming tool and/or a fastener, to allow the hole-forming tool and/or fastener to be guided along a guide axis extending through both mounting portions. The guide axis may extend coaxially to a fastener-receiving axis of an aligned pair of apertures of the mounting portions and/or clip. Alternatively, or in addition, the guide axis may be used to create an aperture in at least one of the mounting portions, such as by drilling or punching through the mounting portion.

The bone fixation system disclosed herein has substantial advantages over other approaches to bone fixation with mounting portions disposed across a bone from each other. The advantages may include any combination of a closer fit of the mounting portions to bone, less irritation due to poorly-fitting mounting portions and/or fasteners that are too long, selection of a clip and/or mounting portions without the need to measure the thickness of the bone (e.g., one size of clip can be conformed to many different sizes and shapes of bone), less tendency for fasteners to pull out of bone, and more efficient installation of mounting portions and/or clips on bone, among others.

These and other aspects of the present disclosure are described in the following sections: (I) exemplary bone fixation system with opposed mounting portions, (II) exemplary installation tool for collapsible clips, (III) bone fixation system with discrete clips and/or mounting portions, (IV) methods of bone fixation with opposed mounting portions, (V) exemplary system combinations, and (VI) examples.

I. EXEMPLARY BONE FIXATION SYSTEM WITH OPPOSED MOUNTING PORTIONS

FIG. 1 shows selected aspects of an exemplary bone fixation system 50 including a fixation device 52 mounted on a bone 54, in this case, a rib bone. (The fixation device interchangeably may be termed a bone plate.) The fixation device 52 may include a spanning portion 56 (e.g., a plate member) configured to extend along a bone, to span a discontinuity in the bone, such as one or more fractures 58

(and/or cuts). The fixation device also may include or more pairs 59 of mounting portions arranged across bone 54 from each other. For example, in the depicted embodiment, each mounting portion pair 59 is provided by a continuous clip member (interchangeably termed a clip), namely, clips 60 each collapsed on bone 54 and extending to opposite sides (e.g., outer and inner surface regions) of the bone. In other embodiments, the mounting portions of pair 59 may be provided by discrete pieces (e.g., see Sections III and VI). In any event, the fixation device may be secured to bone 54 with threaded fasteners 64, such as bone screws, which may be received by the mounting portions of each clip 60 and by spanning portion 56. For example, in the depicted embodiment, each clip has received two bone screws and the spanning portion has received four bone screws.

Each clip 60 may be collapsed any suitable amount (or not at all) to allow the clip to be custom-fitted onto a region of bone 54. For example, here, the left clip is disposed on a thicker region of bone 54 than the right clip and has been collapsed less than the left clip. A clip that has been compressed, bent, deformed, and/or folded from its initial configuration (e.g., the configuration in which the clip is manufactured and supplied to a user), to produce a decrease in a characteristic dimension of the clip (e.g., generally the width of the clip measured across bone), may be described as a collapsed clip. The ability to collapse a clip by an adjustable amount on bone, and to change the shape of the clip, allows copies of the same clip to be modified on bone to fit on and/or to conform to different sized/shaped regions of the same bone, distinct bones of the same recipient or different recipients, and/or different types of bones (e.g., ribs and clavicles, among others).

Figure 2:
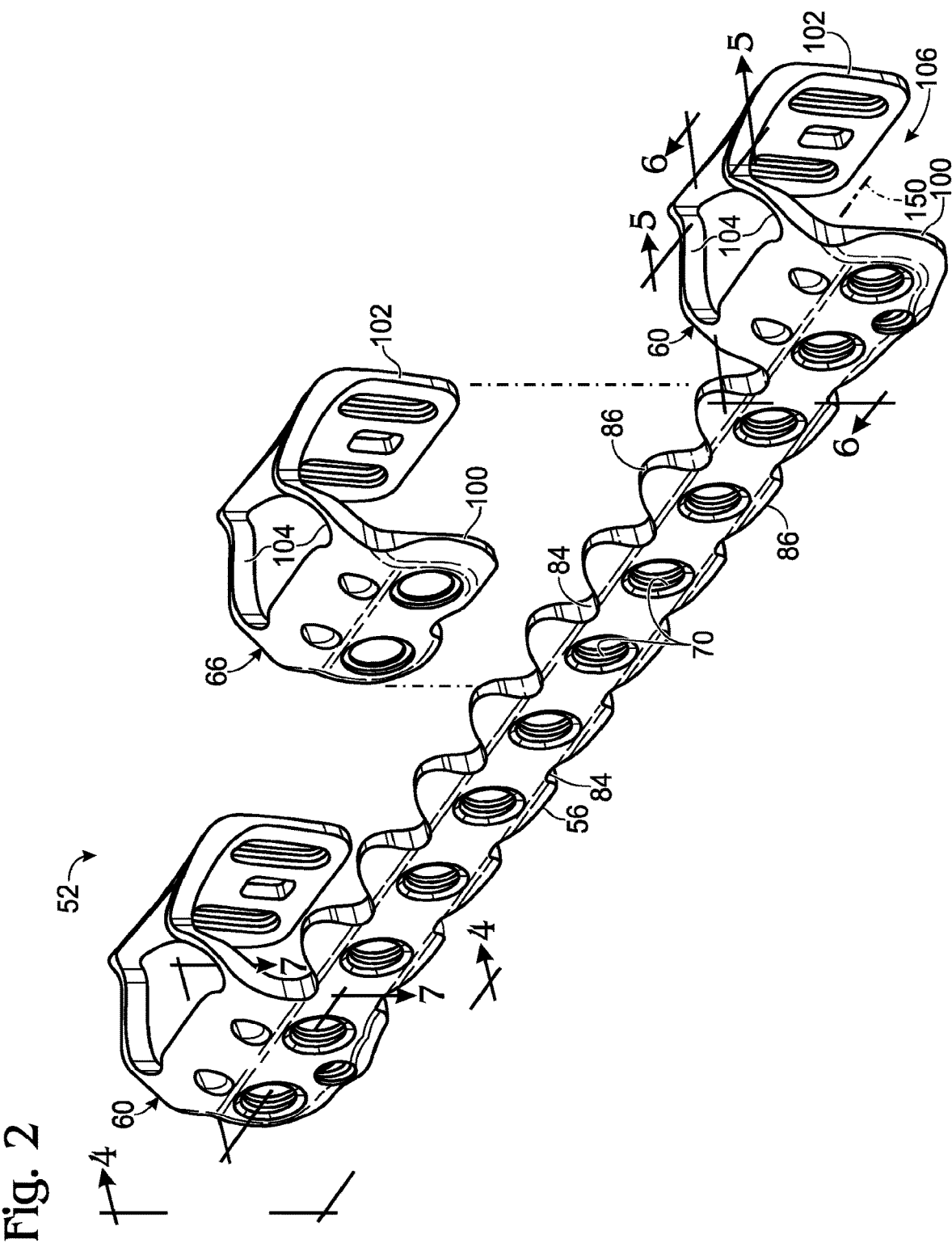
FIG. 2 is an isometric view of the fixation device of FIG. 1 taken in the absence of fasteners and bone, before a spanning portion of the fixation device has been conformed to the rib bone and before the clips have been collapsed.

FIG. 2 shows fixation device 52 in an original (uncollapsed) configuration before spanning portion 56 has been conformed to the longitudinal contour of bone 54 and before clips 60 have been collapsed (compare with FIG. 1). In addition, or alternatively to integral clips 60, the fixation device may include at least one discrete clip 66 (and/or at least one discrete mounting portion) that is provided as a separate piece and cooperates with spanning portion 56 to receive a fastener that attaches the clip and spanning portion to bone (e.g., see Sections III and VI).

Spanning portion 56 may be configured to extend along a bone. The spanning portion may be elongate and, in its supplied configuration, may define a long axis that is linear, as shown here, or curved. If the long axis is curved, the spanning portion may have in-plane or out-of-plane curvature. In some cases, the spanning portion may be twisted somewhat about the long axis in its original configuration.

FIGS. 2 and 3 show further aspects of the spanning portion. The spanning portion may define a plurality of apertures 70 (which interchangeably may be termed through-holes or openings) to receive fasteners. The apertures may be arranged at least generally along a long axis of the spanning portion and/or fixation device, and may be arranged in a line or may be offset from one another laterally (e.g., staggered). Each aperture 70 may or may not be (and/or may or may not be used as) a locking aperture. A locking aperture is engageable with a fastener to attach the fastener to the aperture and to restrict translational motion of the fastener in both axial directions parallel to the long axis of the fastener. The locking aperture also generally restricts lateral motion of the fastener along at least one axis orthogonal to the fastener's long axis and optionally along a pair of orthogonal axes in a plane that is orthogonal to the long axis. In any event, aperture 70 may include at least one internal thread or at least a pair of internal threads 71, 72 to engage fastener 64 (see FIG. 3). (An internal thread, as used herein, may be described as a helical groove (interchangeably termed a helical channel) and/or a helical ridge defined by an aperture.) In other embodiments, aperture 70 may be a locking aperture including a linear ridge and/or a linear groove (see below). Each aperture 70 may be circular or may be elongated parallel to a plane defined by the spanning portion, to form a slot. Also, each aperture may or may not define a tapered or cylindrical counterbore 74 of larger diameter above a bore of smaller diameter. The counterbore may be configured to receive at least a portion of a head of a fastener.

FIG. 3 shows exemplary surface features of spanning portion 56. A top or outer surface 76 of the spanning portion may be sloped or beveled laterally of the apertures, indicated with an arrow at 78, and/or laterally of inter-aperture regions of the spanning portion. Also, a central surface region 80 of top surface 76 may be flat, to facilitate abutment of the central surface region with an overlapping clip (e.g., see Section III). In contrast, the spanning portion may have a bottom or inner surface 82 (to face bone) that is arcuately concave in transverse cross-section, as shown in FIG. 3. Surface 82 may provide a better fit of the spanning portion on a transversely convex surface region of a bone.

FIG. 2 shows an exemplary shape for the spanning portion. The width may be variable to, for example, produce a wavy or scalloped perimeter that defines a series of indentations 84 (interchangeably termed notches) formed by opposing lateral edges 86 of the spanning portion. The indentations may provide convenient sites for the spanning portion to be broken, cut, or bent, among others. Alternatively, or in addition, the indentations may facilitate alignment with and attachment to an installation tool (e.g., see Section III).

FIGS. 2 and 4-9 show various views of clips 60. In the depicted embodiment, the clips are mirror-image copies of each other; left and right clips 60 are not distinguished from each other in the following discussion. Each clip, whether integral or discrete, may include a proximal mounting portion 100 (interchangeably termed a front or first mounting portion) and a distal mounting portion 102 (interchangeably termed a back or second mounting portion) that face each other. A collapsible portion 104 of the clip may interconnect the proximal and distal mounting portions. Mounting portions 100, 102 and collapsible portion 104 may collectively form a cavity 106 for receiving a bone (and, optionally, to receive a portion of a discrete plate member that provides the spanning portion), to permit the mounting portions to be disposed across the bone from each other (e.g., disposed on respective, opposite sides of the bone).

The clip may define one or more apertures to receive a fastener that secures the clip to bone (see FIGS. 4-7). More particularly, proximal and distal mounting portions 100, 102 of the clip may define one or more pairs of aligned apertures, with the apertures of each pair arranged on the same fastener-receiving axis. Apertures arranged on the same fastener-receiving axis are capable of receiving the same linear fastener with the fastener extending from one aperture to the other aperture. The fastener may lock to one or both apertures of the pair. If the clip has more than one pair of aligned apertures, the pairs may be spaced from each other along the long axis of the fixation device. For example, proximal mounting portion 100 defines a pair of proximal apertures 70 that respectively align with a pair of distal apertures 112 defined by distal mounting portion 102. The proximal apertures may be copies of each other, and the distal apertures may be copies of each other. (Here, proximal apertures 70 of proximal mounting portion 100 are copies of apertures 70 of spanning portion 56.) The clip may be secured to bone with a fastener extending from a proximal aperture 70, through bone, and to an aligned distal aperture 112. Each proximal aperture and/or distal aperture of the clip interchangeably may be termed an opening, a through-hole, or a slot (an elongated aperture), among others. In the depicted embodiment, distal apertures 112 are elongated parallel to a plane defined by distal mounting portion 102, to form vertical slots. In some embodiments, the proximal apertures may be elongated to form slots. In some embodiments, the proximal apertures and the distal apertures may be circular.

Figure 6:
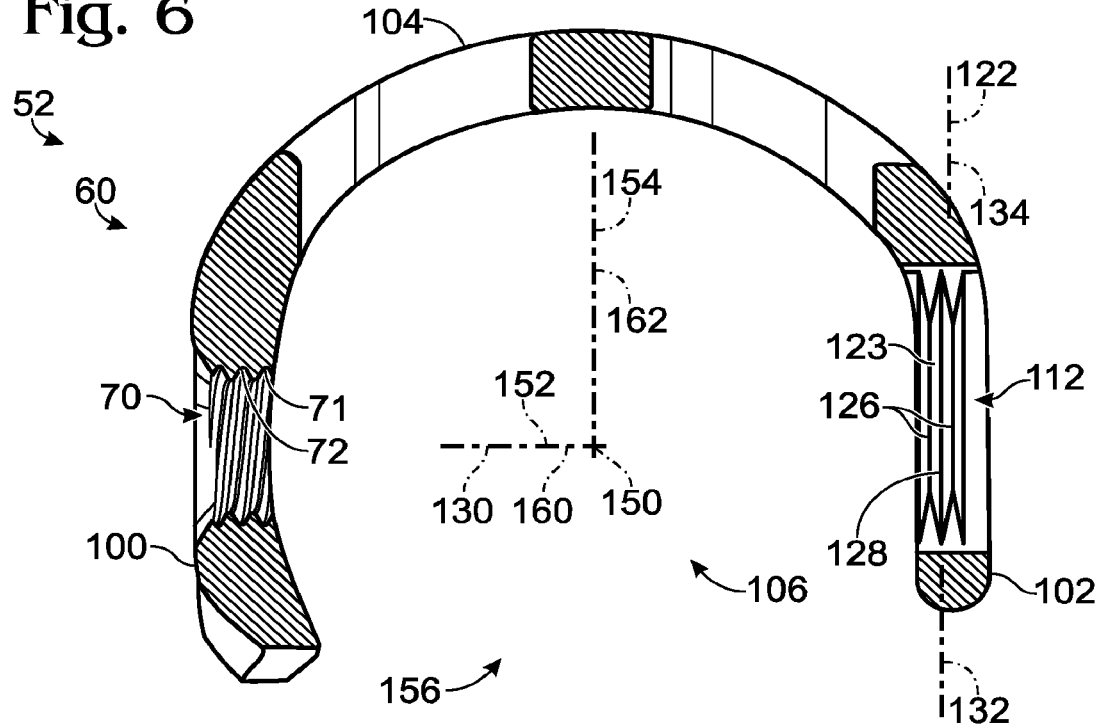
FIG. 6 is a cross-sectional view of the fixation device of FIG. 2, taken generally along line 6-6 of FIG. 2 through a pair of aligned apertures of a clip.
Figure 7:
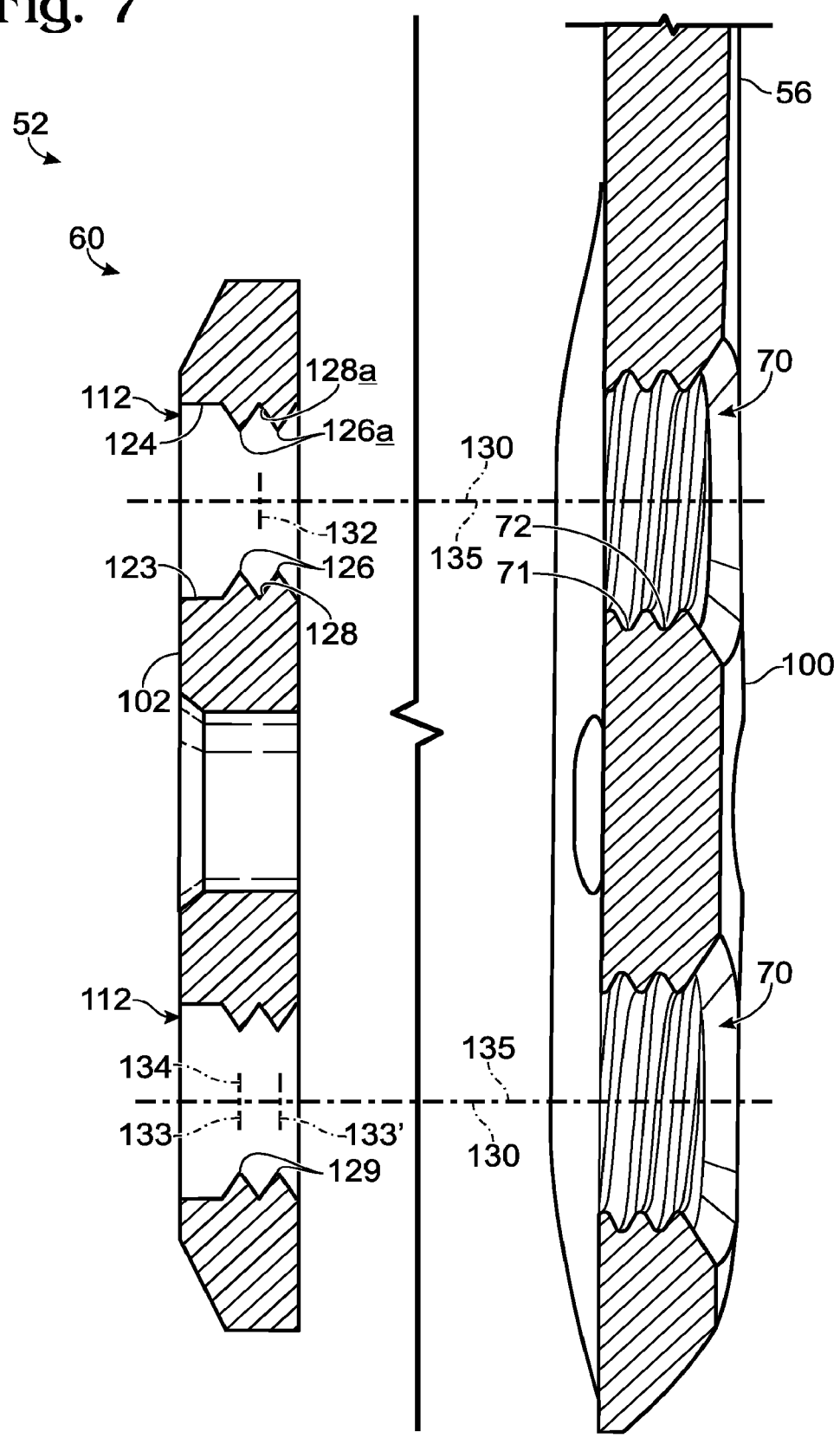
FIG. 7 is a fragmentary sectional view of the fixation device of FIG. 2, taken generally along line 7-7 of FIG. 2.

FIGS. 6 and 7 show exemplary thread-engagement structure for the proximal and distal apertures of the clip (and/or for apertures of separate, discrete mounting portions). Each proximal aperture 70 of the proximal mounting portion may have a single thread or a pair of threads 71, 72 each with a distinct thread lead. In other embodiments, each proximal aperture of proximal mounting portion 100 may be nonlocking (e.g., nonthreaded).

Figure 5:
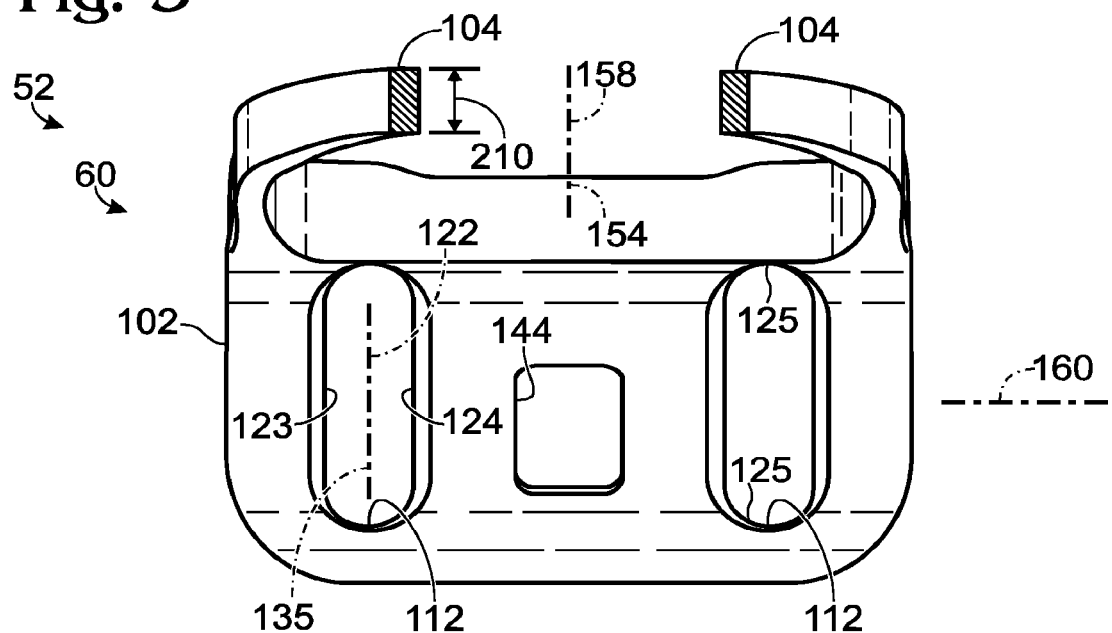
FIG. 5 is a fragmentary sectional view of the fixation device of FIG. 2, taken generally along line 5-5 of FIG. 2 such that only a back half of one of the clips is shown.

Distal aperture 112 may be elongated along a long axis 122 to form a slot (see FIG. 5). The slot has opposing side wall regions or linear walls 123, 124 disposed across the slot (and across long axis 122) from each other, in other words, on opposite sides of long axis 122. Side wall regions 123, 124 are connected to each other by end wall regions 125 of the slot, which may be arcuate, as shown here. Each side wall region may define one or more grooves and/or ridges that extend along the slot, for example, at least substantially parallel to long axis 122 or a plane defined by the mounting portion at the aperture. Each groove and each ridge may be at least substantially linear. Additional ridges and grooves may or may not be defined by end wall regions 125, as arcuate extensions of the linear ridges and grooves, which may or may not extend from the linear ridges and grooves of one side wall region to those of the opposite side wall region.

One or both side wall regions 123, 124 may engage an external thread of a fastener at the groove(s) and/or ridge(s) to lock the fastener to the slot. Accordingly, ridges and a groove may be defined by only one of the opposing side wall regions or both. In the depicted embodiment, each side wall region of slot 112 defines a pair of linear ridges 126 (or 126a). A linear groove 128 (or 128a) is defined between crests 129 of each pair of the ridges (see FIGS. 6 and 7). The ridges and groove of one side wall region may be aligned with those of the opposing side wall region of slot 112, such that there is no offset from one another along a fastener-receiving axis 130. (Axis 130 extends through the aligned apertures and optionally is defined by proximal aperture 70.) For example, within a slot, the grooves collectively and/or the pairs of ridges collectively may define a groove plane 132 that is orthogonal to fastener-receiving axis 130. The groove plane is positioned between the crests of each pair of ridges, at the base of each groove. Alternatively, or in addition, an opposing pair of ridges, at their crests 129, may define a ridge plane 133 (or 133') that is orthogonal to fastener-receiving axis 130 (see FIG. 7). Groove plane 132 and ridge planes 133, 133' may be at least substantially parallel to a plane 134 defined by the mounting portion at slot 112.

The thread-engagement structure of slot 112 defines a fastener-receiving plane 135 containing a plurality of distinct fastener-receiving axes along which a fastener can be advanced into the slot for attachment to the slot (if mounting portion 100 is ignored). The distinct fastener-receiving axes may be nonparallel to one another and/or may have distinct positions along long axis 122. Plane 135 may be defined collectively by long axis 122 of slot 112 and fastener-receiving axis 130. Alternatively, or in addition, plane 135 may be defined as a plane containing long axis 122 and oriented orthogonal to groove plane 132 and/or one or more ridge planes 133 and/or 133'. An external thread of a fastener can attach to the thread-engagement structure of the slot in a pair of interchangeable configurations as described in more detail below.

FIGS. 4 and 5 show additional aspects of the clip. Proximal mounting portion 100 and/or distal mounting portion 102 each may define one or more additional openings that facilitate alignment and/or attachment of the clip to an installation tool. In the depicted embodiment, proximal mounting portion 100 defines a pair of upper holes 140 and a lower hole 142 (see FIG. 4). Any of holes 140, 142 may be locking, such as having an internal thread. Also, distal mounting portion 102 defines a distal opening 144 (see FIG. 5). Exemplary utilization of holes 140, 142 and opening 144 by an installation tool is described below in Section II.

The clip defines a set of three orthogonal axes. The clip defines a through-axis 150 for a bone to extend through the clip (see FIGS. 2, 6, and 8). Through-axis 150 is centered in cavity 106 and extends through the cavity in a spaced relation to mounting portions 100, 102 and collapsible portion 104. Through-axis 150 may be at least generally parallel to a longitudinal axis of a bone received in the cavity and may be substantially parallel to respective planes defined by one or both of the mounting portions and/or to the long axis of the fixation device. The clip also defines a transverse axis 152 extending through both mounting portions, such as at least generally orthogonal to both mounting portions (see FIGS. 6 and 8). Transverse axis 152 is orthogonal to through-axis 150 and may be at least substantially parallel to, and/or coincident with, a fastener-receiving axis 130 and/or at least substantially parallel to a trajectory of a linear fastener extending between a pair of apertures of the clip. The clip further defines a bone-receiving axis 154 (see FIGS. 5 and 6), interchangeably termed an entry axis or a vertical axis, along which the clip may be placed on a bone or taken off a bone. The clip may form a mouth region 156 (e.g., an open bottom side) opposite collapsible portion 104 (see FIG. 6), and bone-receiving axis 154 may extend through the mouth region and collapsible portion 104. The bone-receiving axis is orthogonal to each of through-axis 150 and transverse axis 152. In some cases, bone-receiving axis 154 may be described as a height axis, irrespective of the orientation in which the clip is used on bone.

The clip also defines a set of three orthogonal planes. The clip defines a central plane 158 (interchangeably termed a central vertical plane) that is orthogonal to through-axis 150 (see FIGS. 4, 5, and 8). The clip also defines a transverse plane 160 (interchangeably termed a horizontal plane) that contains through-axis 150 (see FIGS. 4, 5, and 6). The clip further defines an intermediate plane 162 that intersects collapsible portion 104 but neither clip member (see FIGS. 6 and 8). Intermediate plane 162 conceptually divides the clip into (a) a proximal portion containing proximal mounting portion 100 and a front section of collapsible portion 104 (e.g., as shown in FIG. 4) and (b) a distal portion containing distal mounting portion 102 and a rear section of collapsible portion 104 (e.g., as shown in FIG. 5).

The clip may have any suitable shape. For example, the clip may be at least generally U-shaped in profile (i.e., when viewed parallel to through-axis 150 and/or when projected orthogonally onto central plane 158 (see FIG. 6).

FIGS. 8 and 9 show top and end views of clip 60 received on bone 54 and illustrating the clip being deformed from an initial configuration to a collapsed configuration. In FIG. 9, the clip has been secured to the rib bone with fastener 64 after being collapsed. The clip may be configured to collapse by selectively deforming collapsible portion 104 as proximal and distal mounting portions 100, 102 are moved toward each other along transverse axis 152 (and/or along an axis, such as a compression axis, that is parallel to fastener-receiving axis 130). The mounting portions have a spacing or separation distance 180, measured parallel to transverse axis 152, which decreases as the mounting portions are urged toward each other (see FIGS. 8 and 9). Stated differently, a dimension (e.g., width), measured across the clip parallel to transverse axis 152 and/or axis 130, decreases as the clip is collapsed.

As the mounting portions move toward each other, they may retain the same relative angular orientation (e.g., may remain parallel to each other), or one or both may change their orientation. For example, FIG. 9 shows distal mounting portion 102 tilted in the collapsed configuration, with respect to its original orientation (and with respect to proximal mounting portion 100). The distal mounting portion has pivoted about an axis parallel to through-axis 150 (see FIGS. 2, 6, and 8), which may be desirable to conform the shape of the clip to that of a bone, such as bone 54 having less convex curvature and/or a concave surface region 182 adjacent the distal mounting portion (see FIG. 9). An installation tool may restrict the orientation and range of pivotal motion permitted (e.g., see Section II and Example 1). As shown in FIG. 9, fastener 64 can be engaged with the thread-engagement structure of slot 112 through a range of angles produced by clip collapse, because fastener-receiving axis 130 remains in fastener-receiving plane 135 (also see FIGS. 5 and 7) as the distal mounting portion pivots about one or more axes parallel to through-axis 150 (also see FIG. 6 and Example 1).

Collapsible portion 104 may be structured to permit mounting portions 100, 102 to move closer to each other without a substantial increase in the height (h) of the clip, as measured parallel to bone-receiving axis 154 (see FIGS. 6 and 9). For example, the increase in height may be less than about 5% or 10%, among others. In other words, the profile of the clip above a bone may not increase substantially as the clip is collapsed around the bone. As a result, the path followed by the clip between opposing sides of the bone becomes shorter as the clip is increasingly collapsed, with the decrease in path length being produced preferentially (i.e., at least predominantly or substantially exclusively) by bending that occurs within the collapsible portion. The path length of the clip is defined by an orthogonal projection of the clip onto central plane 158 (see FIGS. 5 and 8).

FIG. 8 shows collapsible portion 104 in more detail. This portion may include one or more web members 190 (interchangeably termed interconnection members or strap members) that provide a connection between proximal and distal mounting portions 100, 102. The depicted embodiment has a pair of web members 190. Each web member 190 may be elongate and has a smaller characteristic dimension (e.g., is narrower and/or thinner) than the mounting portions. For example, measured parallel to through-axis 150, each web member 190 may have a characteristic transverse dimension 192 that is substantially less than a corresponding characteristic dimension 194 of each mounting portion, such as with transverse dimension 192 being less than about one-half, one-fourth, or one-tenth characteristic dimension 194.

Each web member 190 may be integral to the clip, meaning that the web member cannot be separated from the mounting portions without damaging (e.g., breaking, cutting, tearing, melting, etc.) the clip. Accordingly, the web member may be continuous with the mounting portions, and/or the clip may be a single piece (e.g., a monolithic structure). In some cases, the web members may separately extend (relative to each other) between the mounting portions, to separately connect to each mounting portion at respective spaced positions.

Each web member, before and/or after collapse, may extend from one mounting portion to the other mounting portion along a nonlinear path that bends one or more times. Each bend may be an angular bend, an arcuate bend, or a combination thereof. The path may bend in at least one plane (e.g., in a first plane parallel to transverse plane 160, in at least a pair of orthogonal planes (e.g., a first plane parallel to transverse plane 160 and a second plane parallel to central plane 158), or in three mutually orthogonal planes (e.g., the first plane, the second plane, and a third plane parallel to intermediate plate 162 (see FIG. 8)). A path that bends in a plane is nonlinear if projected orthogonally onto that plane. The web member may have at least one bend that forms any suitable angle when projected orthogonally onto the first plane before the clip is collapsed, such as about 45° to 120°, among others. Also, the web member may extend from each mounting portion at any suitable angle when projected onto the first, second, or third plane, to form any suitable angle collectively with the mounting portion, such as an angle of less than 90°, about 90°, or greater than 90°. The web member also may follow a nonlinear path when projected onto the second plane such that the web member is arcuate in profile (as viewed parallel to through-axis 150). Alternatively, or in addition, each web member may have a variable separation from central plane 158 as the web member extends from the proximal mounting portion to the distal mounting portion. In any event, at least part of each web member is configured to undergo a change in separation distance from central plane 158 when the collapsible portion deforms.

The web member may have one or more predefined regions where the web member deforms preferentially as the clip is collapsed. The deformation may be plastic deformation, elastic deformation, or a combination thereof, although plastic deformation may be preferred. In the depicted embodiment, each web member has a plurality of regions where each web member (and/or the clip) bends or folds preferentially, namely, an intermediate region 200 and opposing end regions 202, 204 (each of which may be termed a folding site). The web member bends or folds at each of regions 200-204 about one or more mores that are transverse to through-axis 150 and/or at least generally parallel to bone-receiving axis 154 (e.g., within about 20 degrees of parallel), when the clip is collapsed.

The web member also may have a cross-sectional shape that encourages the web member to bend horizontally (see FIG. 5). For example, the web member may have a vertical transverse dimension 210, measured parallel to bone-receiving axis 154, that is greater than horizontal transverse dimension 192 (see FIG. 8), measured parallel or at least generally parallel to through-axis 150. In other words, when the clip is oriented with the collapsible portion on top, the web member may be relatively thicker vertically and relatively thinner horizontally to encourage horizontal bending.

FIG. 8 shows that the clip may define a large opening or window 212 having a perimeter formed by mounting portions 100, 102 and web members 190. The shape and size (e.g., area) of the window may change as the clip is collapsed.

Figure 10:
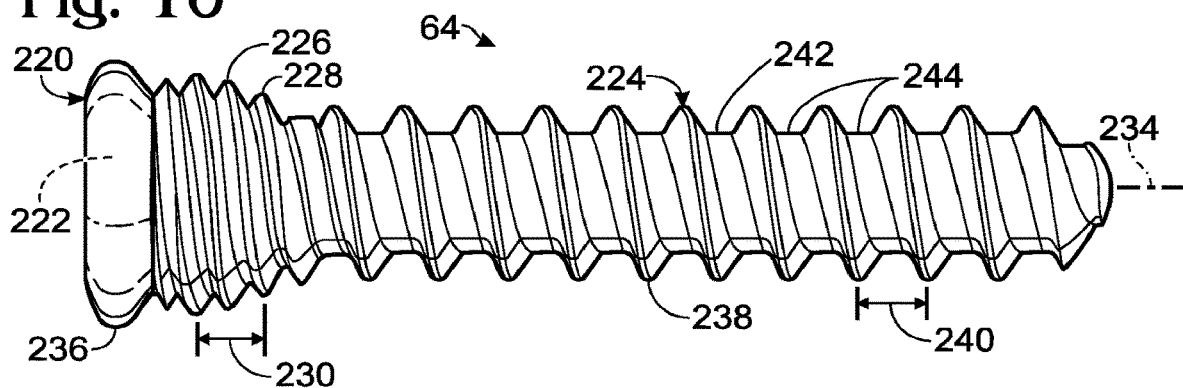
FIG. 10 is a side view of the fastener of FIG. 9, in accordance with aspects of the present disclosure.

FIG. 10 shows fastener 64. The fastener has a head 220 defining a driver engagement structure (e.g., a socket 222), and a shaft 224 projecting distally from the head, with the head having a larger diameter than the shaft. Each of head 220 and shaft 224 may include at least one external thread to lock the fastener to each mounting portion of a clip, or the head may have no thread.

In the depicted embodiment, head 220 has a pair of threads 226, 228 having the same pitch 230. Threads 226, 228 have an offset from each other parallel to a long axis 234 defined by the fastener, with the offset being less than pitch 230, such as about one-half the pitch. In other words, the head has a multi-threaded structure complementary to the multi-threaded structure of apertures 70 (see FIGS. 3 and 7), to permit locking engagement of head 220 to the aperture. Head 220, due to its multi-threaded structure, can interchangeably lock to the proximal aperture in a pair of distinct configurations. More particularly, in one configuration, head thread 226 is received in aperture thread 71, and head thread 228 is received in aperture thread 72. In another configuration, the threads switch partners, with head thread 226 received in aperture thread 72 and head thread 228 received in aperture thread 71. In some cases, multi-threaded engagement of head 220 with the proximal mounting portion of the clip may provide substantial advantages over single-threaded engagement. For example, the head may thread more easily, reliably, and reproducibly into the proximal mounting portion during surgery, because the range of possible misalignment of the external and internal threads, along the fastener-receiving axis, when the head initially reaches the aperture is reduced by a factor of two. As a result, the head can be threaded into a mounting portion aperture with less stress on bone, less deformation of threads, and/or less shifting of the proximal mounting portion. Also, the double-threaded engagement of the head with the proximal mounting portion may provide a more robust locked engagement that reduces the chance of the bone screw backing out of bone.

Head 220 may have any other suitable structure and features. The diameter of head 220, and particularly the outer diameter of threads 226, 288 may decrease (e.g., taper) toward shaft 224. Also, each of threads to 226, 228 may run out proximally adjacent a seating region or flange 236 formed at the proximal end of the head. The seating region may have a larger diameter than the maximum outer diameter of threads 226, 228 and may function as a stop to block axial advancement of the fastener through a proximal aperture of the clip by engaging the proximal mounting portion, such as at the outer end of the aperture.

Shaft 224 has an external thread 238 (interchangeably termed a helical ridge) configured to provide attachment of the fastener to distal aperture 112. External thread 238 also may provide threaded engagement with bone. Thread 238 may have a pitch 240 that is equal to pitch 230 of head threads 226, 228, or the pitches may be different. Also, thread 238 may extend along a same helical path (of variable diameter) as head thread 228. Accordingly, head thread 228 may be continuous with shaft thread 238.

Shaft 224 also defines a helical channel 242, which extends in parallel with thread 238 on a helical path about long axis 234. The surface regions forming thread 238 also partly or completely form groove 242. The helical channel is composed of a plurality of revolutions 244 each representing a single complete extension around long axis 234.

Figure 11:
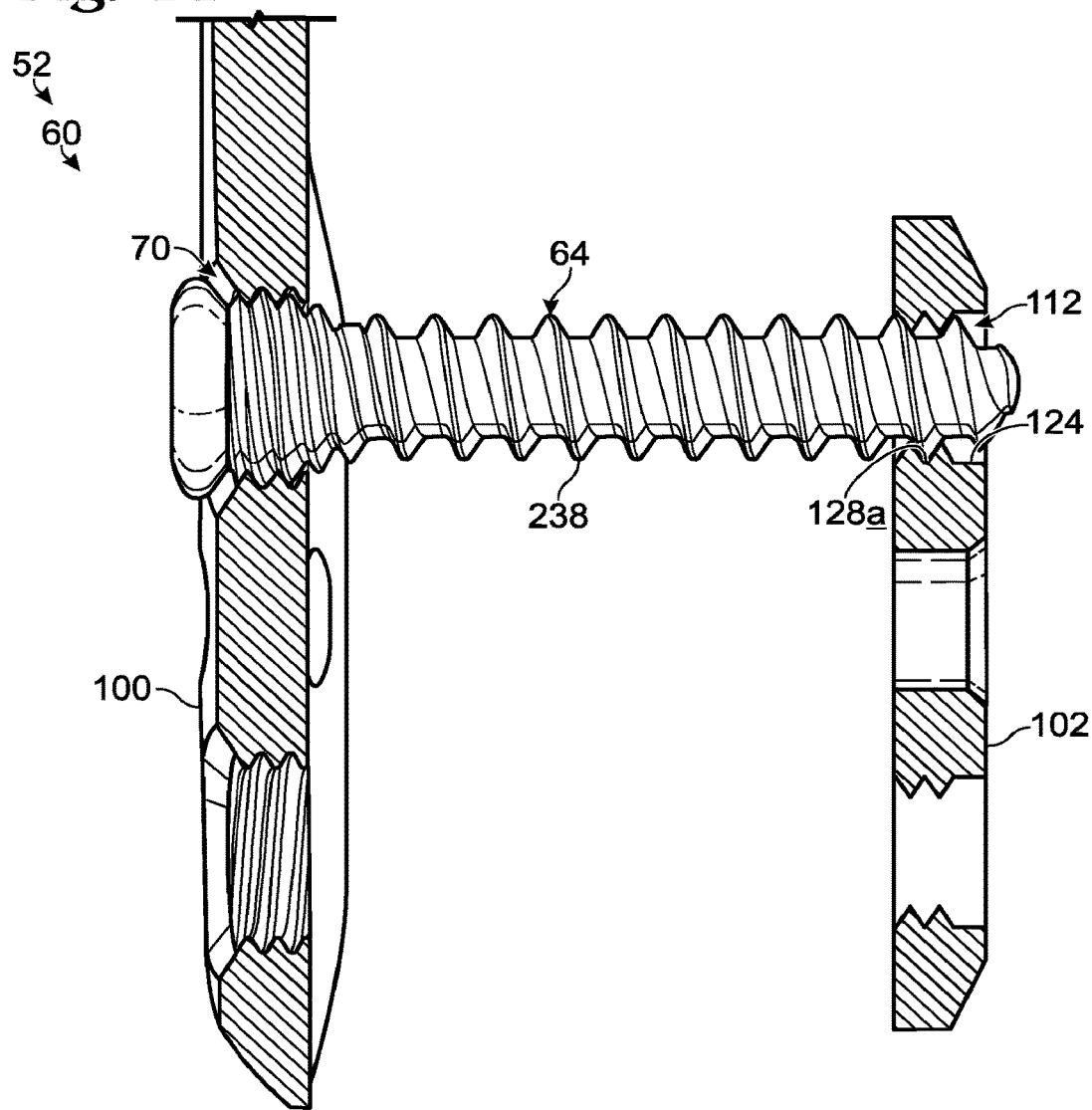
FIG. 11 is a sectional view of the clip and fastener of FIG. 9, taken generally along line 11-11 of FIG. 9 with the fastener attached to both mounting portions of the clip and with the mounting portions parallel to each other to simplify the presentation.

FIG. 11 shows a sectional view of clip 60 in locked engagement with fastener 64. Head threads 226, 228 (see FIG. 10) have been placed into threaded engagement with internal threads 71, 72 of proximal aperture 70 (also see FIG. 7). Also, shaft thread 238 has been placed into engagement (interchangeably termed attachment or threaded engagement) with slot 112, with the shaft thread received in a groove 128*a* defined by linear side wall region 124 (also see FIG. 5).

Figure 12:
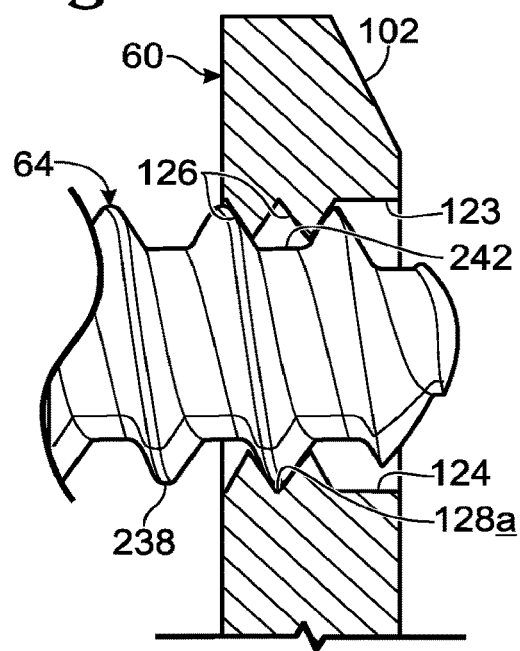
FIG. 12 is a fragmentary view of the clip and fastener of FIG. 11.
Figure 13:
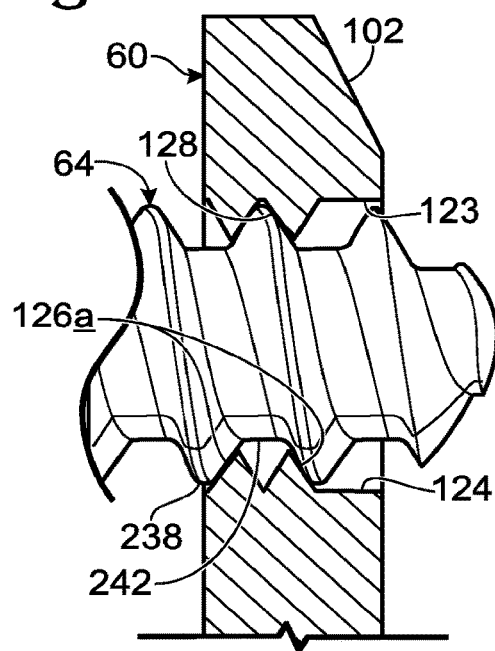
FIG. 13 is another fragmentary view of the clip and fastener of FIG. 11, taken generally as in FIG. 12, but with the fastener engaged with the clip in another attached configuration that is interchangeable with the attached configuration of FIG. 12, in accordance with aspects of the present disclosure.

FIGS. 12 and 13 illustrate interchangeable attached configurations of fastener 64 with the distal slot of distal mounting portion 102. Each configuration is defined by the particular groove 128 or 128*a* in which shaft thread 238 is received. Alternatively, if only one of the opposing side wall regions defines a groove and a pair of ridges, the configurations may be distinguished by whether the thread is disposed in the groove or oppositely flanks the pair of ridges. In FIG. 12, thread 238 is disposed in groove 128*a* of side wall region 124, and ridges 126 of opposing side wall region 123 are received in the same revolution or turn 244 of helical channel 242 (also see FIG. 10). The roles of side wall regions 123, 124 are reversed in the attached configuration of FIG. 13: thread 238 is disposed in linear groove 128 of side wall region 123, and linear ridges 126*a* of opposing side wall region 124 are received in helical channel 242 of thread 238. The distance between ridges 126 or 126*a* of each side wall region 123, 124 may be a less than pitch 240 (see FIG. 10), such as about one-half the pitch.

The interchangeable locked configurations offered by distal slot 112 for fastener 64 may provide the same general advantages as the interchangeable threaded configurations of head 220 with proximal aperture 70. In particular, the shaft of fastener 64 may thread more easily, reliably, and reproducibly into the distal mounting portion during surgery, because the range of possible axial misalignment of the external thread and the locking structure in the distal slot, when the external thread initially reaches the distal slot, is reduced by a factor of two relative to a single engaged configuration offered by offset ridges in the slot. As a result, the shaft can be threaded into a mounting portion slot with less stress on bone, less deformation of the thread/ridges, and less shifting of the distal mounting portion. Also, in the depicted embodiment, the engagement of the shaft with the distal mounting portion may be more robust because axial motion of the shaft through the distal slot in both axial directions may be blocked on both sides of the slot. Accordingly, the fastener can remain attached to the slot even if engagement of the thread with one of the side wall regions is defective or fails. The use of a locking slot also is advantageous because the slot can receive fastener 64 over a range of pivotal positions of the distal mounting portion (e.g., see FIG. 9 and Example 1). Further aspects of a mounting portion with a slot, and a fastener that interchangeably attaches to the slot in a pair of distinct configurations, are disclosed elsewhere in the present disclosure, such as in Example 5.

The mounting portions, clips, spanning portions, and fasteners of the present disclosure may be formed of any suitable biologically compatible material, such as metal, plastic, a bioresorbable material, or the like. Further aspects of mounting portions, clips, spanning portions, and fasteners that may be suitable are described elsewhere in the present disclosure, such as in Sections III, IV, and VI, among others.

II. EXEMPLARY INSTALLATION TOOL FOR COLLAPSIBLE CLIPS

This section describes an exemplary installation tool 250 for use with any of the collapsible clips disclosed herein; see FIGS. 14-18. (Also see Example 1 for additional disclosure.)

Figure 14:
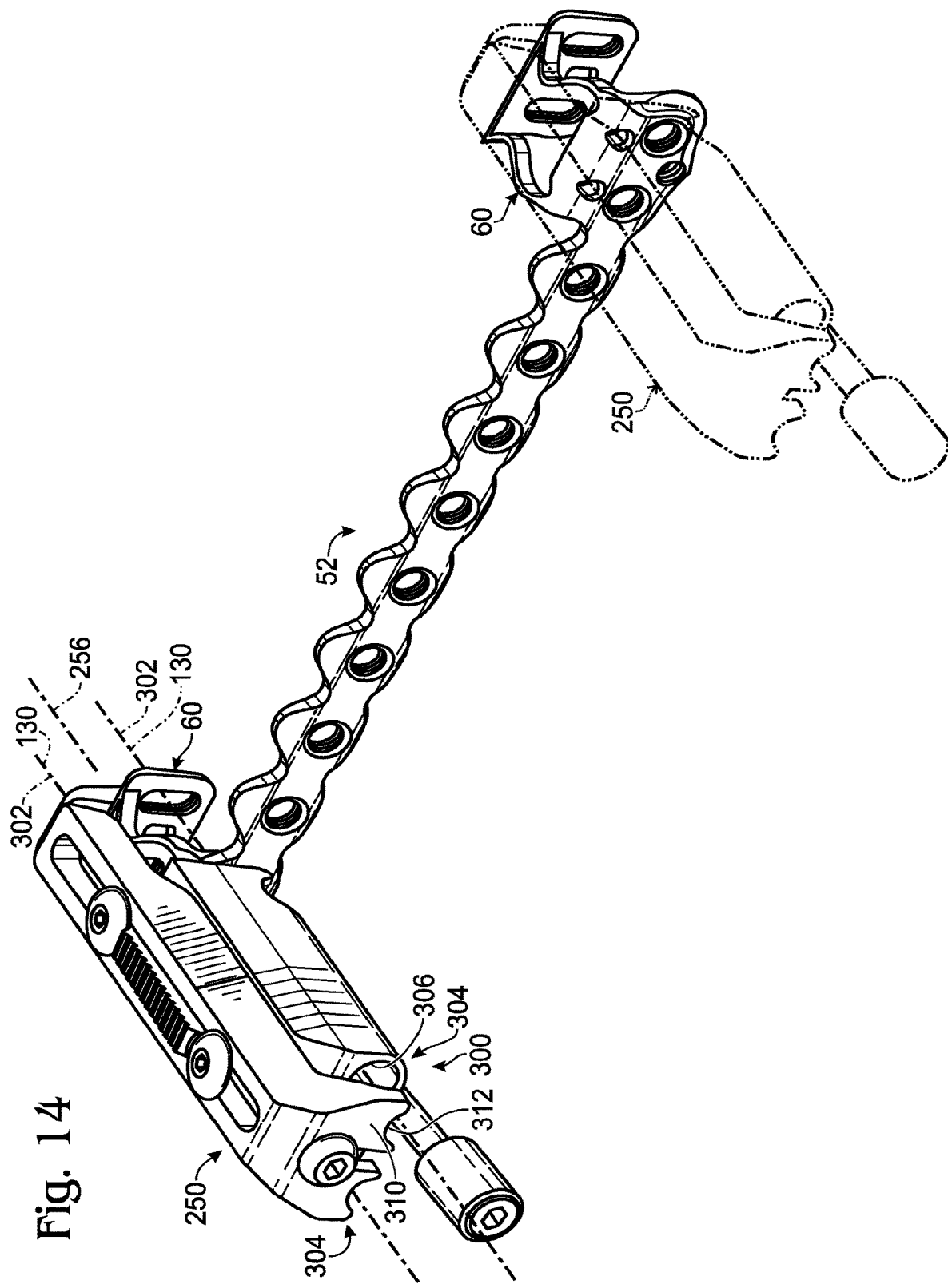
FIG. 14 is an isometric view of the fixation device of FIG. 2 attached at a clip to a tool to facilitate installation of the fixation device on bone, with a second copy of the tool shown in phantom attached to the other clip of the fixation device.

FIG. 14 shows fixation device 52 and two copies of tool 250 to facilitate installation of the fixation device on bone. One of the tool copies is attached to clip 60 of the bone plate and the other tool copy has not yet been attached and is shown in phantom. Each tool 250 may be attached to fixation device 52, and/or a clip 60 or one or more mounting portions thereof, before or after the fixation device is disposed on bone. In some cases, the fixation device may be pre-loaded, before placement on bone, with a copy of tool 250 attached to each clip 60.

The tool may perform various functions during clip installation. The tool may be described as a holder or holder device that holds, supports, and positions a clip before, during, and after placement of the clip onto bone. The tool also may be described as or may include a clamping device or clamping mechanism that adjustably collapses the clip. The tool additionally may be described as or may include a guide device or guide for guiding advancement of a drill, a fastener, a driver, or any combination thereof, among others. The tool further may be described as or may include a gauge device or gauge that allows measurement of a linear dimension (e.g., measured across the clip), to facilitate selection of a fastener with an appropriate length. The various devices and/or mechanisms of the tool may be provided by shared or dedicated components of the tool. Further aspects of the tool are described below.

Figure 15:
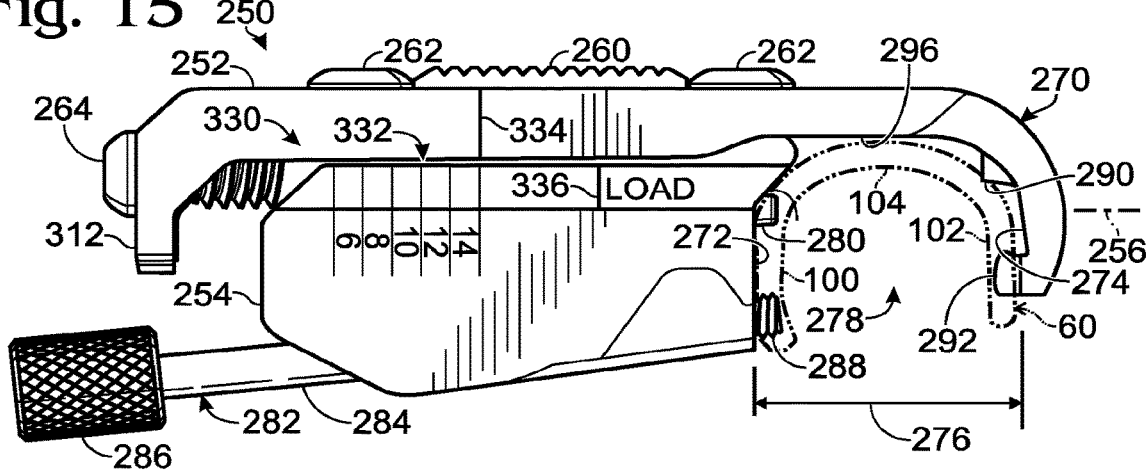
FIG. 15 is a side view of the tool of FIG. 14, taken with the clip shown in phantom.
Figure 16:
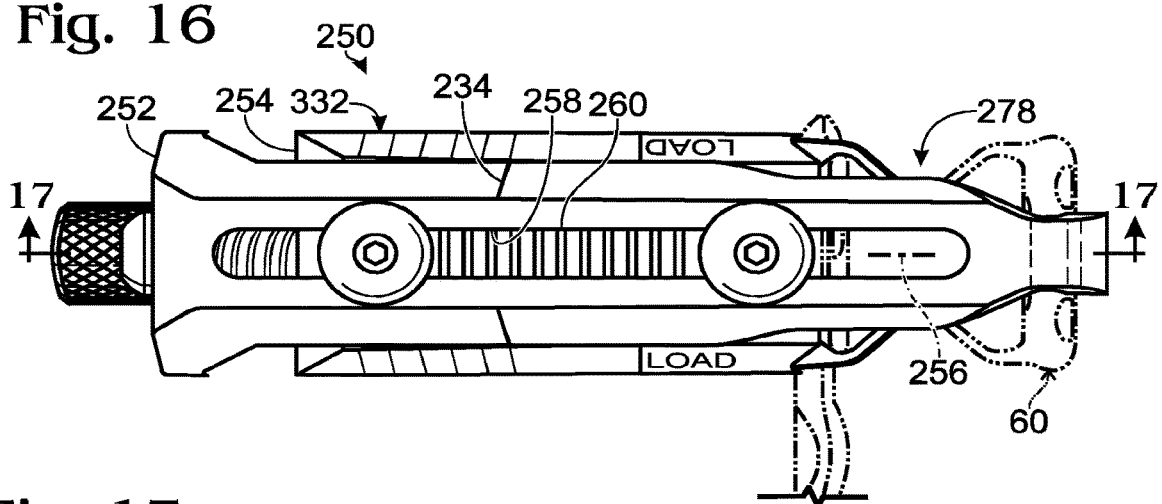
FIG. 16 is a top view of the tool of FIG. 14, taken with the clip shown in phantom.
Figure 17:
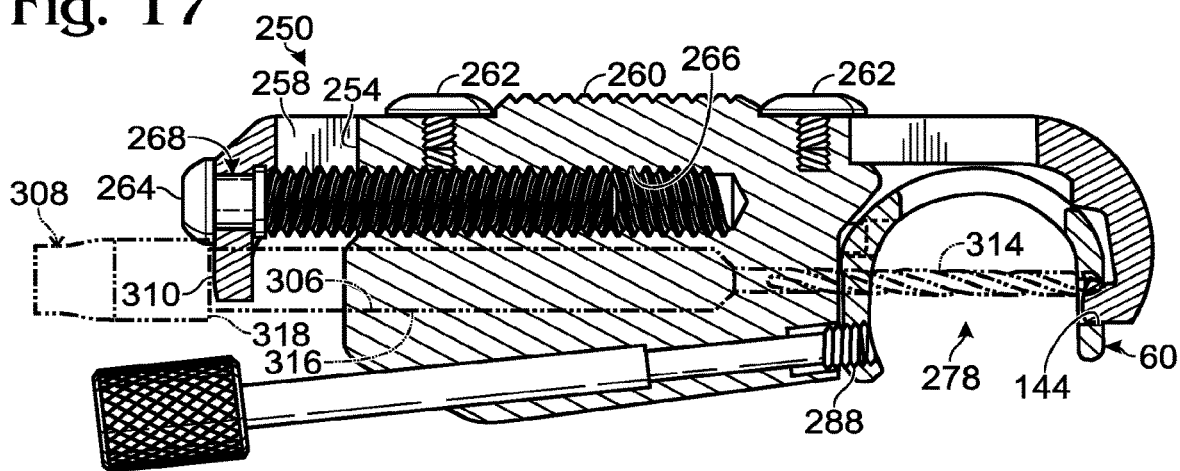
FIG. 17 is a sectional view of the tool of FIG. 14, taken generally along line 17-17 of FIG. 16.

FIGS. 15-17 show side, top, and sectional views of tool 250 taken with clip 60 in sectional or phantom view. The tool may include a frame member 252 (interchangeably termed a body member or first frame member) and a carriage 254 (interchangeably termed a second frame member) connected slideably to the frame member for linear motion parallel to a compression axis 256. For example, frame member 252 may form a track 258 (e.g., a slot; see FIG. 16), and the carriage may form a projection 260 shaped to be slideably received in the track. Frame member 252 may be connected to carriage 254 using a pair of screws 262 or other fasteners extending through track 258 and into threaded engagement with carriage 254 (e.g., see FIG. 17).

Carriage 254 may be driven parallel to compression axis 256, and relative to frame member 252, by a drive mechanism. For example, the drive mechanism may include a drive screw 264 (interchangeably termed a lead screw) extending through a proximal end of frame member 252 and into threaded engagement with a threaded bore 266 formed by carriage 254 (see FIG. 17). A proximal end of the drive screw, such as a neck thereof, may be rotatably held by frame member 252, indicated by an arrow at 268, to permit the drive screw to be turned without changing its axial position with respect to the frame member. Accordingly, turning the drive screw in either rotational direction drives the carriage forward or backward parallel to compression axis 256, relative to frame member 252. The drive screw may be configured to be engaged and turned by hand (e.g., with the drive screw having a graspable head) or with a driver (e.g., a screwdriver).

Frame member 252, carriage 254, and drive screw 264 collectively form a clamping device 270 (see FIG. 15). Carriage 254 may provide a proximal jaw 272, and frame member 252 may provide a distal jaw 274, or vice versa, to engage respective proximal and distal mounting portions 100, 102 of clip 60. Here, frame member 252 has a claw shape to form distal jaw 274. Jaws 272, 274 have a separation distance or spacing 276 that is adjustable by turning drive screw 264. Accordingly, the jaws can be driven closer together, to apply compressive force, by turning the drive screw in one rotational direction. Also, the jaws can be driven farther apart, to reset the tool for additional use (e.g., to load and collapse another clip), by turning the drive screw in the other rotational direction.

Tool 250 may form a receiver region 278 that is sized and shaped to receive a clip (see FIGS. 15-17). One or both jaws may provide one or more alignment features and/or retainers that engage the clip and/or mounting portions to dispose the clip/mounting portions in a predefined alignment with the tool. The alignment features may align the clip with the tool along a pair of axes orthogonal to compression axis 256. One or more alignment features of each jaw may project toward the other jaw and may be configured to be received in one or more openings of the clip to align the clip with the tool and attach the clip to the tool. Proximal jaw 272 may form at least one or a pair of fixed pins 280 that project at least generally toward the distal jaw. Each pin 280 may be received in an upper hole 140 of proximal mounting portion 100 (also see FIG. 4). An adjustable retainer or locking member 282 also may project into receiver region 278 from proximal jaw 272. Locking member 282 may include a rod 284 having a graspable knob 286 formed at a proximal end and a threaded tip 288 formed at a distal end. The locking member may be disposed in threaded engagement with lower hole 142 of proximal mounting portion 100 to lock the mounting portion and/or clip to tool 250 (see FIGS. 4, 15, and 17). Distal jaw 274 may form an abutment member 290 to engage a top edge of distal mounting portion 102 at a perimeter of window 212 (see FIGS. 8 and 17). The distal jaw also may form a tip or tooth 292 projecting toward the proximal jaw and configured to be received in distal opening 144 of distal mounting portion 102 (see FIGS. 15 and 17). The tooth may be sized and shaped to permit the orientation of the distal mounting portion to change by pivotal motion about the tooth as the clip is collapsed (also see Example 1).

Receiver region 278 may restrict collapsible portion 104, and particularly web members thereof, from bending upward as the clip is collapsed. Frame member 252 may form a top wall 296 of the receiver region that blocks substantial upward travel of the web members (see FIG. 15).

The clip can be connected to tool 250 as follows. The jaws are placed in a loading configuration in which the uncollapsed clip easily fits between the jaws. Upper holes 140 of proximal mounting portion 100 are placed onto pins 280, and locking member 282 is turned into threaded engagement with lower hole 142 of mounting portion 100. The user then turns drive screw 264 to move carriage 254 and its attached clip into engagement with distal jaw 274, with abutment member 290 in window 206 and tooth 292 in distal opening 144. Alternatively, locking member 282 may be disposed in threaded engaged with mounting portion 100 after both mounting portions 100, 102 have been engaged by jaws 272, 274. In any event, the drive screw may be turned to urge the mounting portions of the clip toward each other, to collapse the clip around bone.

FIG. 14 shows a guide 300 of tool 250 that then may be utilized to facilitate placement of fasteners 64 that secure the collapsed clip to bone, while the clip remains attached to tool 250 and clamped on bone by clamping device 270. The guide may define one or more guide axes or guide paths 302 for guiding a drill member (interchangeably termed a drill) and/or driving fasteners through bone. Guide axes 302 each may be parallel to compression axis 256. Also, each guide axis may be coaxial with a corresponding fastener-receiving axis 130 extending through a pair of aligned apertures of the clip.

Each guide axis 302 may be defined by a respective guide structure 304. The guide structure may form a receiver or passage 306 to guide a drill member 308 and/or a fastener along the guide axis (see FIGS. 14 and 17). Here, each guide structure includes a channel or through-bore defined by carriage 254 and a stop 310 formed by a notched ear 312 at the proximal end of frame member 252 (see FIGS. 14, 15, and 17).

FIG. 17 shows exemplary structure of the drill member. Drill member 308 may include a drill bit 314, a shaft 316 holding the drill bit, and a shoulder 318 formed proximally to the shaft. The drill member may be advanced along guide axis 302 until shoulder 318 contacts stop 310, to block further axial advancement of the drill member. For example, the drill member may be configured to drill to a predefined position, with respect to distal jaw 274, along the guide axis. The predefined position may, for example, extend into and/or through distal aperture 112 of the distal mounting portion, but not excessively beyond the distal aperture, to avoid damaging soft tissue, such as a lung, which may be present behind the distal aperture.

Stop 310 may be fixed to distal jaw 274, such that the stop remains at a fixed distance from distal jaw 274 as the spacing of the jaws is changed by turning drive screw 264. Accordingly, drill member 308 can advance only to the predefined position along the guide axis for any separation of the jaws and any extent of clip collapse. With this arrangement, the same drill member and bit position can be used to drill through bones or bone regions of various sizes (e.g., thicker and thinner regions of rib bones), without the need to pre-measure the bone or bone region and without concern that the drill member will cause injury by advancing too deeply into soft tissue.

Tool 250 also may provide a gauge 330 to facilitate selection of an appropriate size (length) of fastener according to how much the clip has been collapsed (see FIGS. 15 and 16). The appropriate length of fastener is determined by the separation of the mounting portions from each other, such as after the clip has been collapsed to conform the clip to the bone. Without proper selection of fastener length, the fastener either will be too short to reach and attach to the distal mounting portion, or will be too long and will project unnecessarily far past the distal mounting portion. In any event, the gauge can measure a linear dimension corresponding to a separation distance of the jaws, which represents the transverse dimension of the clip. The gauge may present the measurement to the user in any suitable form, such as a number(s) or other alphanumeric character(s) or symbol(s), a mark on a scale, a bone screw characteristic (e.g., a color or length (such as in millimeters)), a combination thereof, or the like.

The gauge may include an array of indicia or markings 332, which may form a scale, and also may include an indicator or reference mark 334 that is alignable serially with markings of the indicia. Indicia 332 may be provided by carriage 254 and reference mark 334 by frame member 252, or vice versa. Relative movement of the carriage and frame member along compression axis 256 causes the reference mark to travel along the indicia (or vice versa). The indicia may include lines or dots, alphanumeric characters or other symbols, distinctly colored marks, or the like. In the depicted embodiment, the indicia include numbers corresponding to fastener lengths (namely 6, 8, 10, 12, and 14 millimeters). Also, the indicia include a loading mark 336 and text ("LOAD") to indicate a loading position for the tool to receive a clip. Indicia 332 and reference mark 334 may be visible from above the tool and from one or both sides. Here, the tool has two copies of indicia 332 and reference mark 334 to permit the user to read a gauge configuration from either side of the tool (see FIG. 16).

In some embodiments, the indicia may include color coding to present the measurement as a color. In some embodiments, the indicia may include letters that form color names (e.g., brown, blue, green, pink, and gold, among others) or color abbreviations (e.g., BRN, BLU, GRN, PNK, GLD). The color (or other indicia feature) may identify an appropriate length of fastener to be used, with the fastener itself optionally being color-coded to match one of the colors of the indicia. A set of bone screws of corresponding colors may be provided, for example, with blue screws having a length corresponding to the measurement reflected by the blue mark of the gauge, green screws having a length corresponding to the measurement reflected by the green mark of the gauge, and so on. In this way, a surgeon can easily match the color read from gauge 330 with the color of a bone screw of suitable length for spanning a pair of mounting portions and/or the collapsed clip.

Further aspects of installation tools and their use with mounting portions and fasteners are described elsewhere in the present disclosure, such as in Sections III, IV, and VI, among others.

III. BONE FIXATION SYSTEM WITH DISCRETE CLIPS AND/OR MOUNTING PORTIONS

This section describes exemplary bone fixation systems that utilize discrete clips and/or discrete mounting portions to secure a spanning portion and/or plate member to bone; see FIGS. 18-26.

FIG. 18 shows selected aspects of an exemplary bone fixation system 350 including a fixation device 352 having discrete clips 66 and a plate member 354 (interchangeably termed a plate). Plate member 354 may have any of the structures and features described above for spanning portion 56 of fixation device 52 (e.g., see FIGS. 1 and 2), and may provide at least one spanning portion 56 of the fixation device. Also, the clips function generally as described above for clips 60 (see Section I). Accordingly, each clip 66 may have any of the structures and features disclosed elsewhere herein for integral clips. For example, each clip 66 may have a proximal mounting portion 100 defining one or more proximal apertures 356 and a distal mounting portion 102 defining one or more distal slots 112, and connected by a collapsible portion 104 of the clip. Apertures 356 are aligned with respective slots 112 and may be nonlocking.

Clips 66 are distinct from integral clips 60 described above. Proximal mounting portion 100 is not connected integrally to spanning portion 56 of plate member 354. Instead, proximal mounting portion 100 of the clip overlaps plate member 354 to receiver a fastener 64 that extends through proximal aperture 356 and one of apertures 70. Accordingly, proximal mounting portion 100 and a selectable linkage region 358 of plate member 354 are abutted to form an overlapped mounting portion 360 of the fixation device. For example, in the depicted embodiment, linkage region 358 of plate member 354 can be provided by any section along the plate member having a pair of adjacent apertures 70 (two potential linkage regions 358 are identified in FIG. 18). Thus, discrete clip 66 can be positioned at a plurality of interchangeable positions along the plate member, to permit a surgeon to position each clip at a suitable position along bone where more robust anchorage is desired.

The apertures of the clip and the selected linkage region 358 can be aligned with one another using the apertures themselves and/or via alignment features provided by the clip and the linkage region, optionally with the aid of a tool as described below. For example, a pair of opposing indentations 84 of plate member 354 may be aligned with a pair of opposing indentations 362 of the clip.

FIG. 19 shows a sectional view taken through aligned apertures (112, 356) of clip 66. The clip may define a pocket 370 shaped to receive plate member 354 when the clip is abutted with the plate member.

Figure 20:
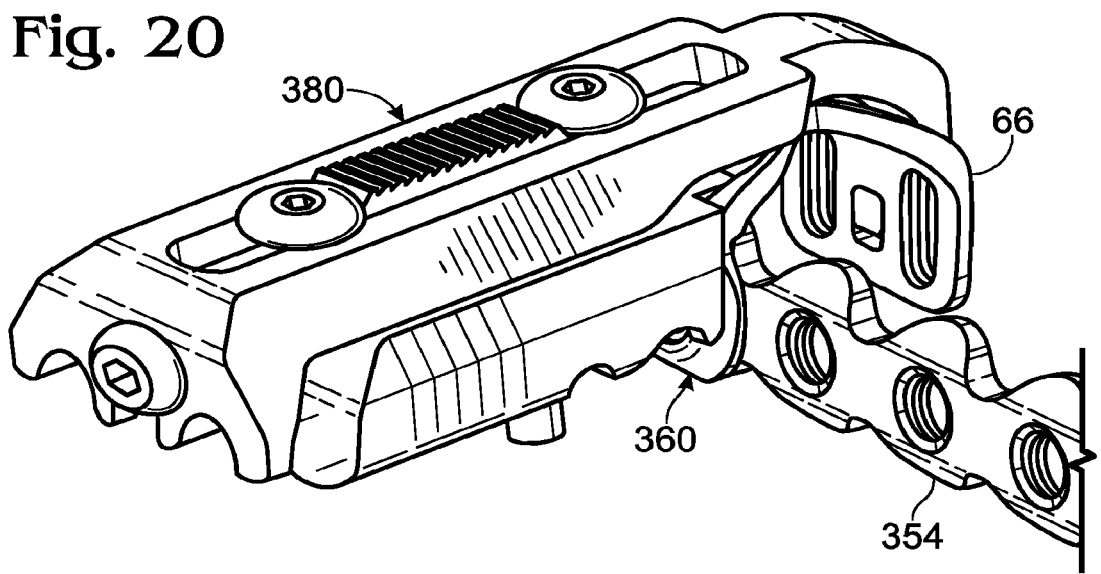
FIG. 20 is an isometric view of another exemplary installation tool attached to one of the clips and the plate member of the fixation device of FIG. 18, in accordance with aspects of the present disclosure.

FIG. 20 shows an installation tool 380 operatively attached to clip 66 and plate member 354. Tool 380 may have any suitable combination of the devices, mechanisms, and features disclosed in Section II for tool 250. However, tool 380 is modified to engage and attach clip 66 and plate member 354, and particularly overlapped portion 360, of fixation device 352 to the tool.

FIGS. 21 and 22 show side and sectional views of tool 380 attached to overlapped portion 360 formed by proximal mounting portion 100 of clip 66 and linkage region 358 of plate member 354. Tool 380 has a fixed retainer or bracket 382 and a movable retainer or bracket 384 that cooperate to align and secure proximal overlapped portion 360 to the proximal jaw of the tool. The retainers collectively attach the plate member and clip to carriage 254. Fixed retainer 382 projects from the carriage and is received in aligned upper indentations 84, 362 of the plate member and clip (also see FIG. 18). The fixed retainer has a lip or flange 386 that extends to an inner side of plate member 354 and forms a recess sized to receive an edge region at the aligned upper indentations. Movable retainer 384 may include a movable lip or flange 388 that can be pivoted, via a user control, such as a lever 390, to a position overlapping plate member 354, to lock overlapped portion 360 to the proximal jaw of the tool. Each retainer can act as a datum to position the plate member and mounting portion and restrict their movement.

FIGS. 23 and 24 show the tool with movable retainer 384 pivoted to an unlocked or released configuration. Flange 388 no longer restricts removal of overlapped portion 360. Also, lever 390 follows an angled track 392 such that movable retainer 384 is retracted toward carriage 254 to facilitate removal of the clip and plate member from the tool. The jaws of the tool may be moved farther apart to facilitate removal.

FIG. 25 shows selected aspects of another exemplary bone fixation system 400 with mounting portions that opposingly engage bone. System 400 includes a fixation device 401 having a plate member 354 and mounting portions 402, 404. Each of mounting portions 402, 404 is provided by a mounting element that is discrete from plate member 354. The mounting portion may have one or more apertures with fastener-attachment structure, such as a locking slot 112. (Mounting portion 404, with only one locking slot 112, interchangeably may be termed a locking washer.)

Each mounting portion, 402 or 404, may be selectably aligned with a linkage region 358 or 406 defining one or more apertures 70. In the depicted embodiment, mounting portion 402, which has two slots 112, can be interchangeably aligned with a plurality of linkage regions 358 each defining a pair of apertures 70. Also, mounting portion 404 can be interchangeably aligned with each aperture 70 of the plate member.

An installation tool 410 may be utilized to align mounting portion 402 or 404 with a desired linkage region 358 or 406, respectively, and particularly to align one or more selected apertures 70 with one or more apertures (e.g., slots 112) of the mounting portion on one or more fastener receiving axes 130. In other words, tool 410 positions mounting portion 402 or 404 in alignment with a selected aperture(s) of the plate member, to permit placement of a fastener through a bone and extending from aperture 70 to the distal aperture (e.g., slot 112) and into locked engagement with the distal aperture (e.g., slot 112), and, optionally, aperture 70.

Tool 410 may be configured to be attached to linkage region 358 or 406 in a predefined alignment of a proximal jaw of the tool and the linkage region. The tool may, for example, use an attachment mechanism described above for tool 250 or tool 380, among others. (If tool 250 is used, plate member 354 may be modified to include openings for alignment with or attachment to the proximal jaw.)

FIGS. 25 and 26 show further aspects of tool 410. The tool also may be configured to be attached to mounting portion 402 or 404. For example, the tool may have a distal jaw 412 that receives and engages mounting portion 402. When received and engaged, the apertures of mounting portion 402 are aligned with respective apertures 70 of the plate member. The distal jaw may define a receiver region 414 into which mounting portion can be placed (e.g., snap-fitted). The receiver region may be formed by a distal wall 415, lateral boundary bars 416, and resilient retainers 418. Retainers 418 may prevent mounting portion 402 from contacting bone until after the mounting portion is removed from the distal jaw. Accordingly, the distal jaw may engage bone when the tool is clamped on bone. Retainers 418 may be sufficiently flexible to permit mounting portion 402 to be released from the distal jaw after a fastener is attached to the mounting portion, by urging the distal jaw away from bone (e.g., by opening the jaws of the tool). In other embodiments, mounting portion 402 (or 404) may be held in place by a retainer that may be adjusted remotely from the proximal end of tool 410. For example, the retainer may be operatively connected to a control cable or rod, among others, to permit a surgeon to control release after fastener placement.

Further aspects of discrete clips and/or mounting portions and their installation on bone are described elsewhere in the present disclosure, such as in Sections I, IV, and VI, among others.

IV. METHODS OF BONE FIXATION WITH OPPOSED MOUNTING PORTIONS

This section describes exemplary methods of fixing bone with a fixation device that includes a collapsible clip and/or a pair of discrete mounting portions. The steps described in this section may be performed in any suitable order and combination and with any of the apparatus, features, or approaches described elsewhere in the present disclosure.

A bone may be selected for fixation. Any suitable bone (or bones for a fusion procedure) may be selected. Accordingly, the bone may be a long bone or another bone of a skeleton. The bone selected may be a rib bone, a clavicle, a sternum, a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a scapula, a pelvic bone, a vertebra, a mandible, a cranial bone, and/or the like.

The selected bone may have a discontinuity. The discontinuity may be a pre-existing discontinuity present before surgery and/or a discontinuity introduced during performance of a method of bone fixation. Accordingly, the method may include a step of introducing a discontinuity into the selected bone, such as by cutting or breaking the bone. The bone may have any suitable condition to be treated, including a fracture, a cut, a malunion, a nonunion, a structural weakness, an undesirable length and/or angulation, and/or the like. The condition may affect any suitable portion of the bone, such as a diaphyseal (shaft or central) and/or a metaphyseal (end) region of the bone (e.g., a proximal or distal end region of a long bone). In exemplary embodiments, the selected bone may be a fractured rib bone, a fractured rib bone and sternum, a cut sternum, a pair of fractured rib bones and a sternum, or the like.

A fixation device may be selected for attachment to the bone. The fixation device may include a pair of mounting portions to be opposed with one another, at least one or a pair of clips, a spanning portion, or any combination thereof. The mounting portion and/or fixation device may be configured to be disposed on bone. For example, the mounting portion/ fixation device may be formed of a biocompatible material and may be shaped and/or treated to ensure functionality on bone, to reduce the chance of infection, and to limit discomfort to the recipient, among others. The fixation device also may include at least one separate fastener, such as a bone screw, that will be used to attach the fixation device to bone. Selection of the fastener may be performed after selection of the fixation device, such as after a pair of mounting portions are urged closer to each other and/or after a clip of the fixation device is conformed to a region of the selected bone. The mounting portions and/or other system components each may be described as being proximal or distal. These terms generally indicate relative proximity to a user (e.g., a surgeon), unless specified otherwise.

The fixation device may be connected to an installation tool. The installation tool may include any combination of the devices, mechanisms, and/or features described above in Sections II and III and below in Section VI or elsewhere in the present disclosure. In some cases, a distinct installation tool may be attached to each clip and/or pair of mounting portions selected. For example, if a fixation device with a pair of clips is selected, a pair of installation tools may be attached to the device with each tool operatively engaged with one of the clips. The installation tools may be copies of the same tool or may be different tools. Connection of an installation tool to a clip (or pair of mounting portions) may be performed before or after the clip is disposed on bone. If performed before the clip is disposed on bone, the tool(s) and fixation device (or one or more components thereof) may be connected off bone to form an installation assembly that can be placed onto bone as a unit.

Connection of a pair of discrete mounting portions to an installation tool may be performed before, after, or a combination of before and after the mounting portions are disposed on bone. For example, a distal mounting portion of the pair may be connected to the tool before the distal mounting portion is disposed on bone, and a proximal mounting portion of the pair may be connected to the tool after the proximal mounting portion is disposed on and/or connected to bone. In some cases, a proximal mounting portion may be selected for connection to the tool from a plurality of potential mounting portions (linkage regions) offered by a plate member, which may (or may not) already be disposed on bone.

The fixation device may be contoured according to the bone selected. For example, a spanning portion of a selected fixation device may be modified by deforming (e.g., bending) the spanning portion to better match the longitudinal curvature, if any, of the selected bone. Contouring the spanning portion may be performed before or after an installation tool is connecting to mounting portions of the fixation device. In some cases, the spanning portion may be contoured with a pair of bending tools disposed in threaded engagement with the spanning portion.

The fixation device may be disposed on (i.e., placed adjacent and/or against) the selected bone. For example, a clip may be placed on the bone with mounting portions of the clip disposed across the bone from each other. Alternatively, or in addition, a pair of discrete mounting portions may be arranged across the selected bone from each other, with each mounting portion on bone (i.e., placed adjacent and/or against the bone). In some cases, a clip may be placed on a rib bone with a collapsible portion of the clip disposed on a superior surface region of the rib bone and with the mounting portions of the clip disposed on respective, opposing inner and outer sides of the rib bone (i.e., generally intermediate the superior and inferior sides of the rib bone). In some cases, a pair of discrete mounting portions may be disposed on respective outer and inner sides of a rib bone. In some cases, a proximal mounting portion and/or a spanning portion may be arranged adjacent and/or against an outer surface region of a rib bone. In any event, a clip and/or mounting portions may be placed on the bone before or after the separation distance of the mounting portions of a clip has been decreased (e.g., before the clip has been collapsed to any significant extent).

Mounting portions of the fixation device may be urged toward each other with jaws of the tool. Urging the mounting portions toward each other may deform a clip that provides the mounting portions and/or may decrease a separation distance between the mounting portions. One or both of the mounting portions may move closer to the bone. Urging the mounting portions toward each other may clamp the tool to the bone, with the jaws of the tool disposed on opposing sides of the bone. One or both of the jaws may engage the bone directly or may clamp to the bone without contacting the bone directly. Accordingly, neither, one, or both mounting portions may be urged by the tool into engagement with the bone. In some cases, at least one of the mounting portions may be held out of contact with the bone by the structure of an associated jaw of the tool (e.g., see FIGS. 25 and 26).

One or more holes may be formed in the bone coaxial with one or more fastener-receiving axes defined by aligned apertures of the mounting portions. The holes may be formed while the position of the tool and/or mounting portions is fixed with respect to the bone, due to the clamped arranged of the tool on bone. Formation of the holes may be guided by a guide of the tool.

One or more fasteners may be selected for placement into the one or more holes formed in bone. Selection of the fasteners may be based on a configuration provided by a gauge of the tool, while the tool is clamped on the bone. In some cases, a pair of fasteners having the same length may be selected for placement into two pairs of aligned apertures of the mounting portions based on the same configuration of the gauge.

Each selected fastener may be placed through a proximal aperture defined by a proximal mounting portion, through a hole formed in bone, and into a distal aperture defined by a distal mounting portion. In some cases, the fastener may be received in a pair or at least three aligned apertures of the fixation device. The fastener may be attached to any combination of these aligned apertures. Any combination of the apertures thus may include a pre-formed attachment structure, such as at least one internal thread or an at least one substantially linear ridge configured to be engaged with an external thread of the fastener. Alternatively, at least one aperture may be modified by placement of the fastener such that an internal thread is created in one or more walls of the aperture by the external thread of the fastener. The internal thread may be created by deforming and/or cutting one or more walls of the aperture. The fastener may be placed into the proximal aperture of a proximal mounting portion, through bone, and into engagement with the distal aperture while both mounting portions remain connected to the tool. Securing of the mounting portions to the bone with the fastener(s) may be performed and completed while the tool is still connected to both mounting portions. Alternatively, the fastener may be turned additionally after one or both mounting portions are disconnected from the tool. Additional apertures of the fixation device also may receive fasteners to further secure the device to bone.

In some cases, a rib fixation device may be secured to at least two bones. For example, a fixation device including a spanning portion and at least two clips may be secured to a pair of ribs disposed on opposite sides of the sternum (e.g., the ribs may be detached from the sternum due to cartilage damage), with one clip attached to each rib. The spanning portion of the fixation device may span the sternum. The spanning portion may be attached to the sternum with one or more fasteners placed into the sternum.

Further aspects of methods of fixing bone are described elsewhere in the present disclosure, such as in Sections II, III, and VI, among others.

V. EXEMPLARY SYSTEM COMBINATIONS

The apparatus disclosed herein may be utilized and/or grouped in any suitable manner to provide a system, which may be supplied as a kit. The system (or kit) may include any combination of the following: one or more mounting portions, one or more clip members, one or more bone plates each including a pair of clip members and a spanning portion (e.g., a plate member) that is connected integrally to or is separate from the clip members, and a plurality of fasteners to attach the mounting portions and/or clip members and/or spanning portions to bone. The system also or alternatively may include any combination of the following: an installation tool having any combination of the devices and/or mechanisms disclosed in Section II, one or more clamps to engage and hold a spanning portion on bone during installation, one or more bending tools (e.g., rods) capable of being disposed in threaded engagement with the spanning portion, and instructions for use of system components for installation of the mounting portions, clip members, spanning portions, and/or bone plates. In some cases, the plurality of fasteners may include a set of fasteners of different length and appropriate for different extents of collapse of a clip member and/or different separation distances of a pair of discrete mounting portions. Different fasteners of the set may correspond to distinct configurations of a gauge provided by the installation tool. Each system component may be configured for single use (e.g., mounting portions, clips, bone plates, and fasteners) or for multiple use (e.g., the installation tool).

Some or all of the components of each system (or kit) may be provided in a sterile condition, such as packaged in a sterile container.

VI. EXAMPLES

The following examples describe selected aspects and embodiments of the present disclosure related to fixation devices with opposed mounting portions and/or a mounting portion with a slot, tools for installing the fixation devices, and methods of bone fixation. These examples are included for illustration and are not intended to limit or define the entire scope of the present disclosure.

Example 1. Exemplary Clip Collapse with an Installation Tool

Figure 27:
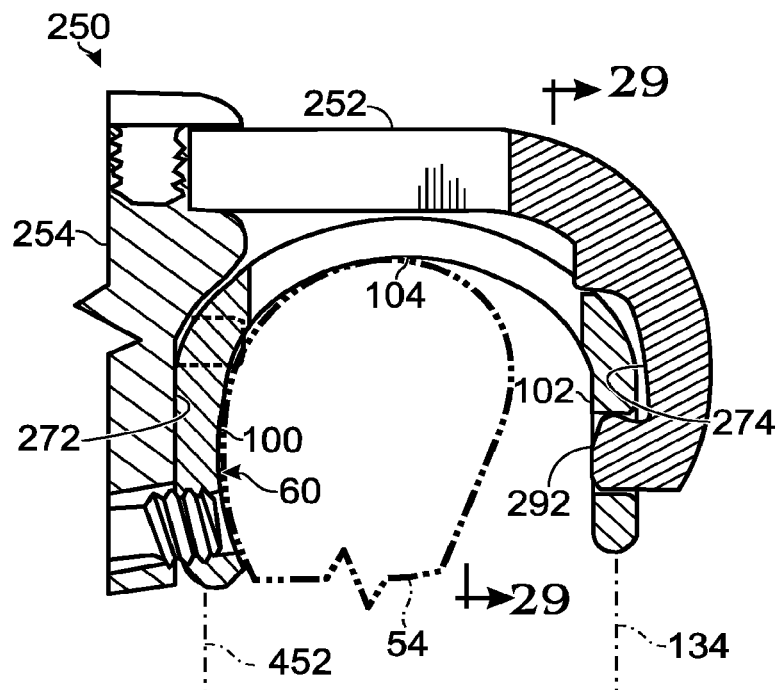
FIG. 27 is a fragmentary, sectional view of the distal region of the installation tool of FIG. 14 attached to a clip that is disposed on a bone (in phantom), taken as in FIG. 17.
Figure 28:
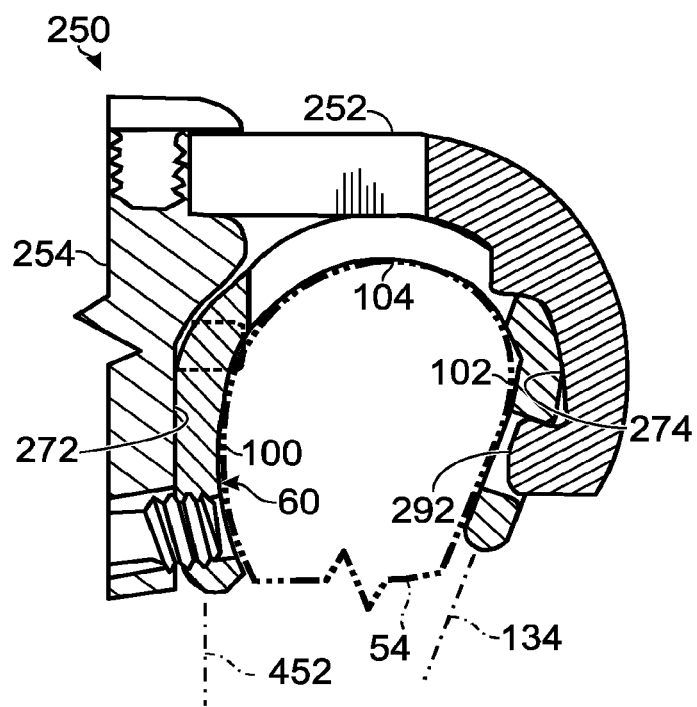
FIG. 28 is another fragmentary, sectional view of the distal region of the installation tool of FIG. 14, taken as in FIG. 27 after the clip has been collapsed and illustrating how the distal mounting portion of the clip has pivoted with respect to the proximal mounting portion of the clip and the distal jaw of the tool.
Figure 29:
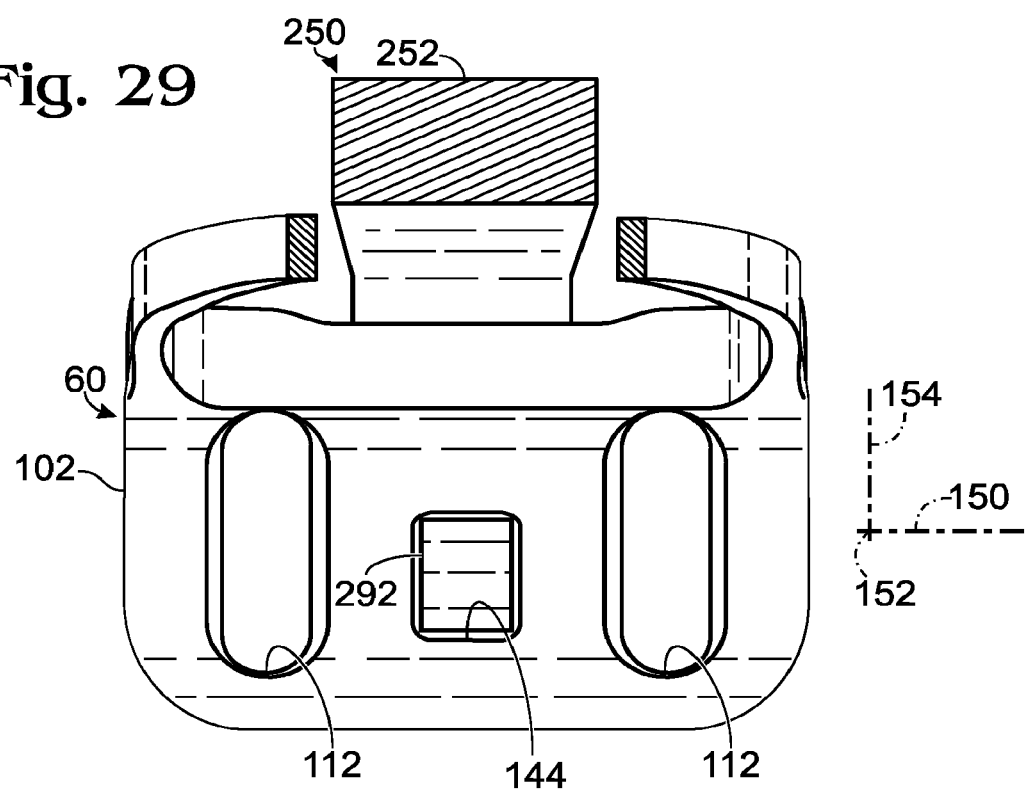
FIG. 29 is a sectional view of the tool and clip of FIG. 27, taken generally along line 29-29 of FIG. 27 toward the distal mounting portion of the clip and the distal jaw of the tool.

This example describes further aspects of tool 250 and clip 60 (see Sections I and II), particularly an exemplary configuration produced by collapsing the clip with jaws 272, 274 of the tool; see FIGS. 27-29.

FIGS. 27 and 28 shows tool 250 attached to and operatively engaged with clip 60 respectively before and after the clip has been collapsed against bone 54 by the clamping device of the tool. FIG. 27 shows proximal and distal mounting portions 100, 102 defining respective planes 452, 134 that are parallel to each other. In other embodiments, planes 452, 134 may be inclined from parallel to each other by any suitable angle. In the depicted configuration, proximal mounting portion 100 is placed against bone before the clip is collapsed. However, in other configurations, the mounting portions may be spaced more equally from the bone before collapse, or the distal mounting portion may be closer to the bone. FIG. 28 shows distal mounting portion 102 angled inward such that distal plane 134 has pivoted from its parallel configuration with proximal plane 452 in FIG. 27. The distal mounting portion has pivoted about one or more axes parallel to the through-axis defined by the clip, to orient the distal mounting portion more parallel and/or tangential to a surface region of bone 54 against which the distal mounting portion is urged by the jaws of the tool.

FIGS. 27 and 29 show orthogonal views of distal alignment member or tooth 292 provided by distal jaw 274. The tooth and corresponding receptacle 144 of the distal mounting portion are each shaped to selectively permit and restrict pivotal motion of the distal mounting portion about the tooth with respect to distinct orthogonal axes. In particular, the tooth may be curved, as shown in FIG. 27, to permit pivotal motion of the distal mounting portion at receptacle 144, about one or more axes parallel to the through-axis. The shape of the distal jaw adjacent tooth 292 and/or the tooth itself may determine whether and how far the distal mounting portion can pivot (i.e., the maximum pivot angle permitted). In any event, as shown in FIG. 29, tooth 292 may be shaped to restrict pivotal motion of the distal mounting portion at receptacle 144 with respect to axes parallel to transverse axis 152 and bone-receiving axis 154 defined by the clip (e.g., see FIGS. 4-6). For example, in the depicted embodiment, the tooth is rectangular and is received in a generally rectangular receptacle 144.

Pivotal motion of the distal mounting portion may be encouraged by the orientation of a rib surface region against which the distal mounting portion is abutted during collapse of the clip. For example, a concave inner surface region of a rib bone may urge the distal mounting portion into the angled configuration shown in FIGS. 9 and 28.

Example 2. Selected System Embodiments—Clip with Collapsible Portion

This example describes selected system embodiments of the present disclosure related to a clip having a collapsible portion, presented as a series of indexed paragraphs.

1. A system for bone fixation, comprising: (A) a clip including first and second mounting portion and a selectively collapsible portion connecting the mounting portions, the mounting portions respectively defining a first aperture and a second aperture that are aligned with each other, the mounting portions and the collapsible portion collectively defining a cavity configured to receive a bone such that the mounting portions opposingly flank the bone and an axis defined collectively by the first and second apertures extends through the received bone from the first aperture to the second aperture.

2. The system of paragraph 1, wherein the collapsible portion is configured to fold at one or more predefined sites as the clip members are urged toward each other.

3. The system of paragraph 1, wherein the collapsible portion includes at least one strap, wherein a central axis of the clip extends through the collapsible portion and between the clip members, and wherein an orthogonal projection of the at least one strap onto a plane oriented orthogonal to the central axis has a serpentine shape.

4. The system of paragraph 1, wherein the collapsible portion includes a pair of straps.

5. The system of paragraph 1, wherein the clip defines a central axis extending through the collapsible portion and between the clip members, and wherein a height of the clip measured parallel to the central axis does not change substantially when the mounting portions are moved closer to each other.

6. The system of paragraph 1, wherein the clip defines a through-axis along which the received bone is configured to extend, wherein an orthogonal projection of the clip onto a plane that is orthogonal to the through-axis extends along a path having a length, and wherein the length of the path decreases as the mounting portions are urged closer together.

7. The system of paragraph 1, wherein clip defines a through-axis, and wherein the collapsible portion is configured to deform selectively as the mounting portions are urged toward each other without substantially buckling away from the through-axis.

8. The system of paragraph 1, wherein the collapsible portion defines an opening, and wherein a size and a shape of the opening change when the mounting portions are urged toward each other.

9. A system for bone fixation, comprising: a clip including first and second mounting portions each defining at least one aperture to receive a fastener and connected by a collapsible portion, the clip being at least generally U-shaped in profile, wherein urging the mounting portions toward each other causes the collapsible portion to fold such that a path length of the clip decreases, as measured in profile from one mounting portion to the other mounting portion.

10. The system of paragraph 9, wherein the collapsible portion includes a strap that follows a serpentine path.

11. The system of paragraph 9, further comprising a base plate defining a plurality of apertures, wherein the base plate is configured to be disposed between one of the mounting portions and bone with one or more apertures of the base plate coaxially arranged with one or more apertures of the one mounting portion.

12. The system of paragraph 11, wherein the base plate is configured to be disposed with a pair of apertures of the base plate arranged coaxially with a pair of apertures of the one mounting portion.

13. The system of paragraph 12, wherein the clip is a first clip, further comprising a second clip configured to be overlapped with the base plate.

14. The system of paragraph 9, further comprising a bone plate including a spanning portion, the clip has a first mounting portion connected integrally to the spanning portion, and a second mounting portion connected integrally to the spanning portion.

15. A tool for installation of a clip on bone, comprising: (A) a body; (B) a holder device that fastens a clip to the body; and (C) a clamp device configured to apply adjustable compression to the attached clip.

16. The tool of paragraph 15, further comprising a guide device defining one or more bores that are coaxial to one or more apertures of the clip when clip is fastened to the body.

17. The tool of paragraph 15, further comprising a gauge that measures a dimension corresponding to a distance between mounting portions of the clip.

Example 3. Selected Methods

This example describes selected methods of the present disclosure, presented as a series of indexed paragraphs.

1. A method of fixing bone, the method comprising: (A) connecting a first mounting portion and a second mounting portion of a fixation device to an installation tool; (B) disposing the first mounting portion and the second mounting portion across a bone from each other; (C) urging the first and second mounting portions toward each other with jaws of the tool such that the tool is clamped to the bone; and (D) securing the first and second mounting portions to the bone with a fastener extending from a first aperture defined by the first mounting portion, through the bone, and into a second aperture defined by the second mounting portion.

2. The method of paragraph 1, wherein the fixation device includes a spanning portion, and wherein the spanning portion extends along the bone from the first mounting portion after the mounting portions are secured to the bone.

3. The method of paragraph 2, wherein the spanning portion spans a discontinuity in a rib bone after the step of securing.

4. The method of paragraph 2 or 3, wherein the spanning portion is continuous with the first mounting portion, and optionally continuous with the second mounting portion.

5. The method of paragraph 4, wherein the spanning portion and the first mounting portion are provided by a same plate member of the fixation device.

6. The method of paragraph 2 or 3, wherein the spanning portion and the first mounting portion are provided by discrete pieces of the fixation device.

7. The method of paragraph 6, wherein, after the step of securing, the spanning portion overlaps the first mounting portion and the fastener extends through an aperture defined by the spanning portion.

8. The method of any of paragraphs 2 to 7, wherein the spanning portion and the second mounting portion are provided by discrete pieces of the fixation device.

9. The method of any of paragraphs 2 to 8, wherein the spanning portion spans a discontinuity in the bone after the step of securing.

10. The method of any of paragraphs 2 to 9, wherein the spanning portion is provided by a plate member.

11. The method of any of paragraphs 1 to 10, wherein the first mounting portion and the second mounting portion are provided by discrete pieces of the fixation device.

12. The method of any of paragraphs 1 to 5 and 8 to 11, wherein the fixation device includes a clip member, and wherein the clip member includes the first mounting portion connected to and facing the second mounting portion.

13. The method of paragraph 12, wherein a collapsible portion of the clip member interconnects the first and second mounting portions, and wherein the step of urging folds the collapsible portion.

14. The method of paragraph 13, wherein the collapsible portion includes an elongate web member that folds at one or more predefined sites along the web member when the step of urging folds the collapsible portion.

15. The method of paragraph 13 or 14, wherein the collapsible portion includes a pair of elongate web members each separately interconnecting the first and second mounting portions.

16. The method of any of paragraphs 1 to 15, wherein the tool is connected to the mounting portions before the mounting portions are disposed across a bone from each other.

17. The method of any of paragraphs 1 to 16, wherein the step of connecting includes a step of fixedly attaching a mounting portion to one of the jaws.

18. The method of paragraph 17, wherein the jaws include a proximal jaw and a distal jaw, and wherein the step of connecting fixedly attaches the first mounting portion to the proximal jaw.

19. The method of any of paragraphs 1 to 18, wherein a same fastener-receiving axis extends through the first aperture and the second aperture after the mounting portions are connected to the installation tool.

20. The method of paragraph 19, wherein the tool is configured to apply compressive force parallel to a compression axis with the jaws, and wherein the fastener-receiving axis is parallel to the compression axis after the mounting portions are connected to the tool.

21. The method of paragraph 20, wherein the fastener-receiving axis remains parallel to the compression axis during the step of urging.

22. The method of any of paragraphs 19 to 21, wherein the first and second mounting portions are discrete from each, and wherein the step of connecting aligns the first and second apertures on the fastener-receiving axis.

23. The method of any of paragraphs 19 to 22, wherein a separation distance between the mounting portions is decreased by the step of urging, and wherein the fastener-receiving axis remains parallel to the compression axis as the separation distance decreases.

24. The method of any of paragraphs 1 to 23, wherein the tool is configured to apply compressive force parallel to a compression axis with the jaws, and wherein the step of connecting the mounting portions to the tool places each mounting portion at a predefined position along an axis orthogonal to the compression axis.

25. The method of paragraph 24, wherein the step of connecting the mounting portions to the tool places each mounting portion at a predefined position along each of a pair of axes orthogonal to each other and the compression axis.

26. The method of any of paragraphs 1 to 25, wherein the step of connecting the mounting portions to the tool includes a step of mating (a) an alignment projection of one of the tool and a mounting portion and (b) an alignment opening of the other of the tool and such mounting portion.

27. The method of paragraph 26, wherein the step of connecting includes a step of mating distinct alignment projections of the tool with an alignment opening of each mounting portion.

28. The method of any of paragraphs 1 to 27, wherein the step of connecting the mounting portions to the tool includes a step of creating engagement between one or more alignment features of the tool and one or more alignment features of one or both mounting portions.

29. The method of any of paragraphs 1 to 28, wherein at least one of the mounting portions is engaged with the bone when the tool is clamped to the bone.

30. The method of any of paragraphs 1 to 29, wherein at least one of the jaws of the tool is not directly engaged with the bone when the tool is clamped to the bone.

31. The method of any of paragraphs 1 to 30, wherein the step of urging pivots the second mounting portion with respect to the first mounting portion.

32. The method of paragraph 31, wherein the jaws include a distal jaw, and wherein the second mounting portion pivots with respect to the distal jaw when the second mounting portion pivots with respect to the first mounting portion.

33. The method of any of paragraphs 1 to 32, wherein the first aperture defines a fastener-receiving axis, wherein the second aperture is a slot defining a fastener-receiving plane that is coplanar with the fastener-receiving axis after the mounting portions are connected to the tool, and wherein the second mounting portion is connected to the tool such that the second mounting portion is capable of pivoting about one or more axes orthogonal to the fastener-receiving plane during the step of urging if such pivoting renders the second mounting portion more tangential and/or parallel to a surface region of the bone engaged by the second mounting portion.

34. The method of any of paragraphs 1 to 33, wherein the step of securing is performed while the tool is clamped to the bone.

35. The method of any of paragraphs 1 to 34, wherein the step of securing attaches the fastener to at least one of mounting portions.

36. The method of any of paragraphs 1 to 35, wherein the step of securing separately attaches the fastener to each of the mounting portions at the first and second apertures.

37. The method of any of paragraphs 1 to 36, wherein the first and second apertures are aligned with each other on a fastener-receiving axis after the step of urging, and wherein the tool includes a guide defining a guide axis that is coaxial to the fastener-receiving axis.

38. The method of paragraph 37, wherein the first aperture defines the fastener-receiving axis, and wherein the guide axis is parallel to the fastener-receiving axis after the step of connecting and before the step of urging.

39. The method of any of paragraphs 1 to 38, wherein the first and second apertures are aligned with each other on a fastener-receiving axis after the step of urging, further comprising a step of forming a hole in the bone along the fastener-receiving axis with a hole-forming tool guided by the installation tool.

40. The method of paragraph 39, wherein the hole-forming tool is a drill, wherein the jaws include a proximal jaw that engages the first mounting portion and a distal jaw that engages the second mounting portion, wherein the installation tool includes a drill stop having a fixed separation from the distal jaw, and wherein the step of forming a hole includes a step of advancing the drill along the guide axis until advancement is blocked by the drill stop.

41. The method of any of paragraphs 1 to 40, wherein the tool includes a guide defining a guide axis, and wherein the step of securing includes a step of placing the fastener along the guide axis while the tool is clamped to the bone.

42. The method of any of paragraphs 1 to 41, wherein the tool includes a gauge, further comprising a step of selecting a fastener of appropriate length for the step of securing based on a configuration of the gauge.

43. The method of paragraph 42, wherein the gauge device includes indicia representing fasteners of different length.

44. The method of paragraph 43, wherein the indicia representing fasteners of different length include different numbers, different colors, or both.

45. A method of fixing bone, the method comprising: (A) selecting a clip member including a first mounting portion and a second mounting portion interconnected by a collapsible portion and defining respective first and second apertures; (B) connecting the clip member to an installation tool; (C) disposing the clip member on a bone with the first and second mounting portions arranged across the bone from each other; (D) applying compressive force to the clip member disposed on bone with jaws of the tool to urge the first and second mounting portions toward each other and closer to the bone; and (E) securing the first and second mounting portions to the bone with a fastener extending from the first aperture, through the bone, and into the second aperture.

46. A method of fixing bone, the method comprising: (A) connecting a first mounting portion and a second mounting portion of a fixation device to an installation tool including a gauge; (B) disposing the first mounting portion and the second mounting portion across a bone from each other; (C) urging the first and second mounting portions toward each other with jaws of the tool; (D) selecting a fastener of appropriate length based on a configuration of the gauge; and (E) securing the first and second mounting portions to the bone with the fastener extending from a first aperture defined by the first mounting portion, through the bone, and into a second aperture defined by the second mounting portion.

47. A method of fixing bone, the method comprising: (A) connecting a first mounting portion and a second mounting portion of a fixation device to an installation tool defining a guide axis, the connected first and second mounting portions respectively defining first and second apertures aligned on the guide axis; (B) disposing the first mounting portion and the second mounting portion across a bone from each other; (C) urging the first and second mounting portions toward each other with jaws of the tool; (D) forming a hole in the bone along the guide axis; and (E) securing the first and second mounting portions to the bone with a fastener extending from the first aperture, through the hole in the bone, and into the second aperture.

Example 4. Selected System Embodiments—Fixation Device and Installation Tool

This example describes selected embodiments of the present disclosure, particularly system embodiments involving (a) a fixation device including mounting portions and (b) an installation tool to facilitate installing the mounting portions on bone. The selected system embodiments are presented as a series of indexed paragraphs.

1. A system for bone fixation, comprising: (A) a fixation device including a first mounting portion and a second mounting portion configured to be arranged across a bone from each other and respectively defining a first aperture and a second aperture; and (B) an installation tool having jaws and being connectable to the first and second mounting portions such that the tool is operable to urge the first and second mounting portions toward each other with the jaws, to clamp the tool to the bone with the first aperture and the second aperture aligned with each other on a fastener-receiving axis.

2. The system of paragraph 1, wherein the fixation device includes a spanning portion, and wherein the spanning portion is configured to extend along the bone from the first mounting portion after the mounting portions are secured to the bone with a fastener extending from the first aperture, through bone, and into the second aperture.

3. The system of paragraph 2, wherein the spanning portion is continuous with the first mounting portion, and, optionally, continuous with the second mounting portion.

4. The system of paragraph 2, wherein the spanning portion and the first mounting portion are provided by discrete pieces of the fixation device.

5. The system of any of paragraphs 2 to 4, wherein the spanning portion is provided by a plate member of the fixation device. 6. The system of paragraph 5, wherein the plate member is configured to overlap the first mounting portion.

7. The system of paragraph 5, wherein the first mounting portion and the spanning portion are provided by the plate member.

8. The system of any of paragraphs 2 to 7, wherein the spanning portion and the second mounting portion are provided by discrete pieces of the fixation device.

9. The system of any of paragraphs 1 to 8, wherein the first mounting portion and the second mounting portion are provided by discrete pieces of the fixation device.

10. The system of any of paragraphs 1 to 8, wherein the fixation device includes a clip member, and wherein the clip member includes the first mounting portion connected to and facing the second mounting portion.

11. The system of paragraph 10, wherein a collapsible portion of the clip member interconnects the first and second mounting portions, and wherein the collapsible portion is configured to fold when the mounting portions are urged toward each other.

12. The system of paragraph 11, wherein the collapsible portion includes an elongate web member configured to fold at one or more predefined sites along the web member when the mounting portions are urged toward each other.

13. The system of paragraph 12, wherein the collapsible portion includes a pair of elongate web members each separately interconnecting the first and second mounting portions.

14. The system of any of paragraphs 1 to 13, wherein the tool is connectable to the mounting portions before the mounting portions are arranged across a bone from each other.

15. The system of any of paragraphs 1 to 14, wherein the jaws include a proximal jaw and a distal jaw, and wherein the first mounting portion is fixedly attachable to the proximal jaw.

16. The system of any of paragraphs 1 to 15, wherein the tool is configured to apply compressive force parallel to a compression axis with the jaws, and wherein the fastener-receiving axis is parallel to the compression axis after the mounting portions are connected to the tool.

17. The system of paragraph 16, wherein a separation distance between the mounting portions is decreased as the mounting portions are urged toward each other, and wherein the tool is configured to keep the fastener-receiving axis parallel to the compression axis as the separation distance decreases.

18. The system of any of paragraphs 1 to 17, wherein the tool is configured to apply compressive force parallel to a compression axis with the jaws, and wherein the tool is configured to be connected to the mounting portions such that each mounting portion is disposed at a predefined position along an axis orthogonal to the compression axis.

19. The system of paragraph 18, wherein the tool is configured to be connected to the mounting portions such that each mounting portion is disposed at a predefined position along each of a pair of axes orthogonal to each other and the compression axis.

20. The system of any of paragraphs 1 to 19, wherein the tool is configured to be connected to the mounting portions with (a) an alignment projection of one of the tool and a mounting portion disposed in (b) an alignment opening of the other of the tool and such mounting portion.

21. The system of any of paragraphs 1 to 20, wherein the tool is configured to be connected to the mounting portions with an alignment projection of the tool disposed in an alignment opening of a mounting portion.

22. The system of paragraph 21, wherein the tool is configured to be connected to the mounting portions with a distinct alignment projection of the tool disposed in an alignment opening of each mounting portion.

23. The system of any of paragraphs 1 to 22, wherein the tool is configured to be connected to the mounting portions in a predefined alignment of the jaws with the mounting portions 24. The system of any of paragraphs 1 to 23, wherein at least one of the mounting portions is engaged with the bone when the tool is clamped to the bone.

25. The system of any of paragraphs 1 to 24, wherein at least one of the jaws of the tool is not directly engaged with the bone when the tool is clamped to the bone.

26. The system of any of paragraphs 1 to 25, wherein the second mounting portion is configured to be pivotable with respect to the first mounting portion as the second mounting portion is urged against the bone.

27. The system of paragraph 26, wherein the jaws include a distal jaw, and wherein the second mounting portion pivots with respect to the distal jaw when the second mounting portion pivots with respect to the first mounting portion.

28. The system of paragraph 26 or 27, wherein the mounting portions are provided by a clip member, and wherein the clip member deforms when the second mounting portion pivots with the respect to the first mounting portion.

29. The system of any of paragraphs 26 to 28, wherein the jaws include a proximal jaw and a distal jaw, wherein the second mounting portion is configured to be engaged with the distal jaw, and wherein the second mounting portion is configured to pivot with respect to the distal jaw when the second mounting portion pivots with respect to the first mounting portion.

30. The system of any of paragraphs 1 to 29, wherein the first aperture defines the fastener-receiving axis, wherein the second aperture is a slot defining a fastener-receiving plane that is coplanar with the fastener-receiving axis after, and optionally before, the mounting portions are connected to the tool, and wherein the second mounting portion is connected to the tool such that the second mounting portion is capable of pivoting about one or more axes orthogonal to the fastener-receiving plane when the second mounting portion is urged against a surface region of the bone if such pivoting renders the second mounting portion more tangential and/or parallel to the surface region.

31. The system of any of paragraphs 1 to 30, wherein the tool is configured to guide placement of a same fastener in the first and second apertures while the tool is clamped to the bone. 32. The system of any of paragraphs 1 to 31, further comprising a fastener configured to be received in the apertures along the fastener-receiving axis such that the fastener attaches to at least one of the mounting portions at an aperture thereof.

33. The system of paragraph 32, wherein the fastener is separately attachable to each of the mounting portions at the first and second apertures. 34. The system of any of paragraphs 1 to 33, wherein the tool includes a guide defining a guide axis that is coaxial to the fastener-receiving axis after the mounting portions are connected to the tool.

35. The system of paragraph 34, wherein the guide is configured to receive a drill along the guide axis, wherein the jaws include a proximal jaw that engages the first mounting portion and a distal jaw that engages the second mounting portion, and wherein the tool includes a drill stop having a fixed separation from the distal jaw.

36. The system of any of paragraphs 1 to 35, wherein the tool includes a gauge configured to measure a linear dimension corresponding to a separation distance of the jaws.

37. The system of paragraph 36, wherein the gauge includes indicia representing fasteners of different length.

38. The system of paragraph 37, wherein the indicia representing fasteners of different length include different numbers, different colors, different color names, different color name abbreviations, or a combination thereof.

39. The system of any of paragraphs 36 to 38, wherein the gauge is configured to indicate a fastener of appropriate length for extending from the first aperture to the second aperture based on the linear dimension measured.

40. The system of paragraph 1, wherein the fixation device includes a clip member including the first mounting portion and the second mounting portion facing each other and interconnected by one or more elongate web members forming a collapsible portion of the clip member that folds at one or more predefined sites along each web member as the mounting portions are urged toward each other.

41. The system of paragraph 40, wherein the one or more web members include a pair of web members each separately interconnecting the mounting portions.

42. The system of paragraph 40 or 41, wherein the one or more web members are continuous with each mounting portion.

43. The system of any of paragraphs 40 to 42, wherein at least one web member has opposing ends and a predefined folding site adjacent each opposing end.

44. The system of paragraph 43, wherein the predefined folding sites adjacent each opposing end are first and second folding sites, and wherein the at least one web member further includes a third predefined folding site disposed intermediate the first and second folding sites along the web member.

45. The system of any of paragraphs 40 to 44, wherein the clip member defines a through-axis for a bone to extend through the clip member with the mounting portions across the bone from each other, and wherein at least one web member is configured to fold about one or more axes that are transverse to the through-axis as the mounting portions are urged closer to each other.

46. The system of any of paragraphs 40 to 45, wherein the clip member has a mouth region formed opposite the collapsible portion, wherein a bone-receiving axis extends from the mouth region to the collapsible portion, and wherein at least one web member is configured to fold about one or more axes that are generally parallel to the bone-receiving axis as the mounting portions are urged closer to each other.

47. The system of any of paragraphs 40 to 46, wherein the clip member defines a through-axis for a bone to extend through the clip member, and wherein each mounting portion has a characteristic dimension, and wherein each web member has a width measured parallel to the through-axis that is less than the characteristic dimension.

48. The system of any of paragraphs 40 to 47, wherein the clip member defines a through-axis for a bone to extend through the clip member with the mounting portions arranged on opposite sides of the bone and also defines a central plane orthogonal to the through-axis, and wherein each web member has a variable separation from the central plane as the web member extends from the first clip member to the second clip member.

49. The system of any of paragraphs 40 to 48, wherein clip includes a pair of web members each following and being elongated along a separate path from the first mounting portion to the second mounting portion.

50. The system of any of paragraphs 40 to 49, wherein the clip member is a first clip member, further comprising a second clip member and a plate member, the plate member being configured to extend along bone from the first clip member to the second clip member.

51. The system of paragraph 50, wherein the first clip member, the plate member, and the second clip member are continuous with one another.

52. The system of paragraph 50 or 51, wherein the plate member extends from the first mounting portion of the first clip member to the first mounting portion of the second clip member.

53. The system of paragraph 50, wherein at least one of the clip members and the plate member are formed as distinct pieces configured to overlap each other.

54. The system of any of paragraphs 40 to 53, further comprising a fastener extendable along the fastener-receiving axis to attach to the first and second mounting portions at the first and second apertures.

55. The system of any of paragraphs 40 to 54, wherein the clip member defines a through-axis for a bone to extend through the clip member with the mounting portions disposed across the bone from each other and also defining a central plane that is orthogonal to the through-axis, and wherein each web member is elongated along a path that extends from the first mounting portion to the second mounting portion with a portion of the path extending toward the central plane and another portion of the path extending away from the central plane.

56. The system of any of paragraphs 40 to 55, wherein the clip member defines a through-axis for a bone to extend through the clip member with the mounting portions disposed across the bone from each other, and wherein each member is configured to bend preferentially in planes parallel to the through-axis relative to planes orthogonal to the through-axis, if compressive force is applied to the clip member to decrease a separation distance between the mounting portions while keeping the apertures aligned with each other.

57. The system any of paragraph 1 to 56, wherein the second aperture is a slot defining a long axis, wherein the fastener-receiving axis and the long axis collectively define a fastener-receiving plane, wherein the slot has a first side wall region and a second side wall region disposed across the long axis from each other and respectively defining a first linear ridge and a second linear ridge each extending along the slot and collectively defining a ridge plane that is orthogonal to the fastener-receiving plane.

58. The system of paragraph 57, wherein the first side wall region defines a first groove and the second side wall region defines a second groove, wherein the first groove is defined between crests of a first pair of ridges and the second groove is defined between crests of a second pair of ridges, wherein the first and second grooves collectively define a groove plane that is orthogonal to the fastener-receiving plane, the system further comprising a fastener have a thread and being advanceable into the slot along the fastener-receiving axis to interchangeably attach the fastener in a first configuration having the thread disposed in the first groove and in a second configuration having the thread disposed in the second groove.

59. The system of paragraph 58, wherein the mounting portion defines a plane that is parallel to the groove plane.

60. The system of paragraph 58 or 59, wherein the fastener defines a helical channel forming a plurality of channel revolutions about a long axis of the fastener, wherein the second pair of ridges is disposed in a same channel revolution in the first configuration, and wherein the first pair of ridges is disposed in a same revolution in the second configuration.

61. The system of any of paragraphs 58 to 60, wherein the thread has a pitch, wherein each pair of ridges has a crest-to-crest spacing, and wherein the crest-to-crest spacing is less than the pitch.

62. The system of paragraph 61, wherein the crest-to-crest spacing is about one-half the pitch.

63. The system of any of paragraphs 58 to 62, wherein the ridges each have a height and the thread has a depth, and wherein the depth of the groove is at least about twice the height of the ridges.

64. The system of any of paragraphs 58 to 63, wherein the first and second mounting portions are provided by a clip that is collapsible to change an orientation of the second mounting portion relative to the first mounting portion such that the fastener-receiving axis pivots in the fastener-receiving plane to change a point at which the fastener-receiving axis intersects the long axis of the slot.

65. The system of any of paragraphs 58 to 64, wherein the second mounting portion includes a slot defining a long axis, the slot having a first linear side wall region and a second linear side wall region disposed across the long axis from each other and respectively defining a first pair of ridges and a second pair of ridges each extending parallel to the long axis, the first side wall region defining a first linear groove between crests of the first pair of ridges and the second side wall region defining a second linear groove between crests of the second pair of ridges, the system further comprising a fastener having a thread and being advanceable in a same direction and by a same distance into the slot to interchangeably attach the fastener to the slot in a first configuration with the thread disposed in the first groove and not the second groove and in a second configuration with the thread disposed in the second groove and not the first groove.

66. The system of paragraph 65, wherein the first groove and the second groove collectively define a groove plane, and wherein the second mounting portion defines a plane that is parallel to the groove plane.

67. The system of paragraph 65, wherein the first groove and the second groove collectively define a groove plane, and wherein the long axis and the fastener-receiving axis collectively define a fastener-receiving plane that is orthogonal to the groove plane.

68. The system of paragraph 65, wherein the thread has a pitch, wherein each pair of ridges has a crest-to-crest spacing, and wherein the crest-to-crest spacing is less than the pitch.

Example 5. Selected System Embodiments—Mounting Portion Defining a Slot

This example describes selected system embodiments of the present disclosure, particularly involving (a) a mounting portion defining a slot and (b) a fastener that is interchangeably attachable to the slot in distinct configurations. The selected system embodiments are presented as a series of indexed paragraphs.

1. A system for bone fixation, comprising: (A) a mounting portion configured to be disposed on bone and including a slot defining a long axis and having a first side wall region and a second side wall region disposed across the long axis from each other, the first side wall region defining a pair of ridges extending along the slot, each ridge having a crest, a groove being defined by the first side wall region between the crests; and (B) a fastener having a thread and being advanceable into the slot to interchangeably attach the fastener to the slot in a first configuration having the thread disposed in the groove and in a second configuration having the thread opposingly flanking the pair of ridges and not disposed in the groove.

2. The system of paragraph 1, wherein the second side wall region defines at least one ridge extending along the slot, and wherein the at least one ridge is opposingly flanked by the thread in the first and second configurations.

3. The system of paragraph 2, wherein a ridge defined by the first side wall region and the ridge defined by the second side wall region collectively define a ridge plane, and wherein the mounting portion defines a plane at the slot that is parallel to the ridge plane.

4. The system of paragraph 2, wherein a ridge defined by the first side wall region and the ridge defined by the second side wall region collectively define a ridge plane, and wherein the slot defines a fastener-receiving plane orthogonal to the ridge plane.

5. The system of paragraph 2, wherein the pair of ridges is a first pair of ridges and the groove is a first groove, wherein the second side wall region defines a second pair of ridges each having a crest, and wherein a second groove is defined by the second side wall region between crests of the second pair of ridges.

6. The system of paragraph 5, wherein in the first configuration the thread opposingly flanks the second pair of ridges and is not disposed in the second groove, and wherein in the second configuration the thread is disposed in the second groove.

7. The system of paragraph 5, wherein the first groove and the second groove collectively define a groove plane, and wherein the slot defines a fastener-receiving plane orthogonal to the groove plane.

8. The system of paragraph 7, wherein the mounting portion defines a plane at the slot, and wherein the plane at the slot is parallel to the groove plane.

9. The system of any of paragraphs 1 to 8, wherein the thread has a pitch, wherein the pair of ridges has a crest-to-crest spacing, and wherein the crest-to-crest spacing is less than the pitch.

10. The system of paragraph 9, wherein the crest-to-crest spacing is about one-half the pitch.

11. The system of any of paragraphs 1 to 10, wherein the ridges and the thread each have a height, and wherein the height of the thread is more than the height of the ridges.

12. The system of any of paragraphs 1 to 11, wherein the mounting portion is a second mounting portion, further comprising a clip member including a first mounting portion and the second mounting portion connected to and facing the first mounting portion.

13. The system of paragraph 12, wherein the first mounting portion includes an aperture defining a fastener-receiving axis, and wherein the fastener is extendable along the fastener-receiving axis to interchangeably attach the fastener to the slot in the first configuration and the second configuration.

14. The system of paragraph 13, wherein the slot defines a fastener-receiving plane containing the fastener-receiving axis, wherein the clip member is collapsible to change an orientation of the second mounting portion relative to the first mounting portion such that the fastener-receiving axis pivots in the fastener-receiving plane to change a point at which the fastener-receiving axis intersects the long axis of the slot.

15. The system of paragraph 13 or 14, wherein the fastener is attachable to the first mounting portion at the aperture. 16. The system of any of paragraphs 12 to 15, wherein the clip member is provided by a single piece.

17. The system of any of paragraphs 1 to 16, wherein each ridge is at least substantially linear.

18. A system for bone fixation, comprising: (A) a mounting portion configured to be disposed on bone and including a slot defining a long axis and a fastener-receiving plane containing the long axis, the slot having a first side wall region and a second side wall region disposed across the long axis from each other and respectively defining a first pair of at least substantially linear ridges and a second pair of at least substantially linear ridges, the first side wall region defining a first groove between crests of the first pair of ridges and the second side wall region defining a second groove between crests of the second pair of ridges, the first and second grooves collectively defining a groove plane that is orthogonal to the fastener-receiving plane; and (B) a fastener having a thread and being advanceable into the slot along a fastener-receiving axis in the fastener-receiving plane, to interchangeably attach the fastener in a first configuration having the thread disposed in the first groove and in a second configuration having the thread disposed in the second groove.

19. The system of paragraph 18, wherein the mounting portion defines a plane at the slot that is parallel to the groove plane.

20. The system of paragraph 18 or 19, wherein the fastener defines a helical channel extending a plurality of revolutions about a long axis of the fastener, wherein the second pair of ridges is disposed in a same revolution of the helical channel in the first configuration, and wherein the first pair of ridges is disposed in a same revolution of the helical channel in the second configuration.

21. The system of paragraph 20, wherein the thread has a pitch, wherein each pair of ridges has a crest-to-crest spacing, and wherein the crest-to-crest spacing is less than the pitch.

22. The system of paragraph 21, wherein the crest-to-crest spacing is about one-half the pitch.

23. The system of any of paragraphs 18 to 22, wherein the fastener is advanceable into the slot along each of a plurality of nonparallel fastener-receiving axes in the fastener-receiving plane for interchangeable attachment to the slot in the first and second configurations. 24. The system of any of paragraphs 18 to 23, wherein the ridges each have a height and the thread has a height, and wherein the height of the thread more than the height of the ridges.

25. The system of any of paragraphs 18 to 24, wherein the mounting portion is a second mounting portion, further comprising a clip member including a first mounting portion and the second mounting portion connected to and facing the first mounting portion.

26. The system of paragraph 25, wherein the first mounting portion includes an aperture defining the fastener-receiving axis.

27. The system of paragraph 25 or 26, wherein the clip member is collapsible to change an orientation of the second mounting portion relative to the first mounting portion such that the fastener-receiving axis pivots in the fastener-receiving plane to change a point at which the fastener-receiving axis intersects the long axis of the slot.

28. The system of paragraph 26 or 27, wherein the fastener is threadably engageable with the aperture.

29. The system of any of paragraphs 25 to 28, wherein the clip member is provided by a single piece.

30. A system for bone fixation, comprising: (A) a mounting portion configured to be disposed on bone and including a slot defining a long axis, the slot having a first linear side wall region and a second linear side wall region disposed on opposite sides of the long axis from each other and respectively defining a first pair of ridges and a second pair of ridges each extending parallel to the long axis, the first side wall region defining a first linear groove between crests of the first pair of ridges and the second side wall region defining a second linear groove between crests of the second pair of ridges; and (B) a fastener having a thread and being advanceable in a same direction and by a same distance into the slot to interchangeably attach the fastener to the slot in a first configuration with the thread disposed in the first groove and not the second groove and in a second configuration with the thread disposed in the second groove and not the first groove.

31. The system of paragraph 30, wherein the first groove and the second groove collectively define a groove plane, and wherein the mounting portion defines a plane at the slot that is parallel to the groove plane.

32. The system of paragraph 30 or 31, wherein the first groove and the second groove collectively define a groove plane, and wherein the slot defines a fastener-receiving plane that is orthogonal to the groove plane.

33. The system of any of paragraphs 30 to 32, wherein the thread has a pitch, wherein each pair of ridges has a crest-to-crest spacing, and wherein the crest-to-crest spacing is less than the pitch.

34. The system of paragraph 33, wherein the crest-to-crest spacing is about one-half the pitch.

35. The system of any of paragraphs 30 to 34, wherein the fastener is advanceable into the slot along each of a plurality of nonparallel fastener-receiving axes in the fastener-receiving plane for interchangeable attachment to the slot in the first and second configurations.

36. A method of fixing bone, the method comprising: (A) selecting the mounting portion and the fastener of any of paragraphs 1 to 35; (B) disposing the mounting portion on a bone; and (C) securing the mounting portion to the bone with the fastener in the first configuration or the second configuration.

Example 6. Selected Device Embodiments—Clip Member with Web Members

This example describes selected device embodiments of the present disclosure involving a clip member that includes one or more with web members. The selected device embodiments are presented as a series of indexed paragraphs.

1. A device for bone fixation, comprising: a clip member configured to be placed on bone and including a first mounting portion and a second mounting portion facing each other and respectively defining a first aperture and a second aperture aligned with each other on a same fastener-receiving axis, the mounting portions being interconnected by one or more elongate web members forming a collapsible portion of the clip member that folds at one or more predefined sites along each web member as the mounting portions are urged closer to each other.

2. The device of paragraph 1, wherein the one or more web members include a pair of web members each separately interconnecting the mounting portions.

3. The device of paragraph 1 or 2, wherein the one or more web members are connected integrally to each mounting portion.

4. The device of any of paragraphs 1 to 3, wherein at least one web member has opposing ends and a predefined folding site adjacent each opposing end.

5. The device of paragraph 4, wherein the predefined folding sites adjacent each opposing end are first and second folding sites, and wherein the at least one web member further includes a third predefined folding site disposed intermediate the first and second folding sites along the web member.

6. The device of any of paragraphs 1 to 5, wherein the clip member defines a through-axis for a bone to extend through the clip member with the mounting portions across the bone from each other, and wherein at least one web member is configured to fold about one or more axes that are transverse to the through-axis as the mounting portions are urged closer to each other.

7. The device of any of paragraphs 1 to 6, wherein the clip member has a mouth region formed opposite the collapsible portion, wherein a bone-receiving axis extends from the mouth region to the collapsible portion, and wherein at least one web member is configured to fold about one or more axes that are generally parallel to the bone-receiving axis as the mounting portions are urged closer to each other.

8. The device of any of paragraphs 1 to 7, wherein the clip member defines a through-axis for a bone to extend through the clip member, and wherein each mounting portion has a characteristic dimension measured parallel to the through-axis, and wherein each web member has a width that is less than the characteristic dimension.

9. The device of any of paragraphs 1 to 8, wherein the clip member defines a through-axis for a bone to extend through the clip member with the mounting portions disposed on opposite sides of the bone and also defines a central plane orthogonal to the through-axis, and wherein each web member has a variable separation from the central plane as the web member extends from the first clip member to the second clip member.

10. The device of any of paragraphs 1 to 9, wherein clip includes a pair of web members each following and being elongated along a separate path from the first mounting portion to the second mounting portion.

11. The device of any of paragraphs 1 to 10, wherein the clip member is a first clip member, further comprising a second clip member and a plate member, the plate member being configured to extend along bone from the first clip member to the second clip member.

12. The device of paragraph 11, wherein the first clip member, the plate member, and the second clip member are formed integrally with one another.

13. The device of paragraph 12, wherein the plate member extends from the first mounting portion of the first clip member to the first mounting portion of the second clip member.

14. The device of paragraph 11, wherein at least one of the clip members and the plate member are formed as distinct pieces configured to overlap each other.

15. The device of any of paragraphs 1 to 14, further comprising a fastener extendable along the fastener-receiving axis to lock to the first and second mounting portions at the first and second apertures.

16. The device of any of paragraphs 1 to 15, wherein the clip member defines a through-axis for a bone to extend through the clip member with the mounting portions disposed across the bone from each other and also defining a central plane that is orthogonal to the through-axis, and wherein each web member is elongated along a path that extends from the first mounting portion to the second mounting portion with a portion of the path extending toward the central plane and another portion of the path extending away from the central plane.

17. The device of any of paragraphs 1 to 16, wherein the clip member defines a through-axis for a bone to extend through the clip member with the mounting portions disposed across the bone from each other, and wherein each member is configured to bend preferentially in planes parallel to the through-axis relative to planes orthogonal to the through-axis, if compressive force is applied to the clip member to decrease a separation distance between the mounting portions while keeping the apertures aligned with each other.

18. A method of fixing bone, the method comprising: (A) selecting the clip member of any of paragraphs 1 to 17; (B) disposing the clip member on a bone with the first and second mounting portions across the bone from each other; (C) applying compressive force to the mounting portions to urge the mounting portions closer to each other and fold the collapsible portion; and (D) attaching the clip member to the bone with a fastener extending from the first aperture to the second aperture.

19. The method of paragraph 18, wherein the step attaching including a step of attaching the fastener to each of the first and second apertures.

20. The method of paragraph 18 or 19, wherein the step of applying compressive force is performed with a clamping device that maintains the first and second apertures in alignment with each other.

21. The method of any of paragraphs 18 to 20, wherein the bone is a rib bone.

22. The method of any of paragraphs 18 to 21, wherein the clip member is a first clip member, and wherein the steps of selecting, disposing, applying, and attaching are performed with a second clip member such that a plate member extends along the bone from the first clip member to the second clip and is attached to the bone by the clip members.

23. A device for bone fixation, comprising: a clip member configured to be placed on bone and including a first mounting portion and a second mounting portion facing each other and respectively defining a first aperture and a second aperture aligned to receive a same linear fastener, the clip member defining a through-axis for a bone to extend through the clip member with the mounting portions across the bone from each other, the mounting portions being interconnected by one or more elongate web members forming a collapsible portion of the clip member, each web member being configured to bend about one or more axes that are transverse to the through-axis, if the mounting portions are urged closer together while the first and second apertures are maintained in alignment with each other.

24. A method of fixing bone, the method comprising: (A) selecting a clip member including a first mounting portion and a second mounting portion facing each other; (B) disposing the clip member on a bone with the first and second mounting portions across the bone from each other; (C) applying compressive force to the mounting portions with a clamping device to urge the mounting portions closer to each other and to move at least one of the mounting portions closer to the bone; and (D) attaching the clip member to the bone with a fastener extending from a first aperture defined by the first mounting portion, through the bone, and to a second aperture defined by the second mounting portion, with the fastener locked to at least one of the apertures.

25. The method of paragraph 24, wherein the clip selected defines an axis extending through the first and second apertures, and wherein the clamping device that maintains the first and second apertures on the axis as a separation distance between the mounting portions decreases.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. An instrument for installing a bone fixation device, the instrument comprising:
   a frame member formed to include a distal jaw and a drill stop including a notch, wherein the distal jaw and the drill stop extend from a body portion of the frame member in a same direction, wherein the drill stop is not part of the distal jaw;
   a carriage formed to include a proximal jaw, the carriage slidably coupled to the frame member so as to form a receiver region between the distal jaw and the proximal jaw; and
   a drive screw engaged with the frame member and/or the carriage such that rotation of the drive screw causes relative movement between the frame member and the carriage, wherein relative movement between the carriage and the frame member adjusts a distance between the distal jaw and the proximal jaw.

2. The instrument of claim 1, wherein the distal jaw is at a distal end of the frame member and the drill stop is at a proximal end of the frame member.

3. The instrument of claim 1, wherein a distance between the distal jaw and the drill stop is fixed.

4. The instrument of claim 1, wherein the notch of the drill stop is curved.

5. The instrument of claim 4, wherein an axis through a center of curvature of the notch is parallel to an axis about which the drive screw rotates.

6. The instrument of claim 4, wherein an axis through a center of curvature of the notch extends through an opening of the carriage.

7. The instrument of claim 1, wherein the drill stop is a first drill stop, and wherein the frame member is formed to include a second drill stop.

8. The instrument of claim 1, further comprising a gauge configured to display an indication corresponding to a distance between the proximal and distal jaws.

9. The instrument of claim 8, wherein the frame member includes the gauge.

10. The instrument of claim 1, wherein the distal jaw includes one or more projections extending into the receiver region.

11. The instrument of claim 1, wherein the proximal jaw includes one or more projections extending into the receiver region.

12. The instrument of claim 1, wherein each the distal jaw and the proximal jaw includes one or more projections extending into the receiver region.

13. An instrument for installing a bone fixation device, the instrument comprising:
   a frame member formed to include a distal jaw;
   a carriage formed to include a proximal jaw, the carriage slidably coupled to the frame member so as to form a receiver region between the distal jaw and the proximal jaw, wherein the frame member has a greater length than the carriage, and wherein each the distal jaw and the proximal jaw includes one or more projections extending into the receiver region;
   a drive screw engaged with the frame member and/or the carriage such that rotation of the drive screw causes relative movement between the frame member and the carriage along an axis, the axis parallel to a longitudinal axis of a body portion of the frame member, wherein relative movement between the carriage and the frame member adjusts a distance between the distal jaw and the proximal jaw along the axis; and
   a gauge configured to display an indication corresponding to the distance between the proximal and distal jaws.

14. The instrument of claim 13, wherein rotation of the drive screw causes the carriage to move relative to the frame member.

15. The instrument of claim 13, further comprising a rotatable locking member coupled to the carriage, the locking member including a threaded portion that extends into the receiver region.

16. The instrument of claim 15, wherein the locking member is coupled to the carriage such that the locking member may translate along an axis about which the locking member rotates.

17. An instrument for installing a bone fixation device, the instrument comprising:
   a frame member formed to include a distal jaw and a drill stop including a notch, wherein the distal jaw and the drill stop extend from a body portion of the frame member in a same direction, the distal jaw is at a distal end of the frame member and the drill stop is at a proximal end of the frame member;
   a carriage formed to include a proximal jaw, the carriage slidably coupled to the frame member so as to form a receiver region between the distal jaw and the proximal jaw; and
   a drive screw engaged with the frame member and/or the carriage such that rotation of the drive screw causes relative movement between the frame member and the carriage, wherein relative movement between the carriage and the frame member adjusts a distance between the distal jaw and the proximal jaw.

18. The instrument of claim 17, wherein a distance between the distal jaw and the drill stop is fixed.

19. The instrument of claim 17, further comprising a gauge configured to display an indication corresponding to a distance between the proximal and distal jaws.

20. The instrument of claim 19, wherein the frame member includes the gauge.

* * * * *